US010597382B2

(12) United States Patent
Wang et al.

(10) Patent No.: US 10,597,382 B2
(45) Date of Patent: Mar. 24, 2020

(54) TETRAZOLE CONTAINING APOPTOSIS SIGNAL-REGULATING KINASE 1 INHIBITORS AND METHODS OF USE THEREOF

(71) Applicant: ENANTA PHARMACEUTICALS, INC., Watertown, MA (US)

(72) Inventors: Guoqiang Wang, Belmont, MA (US); Jing He, Somerville, MA (US); Bin Wang, Brighton, MA (US); Ruichao Shen, Belmont, MA (US); Brett Granger, Sudbury, MA (US); Yat Sun Or, Watertown, MA (US)

(73) Assignee: Enanta Pharmaceuticals, Inc., Watertown, MA (US)

( * ) Notice: Subject to any disclaimer, the term of this patent is extended or adjusted under 35 U.S.C. 154(b) by 0 days.

(21) Appl. No.: 16/113,611

(22) Filed: Aug. 27, 2018

(65) Prior Publication Data

US 2019/0062310 A1 Feb. 28, 2019

Related U.S. Application Data

(60) Provisional application No. 62/550,951, filed on Aug. 28, 2017.

(51) Int. Cl.
| | | |
|---|---|---|
| *C07D 401/14* | (2006.01) | |
| *C07D 413/14* | (2006.01) | |
| *C07D 471/04* | (2006.01) | |
| *A61P 13/12* | (2006.01) | |
| *A61P 3/10* | (2006.01) | |
| *A61P 1/16* | (2006.01) | |

(52) U.S. Cl.
CPC ......... *C07D 401/14* (2013.01); *C07D 413/14* (2013.01); *C07D 471/04* (2013.01); *A61P 1/16* (2018.01); *A61P 3/10* (2018.01); *A61P 13/12* (2018.01)

(58) Field of Classification Search
CPC ... C07D 401/14; C07D 413/14; C07D 471/04
USPC ...................................................... 544/180
See application file for complete search history.

(56) References Cited

U.S. PATENT DOCUMENTS

| | | |
|---|---|---|
| 6,534,651 B2 | 3/2003 | Jagtap et al. |
| 8,378,108 B2 | 2/2013 | Corkey et al. |
| 8,653,075 B2 | 2/2014 | Grundl et al. |
| 9,067,933 B2 | 6/2015 | Corkey et al. |
| 9,254,284 B2 | 2/2016 | Notte |
| 2005/0113450 A1 | 5/2005 | Thorarensen et al. |
| 2009/0318425 A1 | 12/2009 | Chang et al. |
| 2010/0029619 A1 | 2/2010 | Osamu et al. |
| 2011/0009410 A1 | 1/2011 | Corkey et al. |
| 2012/0004267 A1 | 1/2012 | Corkey et al. |
| 2013/0203731 A1 | 8/2013 | Chang et al. |
| 2013/0210810 A1 | 8/2013 | Singh et al. |
| 2014/0018370 A1 | 1/2014 | Corkey et al. |
| 2014/0249135 A1 | 9/2014 | Burger et al. |
| 2014/0329850 A1 | 11/2014 | Chang |
| 2015/0005280 A1 | 1/2015 | Sasmal et al. |
| 2018/0327388 A1 | 11/2018 | Wang et al. |
| 2018/0362501 A1 | 12/2018 | Wang et al. |
| 2018/0362502 A1 | 12/2018 | Granger et al. |
| 2018/0362503 A1 | 12/2018 | Granger et al. |
| 2019/0062310 A1 | 2/2019 | Wang et al. |

FOREIGN PATENT DOCUMENTS

| | | |
|---|---|---|
| CN | 107793400 A | 3/2018 |
| WO | 2004018428 A1 | 3/2004 |
| WO | 2005009470 A1 | 2/2005 |
| WO | 2005103288 A1 | 11/2005 |
| WO | 2007000339 A1 | 1/2007 |
| WO | 2008016131 A1 | 2/2008 |
| WO | 2008082579 A1 | 7/2008 |
| WO | 2009027283 A1 | 3/2009 |
| WO | 2009123986 A1 | 10/2009 |
| WO | 2010008843 A1 | 1/2010 |
| WO | 2011008709 A1 | 1/2011 |
| WO | 2011041293 A1 | 4/2011 |
| WO | 2011097079 A1 | 8/2011 |
| WO | 2012003387 A3 | 1/2012 |
| WO | 2012011548 A1 | 1/2012 |

(Continued)

OTHER PUBLICATIONS

Lanier et al. ACS Medicinal Chemistry Letters (2017), 8(3), 316-320.*

(Continued)

*Primary Examiner* — Kahsay Habte
(74) *Attorney, Agent, or Firm* — Edgar W. Harlan; Carolyn S. Elmore; Elmore Patent Law Group, P.C.

(57) ABSTRACT

The present invention discloses compounds of Formula (I), or pharmaceutically acceptable salts, ester, stereoisomer, tautomer, solvate, hydrate, or combination thereof:

which inhibit the Apoptosis signal-regulating kinase 1 (ASK-1), which associated with autoimmune disorders, neurodegenerative disorders, inflammatory diseases, chronic kidney disease, cardiovascular disease. The present invention further relates to pharmaceutical compositions comprising the aforementioned compounds for administration to a subject suffering from ASK-1 related disease. The invention also relates to methods of treating an ASK-1 related disease in a subject by administering a pharmaceutical composition comprising the compounds of the present invention. The present invention specifically relates to methods of treating ASK-1 associated with hepatic steatosis, including non-alcoholic fatty liver disease (NAFLD) and non-alcohol steatohepatitis disease (NASH).

17 Claims, No Drawings

(56) References Cited

FOREIGN PATENT DOCUMENTS

| | | | |
|---|---|---|---|
| WO | 2012080735 A1 | 6/2012 | |
| WO | 2013112741 A1 | 8/2013 | |
| WO | 2014100541 A1 | 6/2014 | |
| WO | 2014106019 A2 | 7/2014 | |
| WO | 2014137728 A1 | 9/2014 | |
| WO | 2015095059 A1 | 6/2015 | |
| WO | 2016049069 A1 | 3/2016 | |
| WO | 2016049070 A1 | 3/2016 | |
| WO | 2016105453 A1 | 6/2016 | |
| WO | 2016106384 A1 | 6/2016 | |
| WO | 2018090869 A1 | 5/2018 | |
| WO | 2018133856 A1 | 7/2018 | |
| WO | 2018133866 A1 | 7/2018 | |
| WO | 2018148204 A1 | 8/2018 | |
| WO | 2018149284 A1 | 8/2018 | |
| WO | 2018151830 A1 | 8/2018 | |
| WO | 2018157857 A1 | 9/2018 | |
| WO | 2018169742 A1 | 9/2018 | |
| WO | 2018218051 A1 | 11/2018 | |

OTHER PUBLICATIONS

Gibson, et al., "Structure-based drug design of novel ASK1 inhibitors using an integrated lead optimization strategy," Bioorganic & Medicinal Chemistry Letters, pp. 1-5, 2017.

Monastyrskyi, et al., "Discovery of 2-arylquinazoline derivatives as a new class of ASK1 inhibitors," Bioorganic & Medicinal Chemistry Letters, 28:400-404, 2018.

Lovering, et al., "Rational approach to highly potent and selective apoptosis signal regulating kinase 1 (ASK1) inhibitors," European Journal of Medicinal Chemistry, 145:606-621, 2018.

Loomba, et al., "The ASK1 Inhibitor Selonsertib in Patients with Nonalcoholic Steatohepatitis: A Randomized, Phase 2 Trial," Hepatology 67(2):549-559, 2018.

Volynets, et al., "Identification of 3H-Naphtho[1,2,3-de]quinoline-2,7-diones as Inhibitors of Apoptosis Signal Regulating Kinase 1 (ASK1)," Journal of Medicinal Chemistry, 54:2680-2686, 2011.

Volynets, et al., "Rational design of apoptosis signal-regulating kinase 1 inhibitors: Discovering novel structural scaffold," European Journal of Medicinal Chemistry 61:104-115, 2013.

Terao, et al., "Design and biological evaluation of imidazo[1,2-a]pyridines as novel and potent ASK1 inhibitors," Biooganic & Medicinal Chemistry Letters, 22:7326-7329, 2012.

U.S. Appl. No. 15/979,128, filed May 14, 2018.
U.S. Appl. No. 15/988,763, filed May 24, 2018.
U.S. Appl. No. 15/988,806, filed May 24, 2018.
U.S. Appl. No. 15/988,783, filed May 24, 2018.

Pubmed Compound Summary for CID 53276841, '2-Methyl-1,1,3-trioxo-N-pyridin-2-yl-1,2-benzolhiazole-6-carboxamide', U.S. National library of Medicine, Aug. 1, 2011 (Aug. 1, 2011), p. 1-7; p2 (https:/lpubchem.ncbi.nlm.nih.gov/compound/53276841).

Patani, George A. et al., "Bioisosterism: A Rational Approach in Drug Design", Chem. Rev., 96, 1996, 3147-3176.

Sheridan, Robert P., "The Most Common Chemical Replacements in Drug-Like Compounds", J. Chem. Info. Comput. Sci. 2002, vol. 42, 2002, 103-108.

Wermuth, C. G., "Molecular Variations Based on Isosteric Replacements", in "The Practice of Medicinal Chemistry", Academic Press Limited, 1996, 203-237.

Kawarazaki, et al., "Apoptosis signal-regulating kinase 1 as a therapeutic target," Expert Opinion on Therapeutic Targets, 18(6):651-664, 2014.

Starosyla, S., et al., "ASK1 Pharmacophore Model Derived from Diverse Classes of Inhibitors," Bioorganic & Medicinal Chemistry Letters 24: pp. 4418-4423 (2014).

\* cited by examiner

TETRAZOLE CONTAINING APOPTOSIS SIGNAL-REGULATING KINASE 1 INHIBITORS AND METHODS OF USE THEREOF

RELATED APPLICATIONS

This application claims the benefit of U.S. Provisional Application No. 62/550,951, filed on Aug. 28, 2017. The entire teachings of the above application are incorporated herein by reference.

TECHNICAL FIELD

The present invention relates generally to compounds and pharmaceutical compositions useful as ASK-1 inhibitors. Specifically, the present invention relates to compounds useful as inhibitors of ASK-1 and methods for their preparation and use.

BACKGROUND OF THE INVENTION

Apoptosis signal-regulating kinase 1 (ASK-1) is a member of the mitogen-activated protein kinase kinase kinase (MAPKKK, MAP3K) family, which when activated phosphorylates downstream MAP kinase kinases (MAPKK, MAP2K), which in turn activate MAP kinases (MAPK). MAPKs elicit a response by phosphorylating cellular substrates, thus regulating the activity of transcription factors that ultimately control gene expression. Specifically ASK-1, also known as MAPKKK5, phosphorylates MAPKK4/MAPKK7 or MAPKK3/MAPKK6, which subsequently phosphorylates and activates the c-Jun N-terminal protein kinase (JNK) and p38 MAPKs, respectively (H. Ichijo, et al., *Cell Comm. Signal* 2009, 7, 1-10; K. Takeda, et al., *Annu. Rev. Pharmacol. Toxicol.* 2008, 48, 199-225; H. Nagai, et al., *J. Biochem. Mol. Biol.* 2007, 40, 1-6). Activation of the JNK and p38 pathways triggers a downstream stress response such as apoptosis, inflammation, or differentiation (H. Ichijo, et al., *Science* 1997, 275, 90-94; K. Takeda, et al., *J. Biol. Chem.* 2000, 275, 9805-9813; K. Tobiume, et al., *EMBO Rep.* 2001, 2, 222-228; K. Sayama et al., *J. Biol. Chem.* 2001, 276, 999-1004).

The activity of ASK-1 is regulated by thioredoxin (Trx), which binds to the N-terminal end of ASK-1 (M. Saitoh, et al., *EMBO J.* 1998, 17, 2596-2606). ASK-1 is activated succeeding autophosphorylation at Thr838 in response to environmental stimuli including oxidative stress, lipopolysaccharides (LPS), reactive oxygen species (ROS), endoplasmic reticulum (ER) stress, an increase in cellular calcium ion concentrations, Fas ligand, and various cytokines such as tumor necrosis factor (TNF) (H. Nishitoh, et al., *Genes Dev.* 2002, 16, 1345-1355; K. Takeda, et al., *EMBO Rep.* 2004, 5, 161-166; A. Matsuzawa, et al., *Nat. Immunol.* 2005, 6, 587-592).

ASK-1 has been associated with autoimmune disorders, neurodegenerative disorders, inflammatory diseases, chronic kidney disease, cardiovascular disease, metabolic disorders, and acute and chronic liver diseases (R. Hayakawa, et al., *Proc. Jpn. Acad., Ser. B* 2012, 88, 434-453).

More specifically, ASK-1 has been associated with hepatic steatosis, including non-alcoholic fatty liver disease (NAFLD) and non-alcohol steatohepatitis (NASH). In a mouse model, high fat diets have caused induction of hepatic steatosis, ultimately causing fat accumulation and fatty acid oxidation. This led to the generation of ROS which caused hepatocyte dysfunction and death (S. K. Mantena, et al., *Free Radic. Biol. Med.* 2008, 44, 1259-1272; S. K. Mantena, et al., *Biochem.* 1 2009, 417, 183-193). Moreover, TNF was shown to be critical for apoptosis of hepatocytes through the ASK-1-JNK pathway, and TNF deficient mice showed reduced hepatic steatosis and fibrosis (W. Zhang, et al., *Biochem. Biophys. Res. Commun.* 2010, 391, 1731-1736).

Small molecule compounds which act as ASK-1 inhibitors have been disclosed in the following publications: WO 2008/016131, WO 2009/027283, WO 2009/0318425, WO 2009/123986, US 2009/0318425, WO 2011/041293, WO 2011/097079, US 2011/0009410, G. P. Volynets, et al., *J. Med. Chem.* 2011, 54, 2680-2686, WO 2012/003387, WO 2012/011548, WO 2012/080735, Y. Terao, et al., *Bioorg. Med. Chem. Lett.* 2012, 22, 7326-7329, WO 2013/112741, G. P. Volynets, et al., *Eur. J. Med. Chem.* 2013, 16, 104-115, US 2014/0018370, WO 2014/100541, WO 2015/095059, WO 2016/049069, WO 2016/049070, WO 2018133865 and WO 2018133866.

There is a need for the development of ASK-1 inhibitors for the treatment and prevention of disease. The present invention has identified compounds which inhibit ASK-1 as well as methods of using these compounds to treat disease.

SUMMARY OF THE INVENTION

In one aspect, the invention provides compounds represented by Formula I, or a pharmaceutically acceptable salt, ester, or combination thereof:

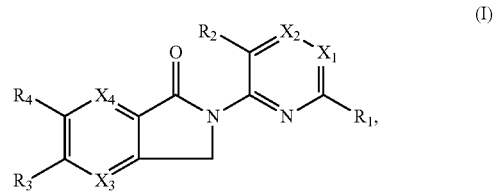

(I)

wherein
$R_1$ is selected from the groups below:

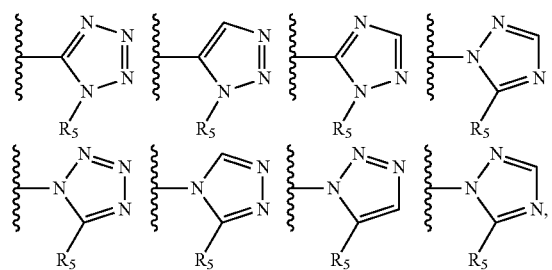

Each of which is optionally substituted when possible;
$R_5$ is selected from the group consisting of:
1) Hydrogen;
2) Optionally substituted —$C_1$-$C_8$ alkyl;
3) Optionally substituted —$C_2$-$C_8$ alkenyl;
4) Optionally substituted —$C_2$-$C_8$ alkynyl;
5) Optionally substituted —$C_3$-$C_8$ cycloalkyl;
6) Optionally substituted aryl;
7) Optionally substituted arylalkyl;
8) Optionally substituted 3- to 8-membered heterocycloalkyl;

9) Optionally substituted heteroaryl; and
10) Optionally substituted heteroarylalkyl;

$X_1$, $X_2$, $X_3$ and $X_4$ are each independently selected from N and $C(R_6)$;

$R_2$ and $R_6$ are each independently selected from the group consisting of:
1) Hydrogen;
2) Halogen;
3) —$NO_2$;
4) Cyano;
5) Optionally substituted —$C_1$-$C_8$ alkyl;
6) Optionally substituted —$C_1$-$C_8$ cycloalkyl; and
7) Optionally substituted 3- to 8-membered heterocycloalkyl;

$R_3$ and $R_4$ are each independently selected from the group consisting of:
1) Hydrogen;
2) Halogen;
3) —$NO_2$;
4) Cyano;
5) Optionally substituted —$C_1$-$C_8$ alkyl;
6) Optionally substituted —$C_2$-$C_8$ alkenyl;
7) Optionally substituted —$C_2$-$C_8$ alkynyl;
8) Optionally substituted —$C_3$-$C_8$ cycloalkyl;
9) Optionally substituted aryl;
10) Optionally substituted arylalkyl;
11) Optionally substituted 3- to 8-membered heterocycloalkyl;
12) Optionally substituted heteroaryl;
13) Optionally substituted heteroarylalkyl;
14) —$OR_7$;
15) —$N(R_7)(R_8)$;
16) —$S(O)_2N(R_7)(R_8)$;
17) —$N(R_7)C(O)R_8$; and
18) —$N(R_7)S(O)_2R_8$;

wherein $R_7$ and $R_8$ are independently selected from the group consisting of hydrogen; —$C_1$-$C_{15}$ alkyl; cycloalkyl; heterocycloalkyl; aryl, and heteroaryl, each of which is optionally substituted with 1 to 3 substituents independently selected from halo; alkyl; alkylamino; dialkylamino; alkylC(O)NH—; arylC(O)NH—; heteroarylC(O)NH-amido; —CN, alkoxy; —$CF_3$; aryl, and heteroaryl, or $R_7$ and $R_8$ are taken together with the nitrogen atom to which they are attached to form a heterocyclic.

In another embodiment, the present invention provides a pharmaceutical composition comprising a therapeutically effective amount of a compound or combination of compounds of the present invention, or a pharmaceutically acceptable salt, ester or combination thereof, in combination with a pharmaceutically acceptable carrier or excipient.

In another embodiment, the present invention provides a method for the prevention or treatment of an ASK-1 mediated disease or condition ion a subject in need thereof. The method comprises administering to the subject a therapeutically effective amount of a compound of Formula (I). The present invention also provides the use of a compound of Formula (I) for the preparation of a medicament for the prevention or treatment of an ASK-1 mediated disease or condition. Such diseases include autoimmune disorders, neurodegenerative disorders, inflammatory diseases, chronic kidney disease, cardiovascular disease, metabolic disorders, and acute and chronic liver diseases.

DETAILED DESCRIPTION OF THE INVENTION

A first embodiment of the invention is a compound represented by Formula I as described above, or a pharmaceutically acceptable salt, ester, or combination thereof.

In certain embodiments, the present invention relates to compounds of Formula (I), and pharmaceutically acceptable salts and esters thereof, wherein $X_1$ is CH. In certain embodiments, the present invention relates to compounds of Formula (I), and pharmaceutically acceptable salts and esters thereof, wherein $X_2$ is CH. In certain embodiments, the present invention relates to compounds of Formula (I), and pharmaceutically acceptable salts, esters and combinations thereof, wherein $X_1$ is CH, and $X_2$ is CH.

In certain embodiments, the present invention relates to compounds of Formula (I), and pharmaceutically acceptable salts and esters thereof, wherein $X_3$ is CH. In certain embodiments, the present invention relates to compounds of Formula (I), and pharmaceutically acceptable salts, esters and combinations thereof, wherein $X_4$ is CH. In certain embodiments, the present invention relates to compounds of Formula (I), and pharmaceutically acceptable salts, esters and combinations thereof, wherein $X_3$ is CH and $X_4$ is CH.

In certain embodiments, the present invention relates to compounds of Formula (I), and pharmaceutically acceptable salts and esters thereof, wherein $X_4$ is N. In certain embodiments, the present invention relates to compounds of Formula (I), and pharmaceutically acceptable salts, esters and combinations thereof, wherein $X_3$ is CH and $X_4$ is N.

In certain embodiments, the present invention relates to compounds of Formula (I), and pharmaceutically acceptable salts and esters thereof, wherein $R_3$ is hydrogen. In certain embodiments, the present invention relates to compounds of Formula (I), and pharmaceutically acceptable salts, esters and combinations thereof, wherein $R_3$ is halogen. In certain embodiments, the present invention relates to compounds of Formula (I), and pharmaceutically acceptable salts and esters thereof, wherein $R_3$ is $CH_3$, $CF_3$, $NH_2$, NH(Me), $N(Me)_2$, or F.

In certain embodiments, the present invention relates to compounds of Formula (I), and pharmaceutically acceptable salts, esters and combinations thereof, wherein $R_3$ is selected from:

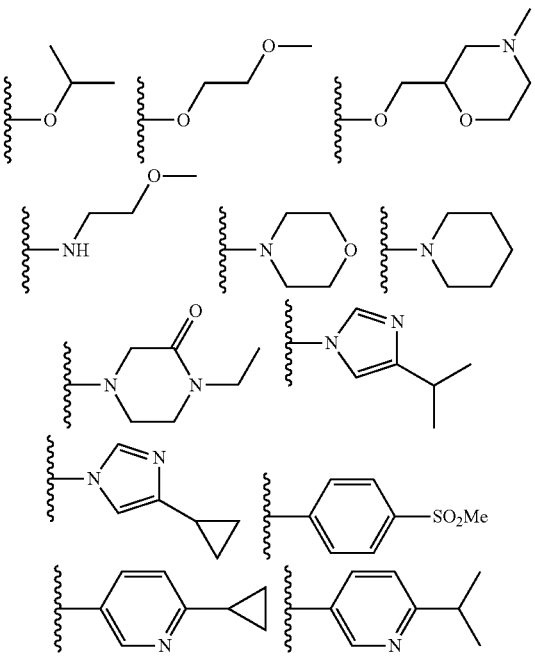

-continued

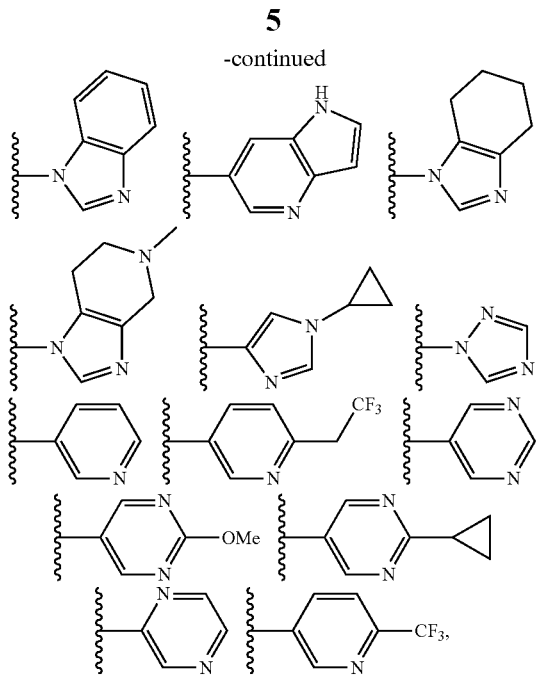

wherein each of the above shown groups is optionally substituted.

In certain embodiments, the present invention relates to compounds of Formula (I), and pharmaceutically acceptable salts, esters and combinations thereof, wherein $R_4$ is hydrogen. In certain embodiments, the present invention relates to compounds of Formula (I), and pharmaceutically acceptable salts, esters and combinations thereof, wherein $R_4$ is halogen. In certain embodiments, the present invention relates to compounds of Formula (I), and pharmaceutically acceptable salts, esters and combinations thereof, wherein $R_4$ is $CH_3$, $CF_3$, $NH_2$, NHMe, $N(Me)_2$, or F.

In certain embodiments, the present invention relates to compounds of Formula (I), and pharmaceutically acceptable salts, esters and combinations thereof, wherein $R_4$ is selected from:

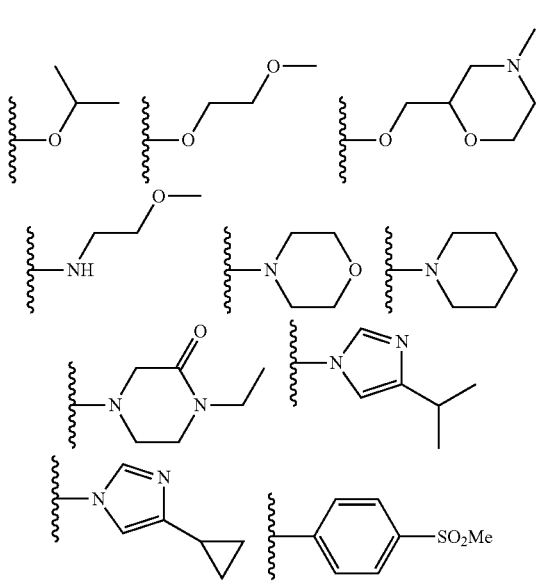

-continued

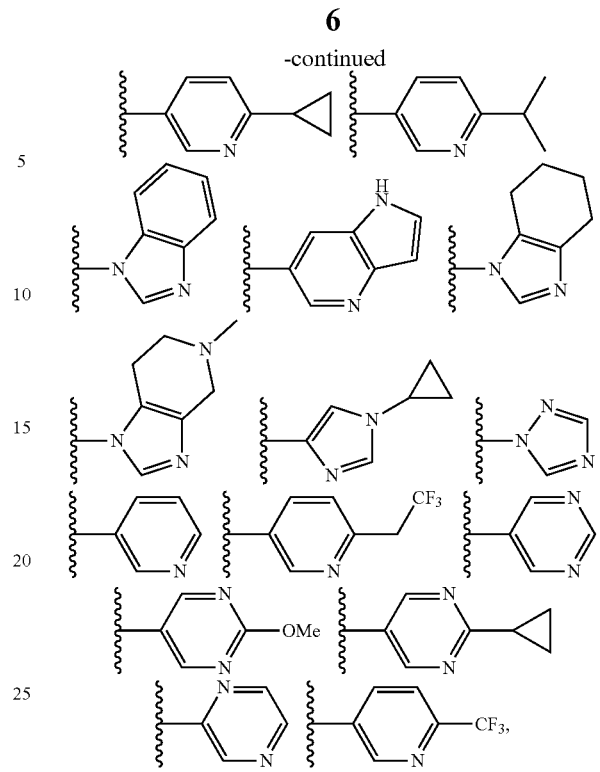

wherein each of the above shown groups is optionally substituted.

In certain embodiments, the present invention relates to compounds of Formula (I), and pharmaceutically acceptable salt, ester and combination thereof, wherein $R_5$ is selected from:

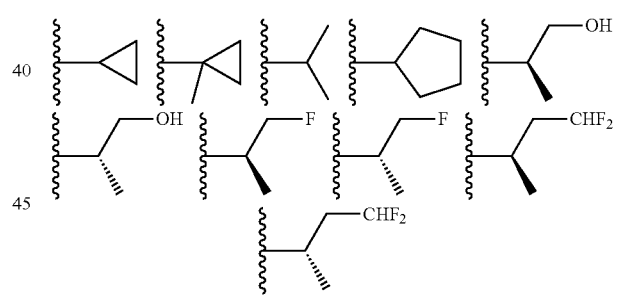

wherein each of the above shown groups is optionally substituted.

In one embodiment of the invention is represented by Formula (II) or a pharmaceutically acceptable salt, ester, or combination thereof:

(II)

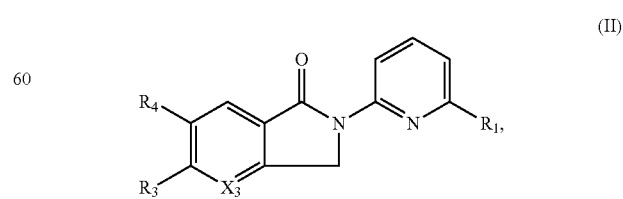

wherein $R_1$, $R_3$, $R_4$ and $X_3$ are as previously defined.

In another embodiment of the invention is represented by Formula (Ma) or Formula (IIIb), or a pharmaceutically acceptable salt, or ester, or combination thereof:

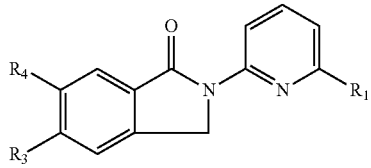

(IIIa)

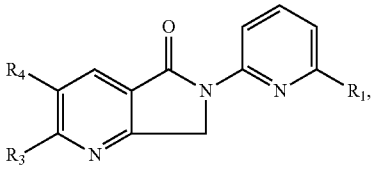

(IIIb)

wherein $R_1$, $R_3$, and $R_4$ are as previously defined.

In another embodiment of the invention is represented by Formula (IVa) or (IVb), or a pharmaceutically acceptable salt, or combination thereof:

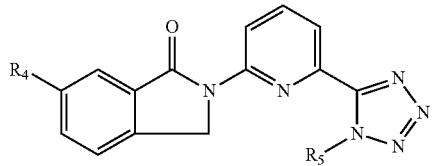

(IVa)

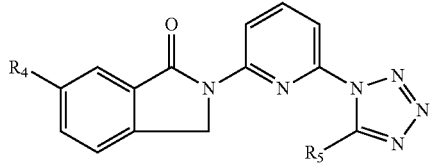

(IVb)

wherein $R_4$ and $R_5$ are as previously defined.

In another embodiment of the invention is represented by Formula (Va) or (Vb), or a pharmaceutically acceptable salt, or combination thereof:

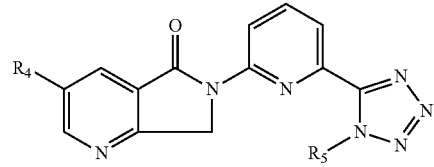

(Va)

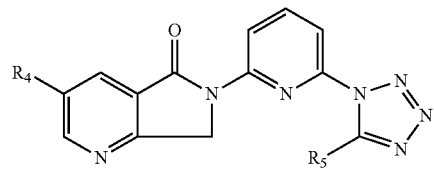

(Vb)

wherein $R_4$ and $R_5$ are as previously defined.

Representative compounds of the invention include, but are not limited to, the following compounds (compound 1 to compound 100 in Table 1) according to Formula (IVa), and pharmaceutically acceptable salts, esters and combinations thereof, wherein $R_4$ and $R_5$ are delineated for each compound in Table 1.

TABLE 1

| compound | $R_5$ | $R_4$ |
| --- | --- | --- |
| 1 | cyclopropyl | —O—iPr |
| 2 | 1-methylcyclopropyl | —O—iPr |
| 3 | isopropyl | —O—iPr |
| 4 | cyclopentylmethyl | —O—iPr |
| 5 | (S)-CH(CH₃)CH₂OH | —O—iPr |
| 6 | (R)-CH(CH₃)CH₂OH | —O—iPr |
| 7 | (S)-CH(CH₃)CH₂F | —O—iPr |
| 8 | (R)-CH(CH₃)CH₂F | —O—iPr |
| 9 | (S)-CH(CH₃)CHF₂ | —O—iPr |
| 10 | (R)-CH(CH₃)CHF₂ | —O—iPr |

TABLE 1-continued
| compound | R₅ | R₄ |
|---|---|---|
| 11 |  | 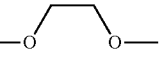 |
| 12 |  | 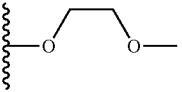 [SMILES: *OCCOC] |
| 13 |  | 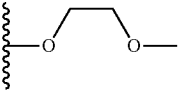 |
| 14 |  | 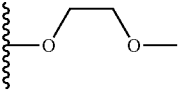 |
| 15 |  | 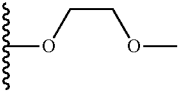 |
| 16 |  | 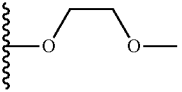 |
| 17 |  | 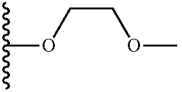 [SMILES: *OCCOC] |
| 18 |  | 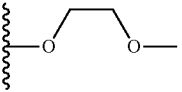 [SMILES: *OCCOC] |
| 19 |  | 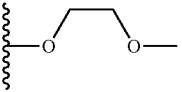 [SMILES: *OCCOC] |
| 20 |  | 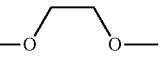 |
| 21 |  | 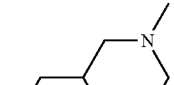 |
| 22 |  |  |
| 23 |  | 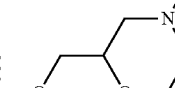 |
| 24 |  | 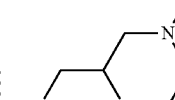 |
| 25 |  |  |
| 26 |  | 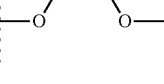 |
| 27 |  | 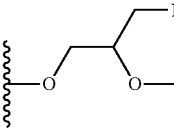 |
| 28 |  |  |
| 29 |  | 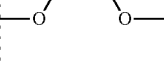 |
| 30 |  | 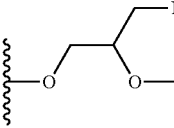 |
| 31 |  | 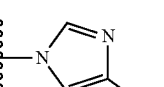 |

TABLE 1-continued

| compound | R₅ | R₄ |
|---|---|---|
| 32 | 1-methylcyclopropyl | 4-cyclopropyl-1H-imidazol-1-yl |
| 33 | isopropyl | 4-cyclopropyl-1H-imidazol-1-yl |
| 34 | cyclopentyl | 4-cyclopropyl-1H-imidazol-1-yl |
| 35 | (S)-2-methyl-3-hydroxypropyl | 4-cyclopropyl-1H-imidazol-1-yl |
| 36 | (R)-2-methyl-3-hydroxypropyl | 4-cyclopropyl-1H-imidazol-1-yl |
| 37 | (S)-3-fluoro-2-methylpropyl | 4-cyclopropyl-1H-imidazol-1-yl |
| 38 | (R)-3-fluoro-2-methylpropyl | 4-cyclopropyl-1H-imidazol-1-yl |
| 39 | (S)-1-(difluoromethyl)ethyl | 4-cyclopropyl-1H-imidazol-1-yl |
| 40 | (R)-1-(difluoromethyl)ethyl | 4-cyclopropyl-1H-imidazol-1-yl |
| 41 | cyclopropyl | morpholin-4-yl |
| 42 | 1-methylcyclopropyl | morpholin-4-yl |
| 43 | isopropyl | morpholin-4-yl |
| 44 | cyclopentyl | morpholin-4-yl |
| 45 | (S)-2-methyl-3-hydroxypropyl | morpholin-4-yl |
| 46 | (R)-2-methyl-3-hydroxypropyl | morpholin-4-yl |
| 47 | (S)-3-fluoro-2-methylpropyl | morpholin-4-yl |
| 48 | (R)-3-fluoro-2-methylpropyl | morpholin-4-yl |
| 49 | (S)-1-(difluoromethyl)ethyl | morpholin-4-yl |
| 50 | (R)-1-(difluoromethyl)ethyl | morpholin-4-yl |
| 51 | cyclopropyl | piperidin-1-yl |
| 52 | 1-methylcyclopropyl | piperidin-1-yl |
| 53 | isopropyl | piperidin-1-yl |
| 54 | cyclopentyl | piperidin-1-yl |
| 55 | (S)-2-methyl-3-hydroxypropyl | piperidin-1-yl |
| 56 | (R)-2-methyl-3-hydroxypropyl | piperidin-1-yl |

TABLE 1-continued

| compound | R₅ | R₄ |
|---|---|---|
| 57 | CH₂F, CH₃ (wedge) | piperidine (N) |
| 58 | CH₂F, CH₃ (dash) | piperidine (N) |
| 59 | CHF₂, CH₃ (wedge) | piperidine (N) |
| 60 | CHF₂, CH₃ (dash) | piperidine (N) |
| 61 | cyclopropyl | 4-ethyl-3-oxopiperazin-1-yl |
| 62 | 1-methylcyclopropyl | 4-ethyl-3-oxopiperazin-1-yl |
| 63 | isopropyl | 4-ethyl-3-oxopiperazin-1-yl |
| 64 | cyclopentyl | 4-ethyl-3-oxopiperazin-1-yl |
| 65 | CH₂OH, CH₃ (wedge) | 4-ethyl-3-oxopiperazin-1-yl |
| 66 | CH₂OH, CH₃ (dash) | 4-ethyl-3-oxopiperazin-1-yl |
| 67 | CH₂F, CH₃ (wedge) | 4-ethyl-3-oxopiperazin-1-yl |

TABLE 1-continued

| compound | R₅ | R₄ |
|---|---|---|
| 68 | CH₂F, CH₃ (dash) | 4-ethyl-3-oxopiperazin-1-yl |
| 69 | CHF₂, CH₃ (wedge) | 4-ethyl-3-oxopiperazin-1-yl |
| 70 | CHF₂, CH₃ (dash) | 4-ethyl-3-oxopiperazin-1-yl |
| 71 | cyclopropyl | 4-cyclopropyl-1H-imidazol-1-yl |
| 72 | 1-methylcyclopropyl | 4-cyclopropyl-1H-imidazol-1-yl |
| 73 | isopropyl | 4-cyclopropyl-1H-imidazol-1-yl |
| 74 | cyclopentyl | 4-cyclopropyl-1H-imidazol-1-yl |
| 75 | CH₂OH, CH₃ (wedge) | 4-cyclopropyl-1H-imidazol-1-yl |
| 76 | CH₂OH, CH₃ (dash) | 4-cyclopropyl-1H-imidazol-1-yl |
| 77 | CH₂F, CH₃ (wedge) | 4-cyclopropyl-1H-imidazol-1-yl |

TABLE 1-continued

| compound | R₅ | R₄ |
|---|---|---|
| 78 | CH₂F, methyl (stereo) | N-cyclopropyl imidazole (1-position) |
| 79 | CHF₂, methyl (stereo) | N-cyclopropyl imidazole (1-position) |
| 80 | CHF₂, methyl (stereo) | N-cyclopropyl imidazole (4-position) |
| 81 | cyclopropyl | 2-cyclopropylpyridin-5-yl |
| 82 | 1-methylcyclopropyl | 2-cyclopropylpyridin-5-yl |
| 83 | isopropyl | 2-cyclopropylpyridin-5-yl |
| 84 | cyclopentyl | 2-cyclopropylpyridin-5-yl |
| 85 | CH₂OH, methyl (stereo) | 2-cyclopropylpyridin-5-yl |
| 86 | CH₂OH, methyl (stereo) | 2-cyclopropylpyridin-5-yl |
| 87 | CH₂F, methyl (stereo) | 2-cyclopropylpyridin-5-yl |
| 88 | CH₂F, methyl (stereo) | 2-cyclopropylpyridin-5-yl |
| 89 | CHF₂, methyl (stereo) | 2-cyclopropylpyridin-5-yl |
| 90 | CHF₂, methyl (stereo) | 2-cyclopropylpyridin-5-yl |

TABLE 1-continued

| compound | R₅ | R₄ |
|---|---|---|
| 91 | cyclopropyl | 5-methyl-4,5,6,7-tetrahydroimidazo[4,5-c]pyridine |
| 92 | 1-methylcyclopropyl | 5-methyl-4,5,6,7-tetrahydroimidazo[4,5-c]pyridine |
| 93 | isopropyl | 5-methyl-4,5,6,7-tetrahydroimidazo[4,5-c]pyridine |
| 94 | cyclopentyl | 5-methyl-4,5,6,7-tetrahydroimidazo[4,5-c]pyridine |
| 95 | CH₂OH, methyl (stereo) | 5-methyl-4,5,6,7-tetrahydroimidazo[4,5-c]pyridine |
| 96 | CH₂OH, methyl (stereo) | 5-methyl-4,5,6,7-tetrahydroimidazo[4,5-c]pyridine |
| 97 | CH₂F, methyl (stereo) | 5-methyl-4,5,6,7-tetrahydroimidazo[4,5-c]pyridine |
| 98 | CH₂F, methyl (stereo) | 5-methyl-4,5,6,7-tetrahydroimidazo[4,5-c]pyridine |

TABLE 1-continued

| compound | R$_5$ | R$_4$ |
|---|---|---|
| 99 | CHF$_2$ (R) | N-methyl tetrahydroimidazopyridine |
| 100 | CHF$_2$ (S) | N-methyl tetrahydroimidazopyridine |

Representative compounds of the invention include, but are not limited to, the following compounds (compound 101 to compound 200 in Table 2) according to Formula (IVb), and pharmaceutically acceptable salts, esters and combinations thereof, wherein R$_4$ and R$_5$ are delineated for each compound in Table 2.

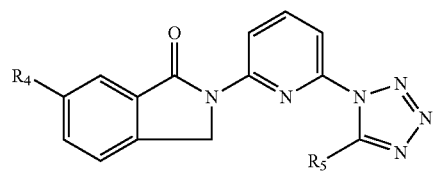

(IVb)

TABLE 2

| compound | R$_5$ | R$_4$ |
|---|---|---|
| 101 | cyclopropyl | —O-iPr |
| 102 | 1-methylcyclopropyl | —O-iPr |
| 103 | isopropyl | —O-iPr |
| 104 | cyclopentyl | —O-iPr |
| 105 | CH$_2$OH (R) | —O-iPr |
| 106 | CH$_2$OH (S) | —O-iPr |

TABLE 2-continued

| compound | R$_5$ | R$_4$ |
|---|---|---|
| 107 | CH$_2$F (R) | —O-iPr |
| 108 | CH$_2$F (S) | —O-iPr |
| 109 | CHF$_2$ (R) | —O-iPr |
| 110 | CHF$_2$ (S) | —O-iPr |
| 111 | cyclopropyl | —OCH$_2$CH$_2$O— |
| 112 | 1-methylcyclopropyl | —OCH$_2$CH$_2$O— |
| 113 | isopropyl | —OCH$_2$CH$_2$O— |
| 114 | cyclopentyl | —OCH$_2$CH$_2$O— |
| 115 | CH$_2$OH (R) | —OCH$_2$CH$_2$O— |
| 116 | CH$_2$OH (S) | —OCH$_2$CH$_2$O— |
| 117 | CH$_2$F (R) | —OCH$_2$CH$_2$O— |
| 118 | CH$_2$F (S) | —OCH$_2$CH$_2$O— |
| 119 | CHF$_2$ (R) | —OCH$_2$CH$_2$O— |
| 120 | CHF$_2$ (S) | —OCH$_2$CH$_2$O— |

TABLE 2-continued
| compound | R5 | R4 |
|---|---|---|
| 121 |  | 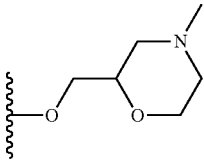 [SMILES: *OCC1CN(C)CCO1] |
| 122 |  | 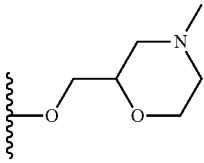 [SMILES: *OCC1CN(C)CCO1] |
| 123 |  | 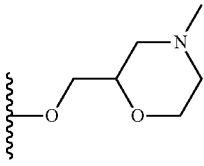 [SMILES: *OCC1CN(C)CCO1] |
| 124 | 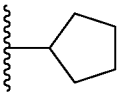 | 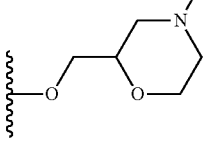 |
| 125 | 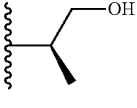 [SMILES: *[C@H](C)CO] | 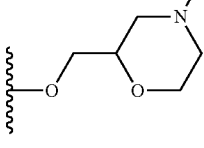 |
| 126 | 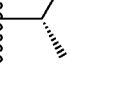 | 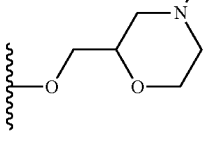 |
| 127 | 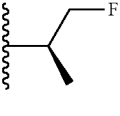 [SMILES: *[C@H](C)CF] | 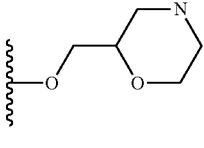 |
| 128 |  | 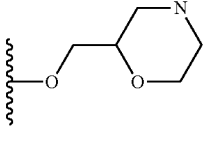 |
| 129 | 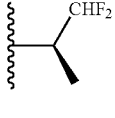 | 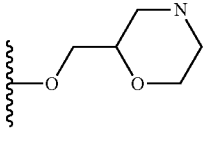 |
TABLE 2-continued
| compound | R5 | R4 |
|---|---|---|
| 130 | 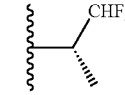 | 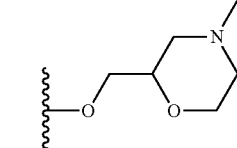 |
| 131 |  | 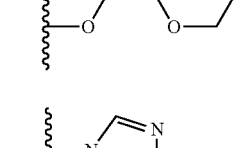 |
| 132 | 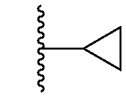 | 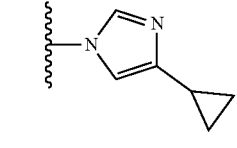 [SMILES: *n1cnc(C2CC2)c1] |
| 133 | 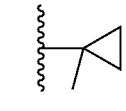 | 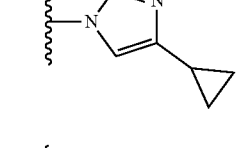 |
| 134 |  | 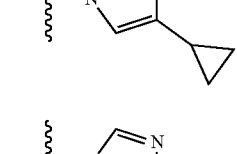 |
| 135 | 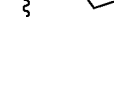 | 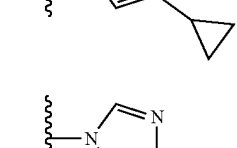 |
| 136 | 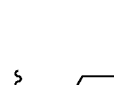 | 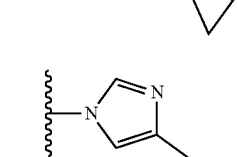 |
| 137 | 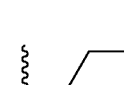 | 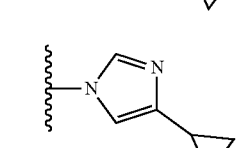 |
| 138 | 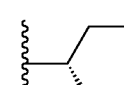 | 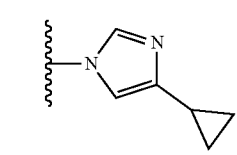 [SMILES: *n1cnc(C2CC2)c1] |
| 139 | 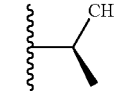 | 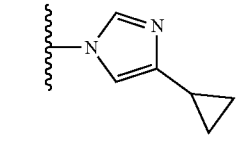 [SMILES: *n1cnc(C2CC2)c1] |

TABLE 2-continued

| compound | R₅ | R₄ |
|---|---|---|
| 140 | CHF₂, methyl (stereo) | imidazole-N with cyclopropyl |
| 141 | cyclopropyl | morpholine-N |
| 142 | 1-methylcyclopropyl | morpholine-N |
| 143 | isopropyl | morpholine-N |
| 144 | cyclopentyl | morpholine-N |
| 145 | CH₂OH, methyl (stereo) | morpholine-N |
| 146 | CH₂OH, methyl (stereo) | morpholine-N |
| 147 | CH₂F, methyl (stereo) | morpholine-N |
| 148 | CH₂F, methyl (stereo) | morpholine-N |
| 149 | CHF₂, methyl (stereo) | morpholine-N |
| 150 | CHF₂, methyl (stereo) | morpholine-N |
| 151 | cyclopropyl | piperidine-N |
| 152 | 1-methylcyclopropyl | piperidine-N |
| 153 | isopropyl | piperidine-N |
| 154 | cyclopentyl | piperidine-N |
| 155 | CH₂OH, methyl (stereo) | piperidine-N |
| 156 | CH₂OH, methyl (stereo) | piperidine-N |
| 157 | CH₂F, methyl (stereo) | piperidine-N |
| 158 | CH₂F, methyl (stereo) | piperidine-N |
| 159 | CHF₂, methyl (stereo) | piperidine-N |
| 160 | CHF₂, methyl (stereo) | piperidine-N |
| 161 | cyclopropyl | 4-ethyl-3-oxopiperazin-1-yl |
| 162 | 1-methylcyclopropyl | 4-ethyl-3-oxopiperazin-1-yl |
| 163 | isopropyl | 4-ethyl-3-oxopiperazin-1-yl |
| 164 | cyclopentyl | 4-ethyl-3-oxopiperazin-1-yl |
| 165 | CH₂OH, methyl (stereo) | 4-ethyl-3-oxopiperazin-1-yl |

TABLE 2-continued

| compound | R5 | R4 |
|---|---|---|
| 166 | (S)-CH(CH3)CH2OH | 4-ethyl-3-oxopiperazin-1-yl |
| 167 | (S)-CH(CH3)CH2F | 4-ethyl-3-oxopiperazin-1-yl |
| 168 | (R)-CH(CH3)CH2F | 4-ethyl-3-oxopiperazin-1-yl |
| 169 | (S)-CH(CH3)CHF2 | 4-ethyl-3-oxopiperazin-1-yl |
| 170 | (R)-CH(CH3)CHF2 | 4-ethyl-3-oxopiperazin-1-yl |
| 171 | cyclopropyl | 1-cyclopropyl-1H-imidazol-4-yl |
| 172 | 1-methylcyclopropyl | 1-cyclopropyl-1H-imidazol-4-yl |
| 173 | isopropyl | 1-cyclopropyl-1H-imidazol-4-yl |
| 174 | cyclopentyl | 1-cyclopropyl-1H-imidazol-4-yl |
| 175 | (S)-CH(CH3)CH2OH | 1-cyclopropyl-1H-imidazol-4-yl |
| 176 | (R)-CH(CH3)CH2OH | 1-cyclopropyl-1H-imidazol-4-yl |
| 177 | (S)-CH(CH3)CH2F | 1-cyclopropyl-1H-imidazol-4-yl |
| 178 | (R)-CH(CH3)CH2F | 1-cyclopropyl-1H-imidazol-4-yl |
| 179 | (S)-CH(CH3)CHF2 | 1-cyclopropyl-1H-imidazol-4-yl |
| 180 | (R)-CH(CH3)CHF2 | 1-cyclopropyl-1H-imidazol-4-yl |
| 181 | cyclopropyl | 6-cyclopropylpyridin-3-yl |
| 182 | 1-methylcyclopropyl | 6-cyclopropylpyridin-3-yl |
| 183 | isopropyl | 6-cyclopropylpyridin-3-yl |
| 184 | cyclopentyl | 6-cyclopropylpyridin-3-yl |
| 185 | (S)-CH(CH3)CH2OH | 6-cyclopropylpyridin-3-yl |
| 186 | (R)-CH(CH3)CH2OH | 6-cyclopropylpyridin-3-yl |
| 187 | (S)-CH(CH3)CH2F | 6-cyclopropylpyridin-3-yl |

TABLE 2-continued

| compound | R5 | R4 |
|---|---|---|
| 188 | CH2F (S-methyl) | 6-cyclopropylpyridin-3-yl |
| 189 | CHF2 (R-methyl) | 6-cyclopropylpyridin-3-yl |
| 190 | CHF2 (S-methyl) | 5-cyclopropylpyridin-2-yl |
| 191 | cyclopropyl | 5-methyl-4,5,6,7-tetrahydro-1H-imidazo[4,5-c]pyridin-1-yl |
| 192 | 1-methylcyclopropyl | 5-methyl-4,5,6,7-tetrahydro-1H-imidazo[4,5-c]pyridin-1-yl |
| 193 | isopropyl | 5-methyl-4,5,6,7-tetrahydro-1H-imidazo[4,5-c]pyridin-1-yl |
| 194 | cyclopentyl | 5-methyl-4,5,6,7-tetrahydro-1H-imidazo[4,5-c]pyridin-1-yl |
| 195 | CH2OH (R-methyl) | 5-methyl-4,5,6,7-tetrahydro-1H-imidazo[4,5-c]pyridin-1-yl |
| 196 | CH2OH (S-methyl) | 5-methyl-4,5,6,7-tetrahydro-1H-imidazo[4,5-c]pyridin-1-yl |
| 197 | CH2F (R-methyl) | 5-methyl-4,5,6,7-tetrahydro-1H-imidazo[4,5-c]pyridin-1-yl |
| 198 | CH2F (S-methyl) | 5-methyl-4,5,6,7-tetrahydro-1H-imidazo[4,5-c]pyridin-1-yl |
| 199 | CHF2 (R-methyl) | 5-methyl-4,5,6,7-tetrahydro-1H-imidazo[4,5-c]pyridin-1-yl |
| 200 | CHF2 (S-methyl) | 5-methyl-4,5,6,7-tetrahydro-1H-imidazo[4,5-c]pyridin-1-yl |

Representative compounds of the invention include, but are not limited to, the following compounds (compound 201 to compound 300 in Table 3) according to Formula (Va), and pharmaceutically acceptable salts, esters and combinations thereof, wherein $R_4$ and $R_5$ are delineated for each compound in Table 3.

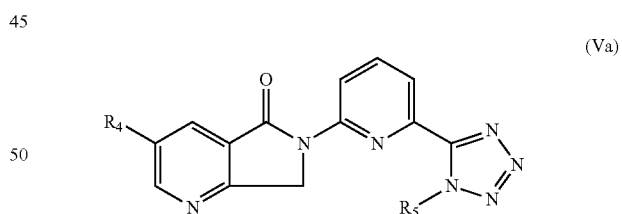

(Va)

TABLE 3

| compound | R5 | R4 |
|---|---|---|
| 201 | cyclopropyl | O-isopropyl |
| 202 | 1-methylcyclopropyl | O-isopropyl |

TABLE 3-continued

| compound | R₅ | R₄ |
|---|---|---|
| 203 | isopropyl | O-isopropyl |
| 204 | cyclopentyl | O-isopropyl |
| 205 | CH(CH₃)CH₂OH | O-isopropyl |
| 206 | CH(CH₃)CH₂OH | O-isopropyl |
| 207 | CH(CH₃)CH₂F | O-isopropyl |
| 208 | CH(CH₃)CH₂F | O-isopropyl |
| 209 | CH(CH₃)CHF₂ | O-isopropyl |
| 210 | CH(CH₃)CHF₂ | O-isopropyl |
| 211 | cyclopropyl | OCH₂CH₂OCH₃ |
| 212 | 1-methylcyclopropyl | OCH₂CH₂OCH₃ |
| 213 | isopropyl | OCH₂CH₂OCH₃ |
| 214 | cyclopentyl | OCH₂CH₂OCH₃ |
| 215 | CH(CH₃)CH₂OH | OCH₂CH₂OCH₃ |
| 216 | CH(CH₃)CH₂OH | OCH₂CH₂OCH₃ |
| 217 | CH(CH₃)CH₂F | OCH₂CH₂OCH₃ |
| 218 | CH(CH₃)CH₂F | OCH₂CH₂OCH₃ |
| 219 | CH(CH₃)CHF₂ | OCH₂CH₂OCH₃ |
| 220 | CH(CH₃)CHF₂ | OCH₂CH₂OCH₃ |
| 221 | cyclopropyl | (4-methylmorpholin-2-yl)methoxy |
| 222 | 1-methylcyclopropyl | (4-methylmorpholin-2-yl)methoxy |
| 223 | isopropyl | (4-methylmorpholin-2-yl)methoxy |
| 224 | cyclopentyl | (4-methylmorpholin-2-yl)methoxy |
| 225 | CH(CH₃)CH₂OH | (4-methylmorpholin-2-yl)methoxy |
| 226 | CH(CH₃)CH₂OH | (4-methylmorpholin-2-yl)methoxy |

TABLE 3-continued

| compound | R₅ | R₄ |
|---|---|---|
| 227 | CH₂F, CH₃ (R) | N-methylmorpholine-CH₂O- |
| 228 | CH₂F, CH₃ (S) | N-methylmorpholine-CH₂O- |
| 229 | CHF₂, CH₃ (R) | N-methylmorpholine-CH₂O- |
| 230 | CHF₂, CH₃ (S) | N-methylmorpholine-CH₂O- |
| 231 | cyclopropyl | 4-cyclopropyl-imidazol-1-yl |
| 232 | 1-methylcyclopropyl | 4-cyclopropyl-imidazol-1-yl |
| 233 | isopropyl | 4-cyclopropyl-imidazol-1-yl |
| 234 | cyclopentyl | 4-cyclopropyl-imidazol-1-yl |
| 235 | CH₂OH, CH₃ (R) | 4-cyclopropyl-imidazol-1-yl |
| 236 | CH₂OH, CH₃ (S) | 4-cyclopropyl-imidazol-1-yl |
| 237 | CH₂F, CH₃ (R) | 4-cyclopropyl-imidazol-1-yl |
| 238 | CH₂F, CH₃ (S) | 4-cyclopropyl-imidazol-1-yl |
| 239 | CHF₂, CH₃ (R) | 4-cyclopropyl-imidazol-1-yl |
| 240 | CHF₂, CH₃ (S) | 4-cyclopropyl-imidazol-1-yl |
| 241 | cyclopropyl | morpholin-4-yl |
| 242 | 1-methylcyclopropyl | morpholin-4-yl |
| 243 | isopropyl | morpholin-4-yl |
| 244 | cyclopentyl | morpholin-4-yl |
| 245 | CH₂OH, CH₃ (R) | morpholin-4-yl |
| 246 | CH₂OH, CH₃ (S) | morpholin-4-yl |
| 247 | CH₂F, CH₃ (R) | morpholin-4-yl |
| 248 | CH₂F, CH₃ (S) | morpholin-4-yl |
| 249 | CHF₂, CH₃ (R) | morpholin-4-yl |

TABLE 3-continued

| compound | R₅ | R₄ |
|---|---|---|
| 250 | CH(CHF₂)(CH₃)- (R) | morpholin-4-yl |
| 251 | cyclopropyl | piperidin-1-yl |
| 252 | 1-methylcyclopropyl | piperidin-1-yl |
| 253 | isopropyl | piperidin-1-yl |
| 254 | cyclopentyl | piperidin-1-yl |
| 255 | CH(CH₂OH)(CH₃)- (R) | piperidin-1-yl |
| 256 | CH(CH₂OH)(CH₃)- (S) | piperidin-1-yl |
| 257 | CH(CH₂F)(CH₃)- (R) | piperidin-1-yl |
| 258 | CH(CH₂F)(CH₃)- (S) | piperidin-1-yl |
| 259 | CH(CHF₂)(CH₃)- (R) | piperidin-1-yl |
| 260 | CH(CHF₂)(CH₃)- (S) | piperidin-1-yl |
| 261 | cyclopropyl | 4-ethyl-3-oxopiperazin-1-yl |
| 262 | 1-methylcyclopropyl | 4-ethyl-3-oxopiperazin-1-yl |
| 263 | isopropyl | 4-ethyl-3-oxopiperazin-1-yl |
| 264 | cyclopentyl | 4-ethyl-3-oxopiperazin-1-yl |
| 265 | CH(CH₂OH)(CH₃)- (R) | 4-ethyl-3-oxopiperazin-1-yl |
| 266 | CH(CH₂OH)(CH₃)- (S) | 4-ethyl-3-oxopiperazin-1-yl |
| 267 | CH(CH₂F)(CH₃)- (R) | 4-ethyl-3-oxopiperazin-1-yl |
| 268 | CH(CH₂F)(CH₃)- (S) | 4-ethyl-3-oxopiperazin-1-yl |
| 269 | CH(CHF₂)(CH₃)- (R) | 4-ethyl-3-oxopiperazin-1-yl |
| 270 | CH(CHF₂)(CH₃)- (S) | 4-ethyl-3-oxopiperazin-1-yl |
| 271 | cyclopropyl | 1-cyclopropyl-1H-imidazol-4-yl |
| 272 | 1-methylcyclopropyl | 1-cyclopropyl-1H-imidazol-4-yl |

TABLE 3-continued

| compound | R₅ | R₄ |
| --- | --- | --- |
| 273 | isopropyl | 1-cyclopropyl-imidazol-4-yl |
| 274 | cyclopentyl | 1-cyclopropyl-imidazol-4-yl |
| 275 | (S)-2-methyl-3-hydroxypropyl | 1-cyclopropyl-imidazol-4-yl |
| 276 | (R)-2-methyl-3-hydroxypropyl | 1-cyclopropyl-imidazol-4-yl |
| 277 | (S)-2-methyl-3-fluoropropyl | 1-cyclopropyl-imidazol-4-yl |
| 278 | (R)-2-methyl-3-fluoropropyl | 1-cyclopropyl-imidazol-4-yl |
| 279 | (S)-1-(difluoromethyl)ethyl | 1-cyclopropyl-imidazol-4-yl |
| 280 | (R)-1-(difluoromethyl)ethyl | 1-cyclopropyl-imidazol-4-yl |
| 281 | cyclopropyl | 6-cyclopropyl-pyridin-3-yl |
| 282 | 1-methylcyclopropyl | 6-cyclopropyl-pyridin-3-yl |
| 283 | isobutyl | 6-cyclopropyl-pyridin-3-yl |
| 284 | cyclopentyl | 6-cyclopropyl-pyridin-3-yl |
| 285 | (S)-2-methyl-3-hydroxypropyl | 6-cyclopropyl-pyridin-3-yl |
| 286 | (R)-2-methyl-3-hydroxypropyl | 6-cyclopropyl-pyridin-3-yl |
| 287 | (S)-2-methyl-3-fluoropropyl | 6-cyclopropyl-pyridin-3-yl |
| 288 | (R)-2-methyl-3-fluoropropyl | 6-cyclopropyl-pyridin-3-yl |
| 289 | (S)-1-(difluoromethyl)ethyl | 6-cyclopropyl-pyridin-3-yl |
| 290 | (R)-1-(difluoromethyl)ethyl | 6-cyclopropyl-pyridin-3-yl |
| 291 | cyclopropyl | 5-methyl-4,5,6,7-tetrahydroimidazo[4,5-c]pyridin-1-yl |
| 292 | 1-methylcyclopropyl | 5-methyl-4,5,6,7-tetrahydroimidazo[4,5-c]pyridin-1-yl |
| 293 | isopropyl | 5-methyl-4,5,6,7-tetrahydroimidazo[4,5-c]pyridin-1-yl |
| 294 | cyclopentyl | 5-methyl-4,5,6,7-tetrahydroimidazo[4,5-c]pyridin-1-yl |

TABLE 3-continued

| compound | R5 | R4 |
|---|---|---|
| 295 | CH2OH, (S)-methyl | N-methyl-tetrahydroimidazo-pyridine |
| 296 | CH2OH, (R)-methyl | N-methyl-tetrahydroimidazo-pyridine |
| 297 | CH2F, (S)-methyl | N-methyl-tetrahydroimidazo-pyridine |
| 298 | CH2F, (R)-methyl | N-methyl-tetrahydroimidazo-pyridine |
| 299 | CHF2, (S)-methyl | N-methyl-tetrahydroimidazo-pyridine |
| 300 | CHF2, (R)-methyl | N-methyl-tetrahydroimidazo-pyridine |

Representative compounds of the invention include, but are not limited to, the following compounds (compound 301 to compound 400 in Table 4) according to Formula (Vb), and pharmaceutically acceptable salts, esters and combinations thereof, wherein $R_4$ and $R_5$ are delineated for each compound in Table 4.

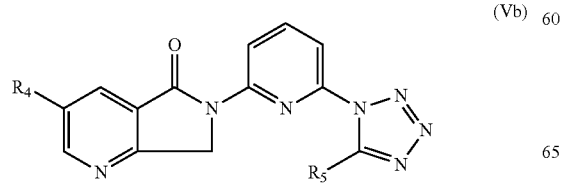
(Vb)

TABLE 4

| compound | R5 | R4 |
|---|---|---|
| 301 | cyclopropyl | O-isopropyl |
| 302 | 1-methylcyclopropyl | O-isopropyl |
| 303 | isopropyl | O-isopropyl |
| 304 | cyclopentyl | O-isopropyl |
| 305 | CH2OH, (S)-methyl | O-isopropyl |
| 306 | CH2OH, (R)-methyl | O-isopropyl |
| 307 | CH2F, (S)-methyl | O-isopropyl |
| 308 | CH2F, (R)-methyl | O-isopropyl |
| 309 | CHF2, (S)-methyl | O-isopropyl |
| 310 | CHF2, (R)-methyl | O-isopropyl |
| 311 | cyclopropyl | OCH2CH2OCH3 |
| 312 | 1-methylcyclopropyl | OCH2CH2OCH3 |
| 313 | isopropyl | OCH2CH2OCH3 |
| 314 | cyclopentyl | OCH2CH2OCH3 |

TABLE 4-continued

| compound | R₅ | R₄ |
|---|---|---|
| 315 | (S)-CH(CH₃)CH₂OH | -O-CH₂-O-CH₃ (ethylene glycol methyl ether) |
| 316 | (R)-CH(CH₃)CH₂OH | -O-CH₂-O-CH₃ |
| 317 | (S)-CH(CH₃)CH₂F | -O-CH₂-O-CH₃ |
| 318 | (R)-CH(CH₃)CH₂F | -O-CH₂-O-CH₃ |
| 319 | (S)-CH(CH₃)CHF₂ | -O-CH₂-O-CH₃ |
| 320 | (R)-CH(CH₃)CHF₂ | -O-CH₂-O-CH₃ |
| 321 | cyclopropyl | (4-methylmorpholin-2-yl)methoxy |
| 322 | 1-methylcyclopropyl | (4-methylmorpholin-2-yl)methoxy |
| 323 | isopropyl | (4-methylmorpholin-2-yl)methoxy |
| 324 | cyclopentyl | (4-methylmorpholin-2-yl)methoxy |
| 325 | (S)-CH(CH₃)CH₂OH | (4-methylmorpholin-2-yl)methoxy |
| 326 | (R)-CH(CH₃)CH₂OH | (4-methylmorpholin-2-yl)methoxy |
| 327 | (S)-CH(CH₃)CH₂F | (4-methylmorpholin-2-yl)methoxy |
| 328 | (R)-CH(CH₃)CH₂F | (4-methylmorpholin-2-yl)methoxy |
| 329 | (S)-CH(CH₃)CHF₂ | (4-methylmorpholin-2-yl)methoxy |
| 330 | (R)-CH(CH₃)CHF₂ | (4-methylmorpholin-2-yl)methoxy |
| 331 | cyclopropyl | 4-cyclopropyl-1H-imidazol-1-yl |
| 332 | 1-methylcyclopropyl | 4-cyclopropyl-1H-imidazol-1-yl |
| 333 | isopropyl | 4-cyclopropyl-1H-imidazol-1-yl |
| 334 | cyclopentyl | 4-cyclopropyl-1H-imidazol-1-yl |
| 335 | (S)-CH(CH₃)CH₂OH | 4-cyclopropyl-1H-imidazol-1-yl |

TABLE 4-continued

| compound | R5 | R4 |
|---|---|---|
| 336 | CH(CH3)CH2OH | 4-cyclopropyl-imidazol-1-yl |
| 337 | CH(CH3)CH2F | 4-cyclopropyl-imidazol-1-yl |
| 338 | CH(CH3)CH2F | 4-cyclopropyl-imidazol-1-yl |
| 339 | CH(CH3)CHF2 | 4-cyclopropyl-imidazol-1-yl |
| 340 | CH(CH3)CHF2 | 4-cyclopropyl-imidazol-1-yl |
| 341 | cyclopropyl | morpholin-4-yl |
| 342 | 1-methylcyclopropyl | morpholin-4-yl |
| 343 | isopropyl | morpholin-4-yl |
| 344 | cyclopentyl | morpholin-4-yl |
| 345 | CH(CH3)CH2OH | morpholin-4-yl |
| 346 | CH(CH3)CH2OH | morpholin-4-yl |
| 347 | CH(CH3)CH2F | morpholin-4-yl |
| 348 | CH(CH3)CH2F | morpholin-4-yl |
| 349 | CH(CH3)CHF2 | morpholin-4-yl |
| 350 | CH(CH3)CHF2 | morpholin-4-yl |
| 351 | cyclopropyl | piperidin-1-yl |
| 352 | 1-methylcyclopropyl | piperidin-1-yl |
| 353 | isopropyl | piperidin-1-yl |
| 354 | cyclopentyl | piperidin-1-yl |
| 355 | CH(CH3)CH2OH | piperidin-1-yl |
| 356 | CH(CH3)CH2OH | piperidin-1-yl |
| 357 | CH(CH3)CH2F | piperidin-1-yl |
| 358 | CH(CH3)CH2F | piperidin-1-yl |
| 359 | CH(CH3)CHF2 | piperidin-1-yl |
| 360 | CH(CH3)CHF2 | piperidin-1-yl |
| 361 | cyclopropyl | 4-ethyl-3-oxopiperazin-1-yl |

TABLE 4-continued

| compound | R5 | R4 |
|---|---|---|
| 362 | 1-methylcyclopropyl | N-ethyl-piperazinone |
| 363 | isopropyl | N-ethyl-piperazinone |
| 364 | cyclopentyl | N-ethyl-piperazinone |
| 365 | (S)-2-methyl-3-hydroxypropyl | N-ethyl-piperazinone |
| 366 | (R)-2-methyl-3-hydroxypropyl | N-ethyl-piperazinone |
| 367 | (S)-2-methyl-3-fluoropropyl | N-ethyl-piperazinone |
| 368 | (R)-2-methyl-3-fluoropropyl | N-ethyl-piperazinone |
| 369 | (S)-1-(difluoromethyl)ethyl | N-ethyl-piperazinone |
| 370 | (R)-1-(difluoromethyl)ethyl | N-ethyl-piperazinone |
| 371 | cyclopropyl | 1-cyclopropyl-imidazol-4-yl |
| 372 | 1-methylcyclopropyl | 1-cyclopropyl-imidazol-4-yl |

TABLE 4-continued

| compound | R5 | R4 |
|---|---|---|
| 373 | isopropyl | 1-cyclopropyl-imidazol-4-yl |
| 374 | cyclopentyl | 1-cyclopropyl-imidazol-4-yl |
| 375 | (S)-2-methyl-3-hydroxypropyl | 1-cyclopropyl-imidazol-4-yl |
| 376 | (R)-2-methyl-3-hydroxypropyl | 1-cyclopropyl-imidazol-4-yl |
| 377 | (S)-2-methyl-3-fluoropropyl | 1-cyclopropyl-imidazol-4-yl |
| 378 | (R)-2-methyl-3-fluoropropyl | 1-cyclopropyl-imidazol-4-yl |
| 379 | (S)-1-(difluoromethyl)ethyl | 1-cyclopropyl-imidazol-4-yl |
| 380 | (R)-1-(difluoromethyl)ethyl | 1-cyclopropyl-imidazol-4-yl |
| 381 | cyclopropyl | 6-cyclopropyl-pyridin-3-yl |
| 382 | 1-methylcyclopropyl | 6-cyclopropyl-pyridin-3-yl |
| 383 | isopropyl | 6-cyclopropyl-pyridin-3-yl |

TABLE 4-continued

| compound | R5 | R4 |
|---|---|---|
| 384 | cyclopentyl | 6-cyclopropylpyridin-3-yl |
| 385 | (S)-1-hydroxy-2-methylpropyl | 6-cyclopropylpyridin-3-yl |
| 386 | (R)-1-hydroxy-2-methylpropyl | 6-cyclopropylpyridin-3-yl |
| 387 | (S)-1-fluoro-2-methylpropyl | 6-cyclopropylpyridin-3-yl |
| 388 | (R)-1-fluoro-2-methylpropyl | 6-cyclopropylpyridin-3-yl |
| 389 | (S)-1-(difluoromethyl)ethyl | 6-cyclopropylpyridin-3-yl |
| 390 | (R)-1-(difluoromethyl)ethyl | 6-cyclopropylpyridin-3-yl |
| 391 | cyclopropylmethyl | 5-methyl-4,5,6,7-tetrahydro-1H-imidazo[4,5-c]pyridin-1-yl |
| 392 | 1-methylcyclopropyl | 5-methyl-4,5,6,7-tetrahydro-1H-imidazo[4,5-c]pyridin-1-yl |
| 393 | isopropyl | 5-methyl-4,5,6,7-tetrahydro-1H-imidazo[4,5-c]pyridin-1-yl |
| 394 | cyclopentyl | 5-methyl-4,5,6,7-tetrahydro-1H-imidazo[4,5-c]pyridin-1-yl |
| 395 | (S)-1-hydroxy-2-methylpropyl | 5-methyl-4,5,6,7-tetrahydro-1H-imidazo[4,5-c]pyridin-1-yl |
| 396 | (R)-1-hydroxy-2-methylpropyl | 5-methyl-4,5,6,7-tetrahydro-1H-imidazo[4,5-c]pyridin-1-yl |
| 397 | (S)-1-fluoro-2-methylpropyl | 5-methyl-4,5,6,7-tetrahydro-1H-imidazo[4,5-c]pyridin-1-yl |
| 398 | (R)-1-fluoro-2-methylpropyl | 5-methyl-4,5,6,7-tetrahydro-1H-imidazo[4,5-c]pyridin-1-yl |
| 399 | (S)-1-(difluoromethyl)ethyl | 5-methyl-4,5,6,7-tetrahydro-1H-imidazo[4,5-c]pyridin-1-yl |
| 400 | (R)-1-(difluoromethyl)ethyl | 5-methyl-4,5,6,7-tetrahydro-1H-imidazo[4,5-c]pyridin-1-yl |

In certain embodiments, the present invention provides a method for the prevention or treatment of an ASK-1 mediated disease or condition. The method comprises administering a therapeutically effective amount of a compound of Formula (I). The present invention also provides the use of a compound of Formula (I) for the preparation of a medicament for the prevention or treatment of an ASK-1 mediated disease or condition.

In certain embodiments, the ASK-1 mediated disease or condition is an autoimmune disorder, a neurodegenerative disorder, an inflammatory disease, chronic kidney disease, renal disease, cardiovascular disease, a metabolic disease, or an acute or chronic liver disease.

In certain embodiments, the chronic liver disease is primary biliary cirrhosis (PBC), cerebrotendinous xanthomatosis (CTX), primary sclerosing cholangitis (PSC), drug induced cholestasis, intrahepatic cholestasis of pregnancy, parenteral nutrition associated cholestasis (PNAC), bacterial overgrowth or sepsis associated cholestasis, autoimmune hepatitis, chronic viral hepatitis, alcoholic liver disease, nonalcoholic fatty liver disease (NAFLD), nonalcoholic steatohepatitis (NASH), liver transplant associated graft versus host disease, living donor transplant liver regeneration, congenital hepatic fibrosis, choledocholithiasis, granulomatous liver disease, intra- or extrahepatic malignancy, Sjogren's syndrome, Sarcoidosis, Wilson's disease, Gaucher's disease, hemochromatosis, or alpha 1-antitrypsin deficiency. In certain embodiments, the gastrointestinal disease is inflammatory bowel disease (IBD) (including Crohn's disease and ulcerative colitis), irritable bowel syndrome (IBS), bacterial overgrowth, malabsorption, post-radiation colitis, or microscopic colitis.

In certain embodiments, the renal disease is diabetic nephropathy, focal segmental glomerulosclerosis (FSGS), hypertensive nephrosclerosis, chronic glomerulonephritis, chronic transplant glomerulopathy, chronic interstitial nephritis, or polycystic kidney disease.

In certain embodiments, the cardiovascular disease is atherosclerosis, arteriosclerosis, dyslipidemia, hypercholesterolemia, or hypertriglyceridemia.

In certain embodiments, the metabolic disease is insulin resistance, Type I and Type II diabetes, or obesity.

Yet a further aspect of the present invention is a process of making any of the compounds delineated herein employing any of the synthetic means delineated herein.

Definitions

Listed below are definitions of various terms used to describe this invention. These definitions apply to the terms as they are used throughout this specification and claims, unless otherwise limited in specific instances, either individually or as part of a larger group.

The term "alkyl" as used herein, refers to saturated, straight- or branched-chain hydrocarbon radicals. "$C_1$-$C_3$ alkyl", "$C_1$-$C_6$ alkyl", "$C_1$-$C_{10}$ alkyl", "$C_2$-$C_4$ alkyl" or "$C_3$-$C_6$ alkyl", refer to alkyl groups containing from one to three, one to six, one to ten carbon atoms, 2 to 4 and 3 to 6 carbon atoms respectively. Examples of $C_1$-$C_8$ alkyl radicals include, but are not limited to, methyl, ethyl, propyl, isopropyl, n-butyl, tert-butyl, neopentyl, n-hexyl, heptyl and octyl radicals.

The term "alkenyl" as used herein, refers to straight- or branched-chain hydrocarbon radicals having at least one carbon-carbon double bond by the removal of a single hydrogen atom. "$C_2$-$C_{10}$ alkenyl", "$C_2$-$C_8$ alkenyl", "$C_2$-$C_4$ alkenyl", or "$C_3$-$C_6$ alkenyl", refer to alkenyl groups containing from two to ten, two to eight, two to four or three to six carbon atoms respectively. Alkenyl groups include, but are not limited to, for example, ethenyl, propenyl, butenyl, 1-methyl-2-buten-1-yl, heptenyl, octenyl, and the like.

The term "alkynyl" as used herein, refers to straight- or branched-chain hydrocarbon radicals having at least one carbon-carbon triple bond by the removal of a single hydrogen atom. "$C_2$-$C_{10}$ alkynyl", "$C_2$-$C_8$ alkynyl", "$C_2$-$C_4$ alkynyl", or "$C_3$-$C_6$ alkynyl" refer to alkynyl groups containing from two to ten, two to eight, two to four or three to six carbon atoms respectively. Representative alkynyl groups include, but are not limited to, for example, ethynyl, 1-propynyl, 1-butynyl, heptynyl, octynyl, and the like.

The term "cycloalkyl", as used herein, refers to a monocyclic or polycyclic saturated carbocyclic ring or a bi- or tri-cyclic group fused, bridged or spiro system, and the carbon atoms may be optionally oxo-substituted or optionally substituted with exocyclic olefinic, iminic or oximic double bond. Preferred cycloalkyl groups include $C_3$-$C_{12}$ cycloalkyl, $C_3$-$C_6$ cycloalkyl, $C_3$-$C_8$ cycloalkyl and $C_4$-$C_7$ cycloalkyl. Examples of $C_3$-$C_{12}$ cycloalkyl include, but not limited to, cyclopropyl, cyclobutyl, cyclopentyl, cyclohexyl, cyclopentyl, cyclooctyl, 4-methylene-cyclohexyl, bicyclo [2.2.1]heptyl, bicyclo[3.1.0]hexyl, spiro[2.5]octyl, 3-methylenebicyclo[3.2.1]octyl, spiro[4.4]nonanyl, and the like.

The term "cycloalkenyl", as used herein, refers to monocyclic or polycyclic carbocyclic ring or a bi- or tri-cyclic group fused, bridged or spiro system having at least one carbon-carbon double bond and the carbon atoms may be optionally oxo-substituted or optionally substituted with exocyclic olefinic, iminic or oximic double bond. Preferred cycloalkenyl groups include $C_3$-$C_{12}$ cycloalkenyl, $C_3$-$C_8$ cycloalkenyl or $C_5$-$C_7$ cycloalkenyl groups. Examples of $C_3$-$C_{12}$ cycloalkenyl include, but not limited to, cyclopropenyl, cyclobutenyl, cyclopentenyl, cyclohexenyl, cycloheptenyl, cyclooctenyl, bicyclo[2.2.1]hept-2-enyl, bicyclo [3.1.0]hex-2-enyl, spiro[2.5]oct-4-enyl, spiro[4.4]non-1-enyl, bicyclo[4.2.1]non-3-en-9-yl, and the like.

The term "aryl," as used herein, refers to a mono- or polycyclic carbocyclic ring system comprising at least one aromatic ring, including, but not limited to, phenyl, naphthyl, tetrahydronaphthyl, indanyl, and indenyl. A polycyclic aryl is a polycyclic ring system that comprises at least one aromatic ring. Polycyclic aryls can comprise fused rings, covalently attached rings or a combination thereof.

The term "heteroaryl," as used herein, refers to a mono- or polycyclic aromatic radical having one or more ring atom selected from S, O, and N; and the remaining ring atoms are carbon, wherein any N or S contained within the ring may be optionally oxidized. Heteroaryl includes, but is not limited to, pyridinyl, pyrazinyl, pyrimidinyl, pyrrolyl, pyrazolyl, imidazolyl, thiazolyl, oxazolyl, isoxazolyl, thiadiazolyl, oxadiazolyl, thiophenyl, furanyl, quinolinyl, isoquinolinyl, benzimidazolyl, benzoxazolyl, quinoxalinyl. A polycyclic heteroaryl can comprise fused rings, covalently attached rings or a combination thereof.

In accordance with the invention, aromatic groups can be substituted or unsubstituted. The term "bicyclic aryl" or "bicyclic heteroaryl" refers to a ring system consisting of two rings wherein at least one ring is aromatic; and the two rings can be fused or covalently attached.

As used herein, the term "arylalkyl" means a functional group wherein an alkylene chain is attached to an aryl group, e.g., —$CH_2CH_2$-phenyl. The term "substituted arylalkyl" means an arylalkyl functional group in which the aryl group is substituted. Similarly, the term "heteroarylalkyl" means a functional group wherein an alkylene chain is attached to a heteroaryl group. The term "substituted heteroarylalkyl" means a heteroarylalkyl functional group in which the heteroaryl group is substituted.

The term "alkylene" as used herein, refers to a diradical of a branched or unbranched saturated hydrocarbon chain, typically having from 1 to 20 carbon atoms (e.g. 1-10 carbon atoms, or 1, 2, 3, 4, 5, or 6 carbon atoms). This term is exemplified by groups such as methylene (—$CH_2$—), ethylene (—$CH_2CH_2$—), the propylene isomers (e.g., —$CH_2CH_2CH_2$— and —$CH(CH_3)CH_2$—), and the like.

The term "substituted" as used herein, refers to independent replacement of one, two, or three or more of the hydrogen atoms thereon with substituents including, but not limited to, deuterium, —F, —Cl, —Br, —I, —OH, protected hydroxy, —$NO_2$, —CN, —$NH_2$, $N_3$, protected amino, alkoxy, thioalkoxy, oxo, —$C_1$-$C_{12}$-alkyl; —$C_2$-$C_{12}$-alkenyl, —$C_2$-$C_{12}$-alkynyl, —$C_3$-$C_{12}$-cycloalkyl, -heterocycloalkyl, -halo-$C_1$-$C_{12}$-alkyl, -halo-$C_2$-$C_{12}$-alkenyl, -halo-$C_2$-$C_{12}$-alkynyl, -halo-$C_3$-$C_{12}$-cycloalkyl, —NH—$C_1$-$C_{12}$-alkyl, —NH—$C_2$-$C_{12}$-alkenyl, —NH—$C_2$-$C_{12}$-alkynyl, —NH—$C_3$-$C_{12}$-cycloalkyl, —NH-aryl, —NH-heteroaryl, —NH-heterocycloalkyl, -dialkylamino, -diarylamino, -diheteroarylamino, —O—$C_1$-$C_{12}$-alkyl, —O—$C_2$-$C_{12}$-alkenyl, —O—$C_2$-$C_{12}$-alkynyl, —O—$C_3$-$C_{12}$-cycloalkyl, —O-aryl, —O-heteroaryl, —O-heterocycloalkyl, —C(O)—$C_1$-$C_{12}$-alkyl, —C(O)—$C_2$-$C_{12}$-alkenyl, —C(O)—$C_2$-$C_{12}$-alkynyl, —C(O)—$C_3$-$C_{12}$-cycloalkyl, —C(O)-aryl, —C(O)-heteroaryl, —C(O)-heterocycloalkyl, —$CONH_2$, —CONH—$C_1$-$C_{12}$-alkyl, —CONH—$C_2$-$C_{12}$-alkenyl, —CONH—$C_2$-$C_{12}$-alkynyl, —CONH—$C_3$-$C_{12}$-cycloalkyl, —CONH-aryl, —CONH-heteroaryl, —CONH-heterocycloalkyl, —$OCO_2$—$C_1$-$C_{12}$-alkyl, —$OCO_2$—$C_2$-$C_{12}$-alkenyl, —$OCO_2$—$C_3$-$C_{12}$-cycloalkyl, —$OCO_2$-aryl, —$OCO_2$-heteroaryl, —$OCO_2$-heterocycloalkyl, —$OCONH_2$, —OCONH—$C_1$-$C_{12}$-alkyl, —OCONH—$C_2$-$C_{12}$alkenyl, —OCONH—$C_2$-$C_{12}$-alkynyl, —OCONH—$C_3$-$C_{12}$-cycloalkyl, —OCONH-aryl, —OCONH-heteroaryl, —OCONH-heterocycloalkyl, —NHC(O)—$C_1$-$C_{12}$-alkyl, —NHC(O)—$C_2$-$C_{12}$-alkenyl, —NHC(O)—$C_2$-$C_{12}$-alkynyl, —NHC(O)—$C_3$-$C_{12}$-cycloalkyl, —NHC(O)-aryl, —NHC(O)-heteroaryl, —NHC(O)-heterocycloalkyl, —$NHCO_2$—$C_1$-$C_{12}$-alkyl, —$NHCO_2$—$C_2$-$C_{12}$-alkenyl, —$NHCO_2$—$C_2$-$C_{12}$-alkynyl, —$NHCO_2$—$C_3$-$C_{12}$-cycloalkyl, —$NHCO_2$-aryl, —$NHCO_2$-heteroaryl, —$NHCO_2$-heterocycloalkyl, —$NHC(O)NH_2$, —NHC(O)NH—$C_1$-$C_{12}$-alkyl, —NHC(O)NH—$C_2$-$C_{12}$-alkenyl, —NHC(O)NH—$C_2$-$C_{12}$-alkynyl, —NHC(O)NH—$C_3$-$C_{12}$-cycloalkyl, —NHC(O)NH-aryl, —NHC(O)NH-heteroaryl, —NHC(O)NH-heterocycloalkyl, $NHC(S)NH_2$, —NHC(S)NH—$C_1$-$C_{12}$-alkyl, —NHC(S)NH—$C_2$-$C_{12}$-alkenyl, —NHC(S)NH—$C_2$-$C_{12}$-alkynyl, —NHC(S)NH—$C_3$-$C_{12}$-cycloalkyl, —NHC(S)NH-aryl, —NHC(S)NH-heteroaryl, —NHC(S)NH-heterocycloalkyl, —$NHC(NH)NH_2$, —NHC(NH)NH—$C_1$-$C_{12}$-alkyl, —NHC(NH)NH—$C_2$-$C_{12}$-alkenyl, —NHC(NH)NH—$C_2$-$C_{12}$-alkynyl, —NHC(NH)NH—$C_3$-$C_{12}$-cycloalkyl, —NHC(NH)NH-aryl, —NHC(NH)NH-heteroaryl, —NHC(NH)NH-heterocycloalkyl, —NHC(NH)—$C_1$-$C_{12}$-alkyl, —NHC(NH)—$C_2$-$C_{12}$-alkenyl, —NHC(NH)—$C_2$-$C_{12}$-alkynyl, —NHC(NH)—$C_3$-$C_{12}$-cycloalkyl, —NHC(NH)-aryl, —NHC(NH)-heteroaryl, —NHC(NH)-heterocycloalkyl, —C(NH)NH—$C_1$-$C_{12}$-alkyl, —C(NH)NH—$C_2$-$C_{12}$-alkenyl, —C(NH)NH—$C_2$-$C_{12}$-alkynyl, —C(NH)NH—$C_3$-$C_{12}$-cycloalkyl, —C(NH)NH-aryl, —C(NH)NH-heteroaryl, —C(NH)NH-heterocycloalkyl, —S(O)—$C_1$-$C_{12}$-alkyl, —S(O)—$C_2$-$C_{12}$-alkenyl, —S(O)—$C_2$-$C_{12}$-alkynyl, —S(O)—$C_3$-$C_{12}$-cycloalkyl, —S(O)-aryl, —S(O)-heteroaryl, —S(O)-heterocycloalkyl-$SO_2NH_2$, —$SO_2NH$—$C_1$-$C_{12}$-alkyl, —$SO_2NH$—$C_2$-$C_{12}$-alkenyl, —$SO_2NH$—$C_2$-$C_{12}$-alkynyl, —$SO_2NH$—$C_3$-$C_{12}$-cycloalkyl, —$SO_2NH$-aryl, —$SO_2NH$-heyeroaryl, —$SO_2NH$-heterocycloalkyl, —$NHSO_2$—$C_1$-$C_{12}$-alkyl, —$NHSO_2$—$C_2$-$C_{12}$-alkenyl, —$NHSO_2$—$C_2$-$C_{12}$-alkynyl, —$NHSO_2$—$C_3$-$C_{12}$-cycloalkyl, —$NHSO_2$-aryl, —$NHSO_2$-heteroaryl, —$NHSO_2$-heterocycloalkyl, —$CH_2NH_2$, —$CH_2SO_2CH_3$, -aryl, -arylalkyl, -heteroaryl, -heteroarylalkyl, -heterocycloalkyl, —$C_3$-$C_{12}$-cycloalkyl, polyalkoxyalkyl, polyalkoxy, -methoxymethoxy, -methoxyethoxy, —SH, —S—$C_1$-$C_{12}$-alkyl, —S—$C_2$-$C_{12}$-alkenyl, —S—$C_2$-$C_{12}$-alkynyl, —S—$C_3$-$C_{12}$-cycloalkyl, —S-aryl, —S-heteroaryl, —S-heterocycloalkyl, methylthiomethyl, or -L'—R', wherein L' is $C_1$-$C_6$alkylene, $C_2$-$C_6$alkenylene or $C_2$-$C_6$alkynylene, and R' is aryl, heteroaryl, heterocyclic, $C_3$-$C_{12}$cycloalkyl or $C_3$-$C_{12}$cycloalkenyl. In certain embodiments, the substituents are independently selected from halo, preferably Cl and F; $C_1$-$C_4$-alkyl, preferably methyl and ethyl; $C_2$-$C_4$-alkenyl; halo-$C_1$-$C_4$-alkyl, such as fluoromethyl, difluoromethyl, and trifluoromethyl; halo-$C_2$-$C_4$-alkenyl; $C_3$-$C_6$-cycloalkyl, such as cyclopropyl; —CN; —OH; $NH_2$; $C_1$-$C_4$-alkylamino; di($C_1$-$C_4$-alkyl)amino; and $NO_2$. It is understood that the aryls, heteroaryls, alkyls, and the like can be further substituted. In some cases, each substituent in a substituted moiety is additionally optionally substituted with one or more groups, each group being independently selected from $C_1$-$C_4$-alkyl, —F, —Cl, —Br, —I, —OH, —$NO_2$, —CN, or —$NH_2$.

In accordance with the invention, any of the aryls, substituted aryls, heteroaryls and substituted heteroaryls described herein, can be any aromatic group. Aromatic groups can be substituted or unsubstituted.

It is understood that any alkyl, alkenyl, alkynyl, cycloalkyl and cycloalkenyl moiety described herein can also be an aliphatic group, an alicyclic group or a heterocyclic group. An "aliphatic group" is non-aromatic moiety that may contain any combination of carbon atoms, hydrogen atoms, halogen atoms, oxygen, nitrogen or other atoms, and optionally contain one or more units of unsaturation, e.g., double and/or triple bonds. An aliphatic group may be straight chained, branched or cyclic and preferably contains between about 1 and about 24 carbon atoms, more typically between about 1 and about 12 carbon atoms. In addition to aliphatic hydrocarbon groups, aliphatic groups include, for example, polyalkoxyalkyls, such as polyalkylene glycols, polyamines, and polyimines, for example. Such aliphatic groups may be further substituted. It is understood that aliphatic groups may be used in place of the alkyl, alkenyl, alkynyl, alkylene, alkenylene, and alkynylene groups described herein.

The term "alicyclic" as used herein, denotes a monovalent group derived from a monocyclic or polycyclic saturated carbocyclic ring compound by the removal of a single hydrogen atom. Examples include, but are not limited to, cyclopropyl, cyclobutyl, cyclopentyl, cyclohexyl, bicyclo[2.2.1]heptyl, and bicyclo[2.2.2]octyl. Such alicyclic groups may be further substituted.

As used herein, the term "alkoxy" employed alone or in combination with other terms means, unless otherwise stated, an alkyl group having the designated number of carbon atoms connected to the rest of the molecule via an oxygen atom, such as, for example, methoxy, ethoxy, 1-propoxy, 2-propoxy (isopropoxy) and the higher homologs and isomers. Preferred alkoxy are ($C_1$-$C_3$) alkoxy.

The term "aryloxy" refers to the group aryl-O— wherein the aryl group is as defined above, and includes optionally substituted aryl groups as also defined above. The term "arylthio" refers to the group R—S—, where R is as defined for aryl.

The terms "heterocyclic" or "heterocycloalkyl" can be used interchangeably and referred to a non-aromatic ring or a bi- or tri-cyclic group fused, bridged or spiro system, where (i) each ring system contains at least one heteroatom independently selected from oxygen, sulfur and nitrogen, (ii) each ring system can be saturated or unsaturated (iii) the nitrogen and sulfur heteroatoms may optionally be oxidized, (iv) the nitrogen heteroatom may optionally be quaternized, (v) any of the above rings may be fused to an aromatic ring, and (vi) the remaining ring atoms are carbon atoms which may be optionally oxo-substituted or optionally substituted with exocyclic olefinic, iminic or oximic double bond. Representative heterocycloalkyl groups include, but are not limited to, 1,3-dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, 2-azabicyclo

[2.2.1]-heptyl, 8-azabicyclo[3.2.1]octyl, 5-azaspiro[2.5]octyl, 1-oxa-7-azaspiro[4.4]nonanyl, 7-oxooxepan-4-yl, and tetrahydrofuryl. Such heterocyclic groups may be further substituted. Heteroaryl or heterocyclic groups can be C-attached or N-attached (where possible).

It is understood that any alkyl, alkenyl, alkynyl, cycloalkyl, heterocyclic and cycloalkenyl moiety described herein can also be an aliphatic group or an alicyclic group.

It will be apparent that in various embodiments of the invention, the substituted or unsubstituted alkyl, alkenyl, alkynyl, cycloalkyl, cycloalkenyl, cycloalkynyl, arylalkyl, heteroarylalkyl, and heterocycloalkyl are intended to be monovalent or divalent. Thus, alkylene, alkenylene, and alkynylene, cycloaklylene, cycloalkenylene, cycloalkynylene, arylalkylene, heteroarylalkylene and heterocycloalkylene groups are to be included in the above definitions and are applicable to provide the Formulas herein with proper valency.

The terms "halo" and "halogen," as used herein, refer to an atom selected from fluorine, chlorine, bromine and iodine. Preferred halogens are fluorine and chlorine.

The term "optionally substituted", as used herein, means that the referenced group may be substituted or unsubstituted. In one embodiment, the referenced group is optionally substituted with zero substituents, i.e., the referenced group is unsubstituted. In another embodiment, the referenced group is optionally substituted with one or more additional group(s) individually and independently selected from groups described herein.

The term "hydrogen" includes hydrogen and deuterium. In addition, the recitation of an atom includes other isotopes of that atom so long as the resulting compound is pharmaceutically acceptable.

In certain embodiments, the compounds of each formula herein are defined to include isotopically labelled compounds. An "isotopically labelled compound" is a compound in which at least one atomic position is enriched in a specific isotope of the designated element to a level which is significantly greater than the natural abundance of that isotope. For example, one or more hydrogen atom positions in a compound can be enriched with deuterium to a level which is significantly greater than the natural abundance of deuterium, for example, enrichment to a level of at least 1%, preferably at least 20% or at least 50%. Such a deuterated compound may, for example, be metabolized more slowly than its non-deuterated analog, and therefore exhibit a longer half-life when administered to a subject. Such compounds can synthesize using methods known in the art, for example by employing deuterated starting materials. Unless stated to the contrary, isotopically labelled compounds are pharmaceutically acceptable.

The compounds described herein contain one or more asymmetric centers and thus give rise to enantiomers, diastereomers, and other stereoisomeric forms that may be defined, in terms of absolute stereochemistry, as (R)— or (S)—, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981). When the compounds described herein contain olefinic double bonds, other unsaturation, or other centers of geometric asymmetry, and unless specified otherwise, it is intended that the compounds include both E and Z geometric isomers or cis- and trans-isomers. Likewise, all tautomeric forms are also intended to be included. Tautomers may be in cyclic or acyclic. The configuration of any carbon-carbon double bond appearing herein is selected for convenience only and is not intended to designate a particular configuration unless the text so states; thus, a carbon-carbon double bond or carbon-heteroatom double bond depicted arbitrarily herein as trans may be cis, trans, or a mixture of the two in any proportion.

The term "subject" as used herein refers to a mammal. A subject therefore refers to, for example, dogs, cats, horses, cows, pigs, guinea pigs, and the like. Preferably the subject is a human. When the subject is a human, the subject may be referred to herein as a patient.

As used herein, the term "pharmaceutically acceptable salt" refers to those salts of the compounds formed by the process of the present invention which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art.

Berge, et al. describes pharmaceutically acceptable salts in detail in J. Pharmaceutical Sciences, 66: 1-19 (1977). The salts can be prepared in situ during the final isolation and purification of the compounds of the invention, or separately by reaction of the free base function with a suitable organic acid. Examples of pharmaceutically acceptable salts include, but are not limited to, nontoxic acid addition salts e.g., salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, esters of $C_1$-$C_6$-alkanoic acids, such as acetate, propionate, butyrate and pivalate esters.

The term "hydroxy activating group," as used herein, refers to a labile chemical moiety which is known in the art to activate a hydroxyl group so that it will depart during synthetic procedures such as in a substitution or an elimination reaction. Examples of hydroxyl activating group include, but not limited to, mesylate, tosylate, triflate, p-nitrobenzoate, phosphonate and the like.

The term "activated hydroxyl," as used herein, refers to a hydroxy group activated with a hydroxyl activating group, as defined above, including mesylate, tosylate, triflate, p-nitrobenzoate, phosphonate groups, for example.

The term "hydroxy protecting group," as used herein, refers to a labile chemical moiety which is known in the art to protect a hydroxyl group against undesired reactions during synthetic procedures. After said synthetic procedure(s) the hydroxy protecting group as described herein may be selectively removed. Hydroxy protecting groups as known in the art are described generally in T. H. Greene and P. G. M. Wuts, *Protective Groups in Organic Synthesis*, 3rd edition, John Wiley & Sons, New York (1999). Examples of hydroxyl protecting groups include benzyloxycarbonyl, 4-methoxybenzyloxycarbonyl, tert-butoxy-carbonyl, isopropoxycarbonyl, diphenylmethoxycarbonyl, 2,2,2-trichloroethoxycarbonyl, allyloxycarbonyl, acetyl, formyl, chloroacetyl, trifluoroacetyl, methoxyacetyl, phenoxyacetyl, benzoyl, methyl, t-butyl, 2,2,2-trichloroethyl, 2-trimethylsilyl ethyl, allyl, benzyl, triphenyl-methyl (trityl), methoxymethyl, methylthiomethyl, benzyloxymethyl, 2-(trimethylsilyl)-ethoxymethyl, methanesulfonyl, trimethylsilyl, triisopropylsilyl, and the like.

The term "protected hydroxy," as used herein, refers to a hydroxy group protected with a hydroxy protecting group, as defined above, including benzoyl, acetyl, trimethylsilyl, triethylsilyl, methoxymethyl groups, for example.

The term "hydroxy prodrug group," as used herein, refers to a promoiety group which is known in the art to change the physicochemical, and hence the biological properties of a parent drug in a transient manner by covering or masking the hydroxy group. After said synthetic procedure(s), the hydroxy prodrug group as described herein must be capable of reverting back to hydroxy group in vivo. Hydroxy prodrug groups as known in the art are described generally in Kenneth B. Sloan, *Prodrugs, Topical and Ocular Drug Delivery*, (Drugs and the Pharmaceutical Sciences; Volume 53), Marcel Dekker, Inc., New York (1992) and in "Prodrugs of Alcohols and Phenols" by S. S. Dhareshwar and V. J. Stella, in *Prodrugs Challenges and Rewards Part-2*, (Biotechnology: Pharmaceutical Aspects), edited by V. J. Stella, et al, Springer and AAPSPress, 2007, pp 31-99.

The term "amino" as used herein, refers to the group —$NH_2$.

The term "substituted amino" as used herein, refers to the group —NRR where each R is independently selected from the group consisting of hydrogen, alkyl, cycloalkyl, aryl, heteroaryl and heterocycloalkyl provided that both R groups are not hydrogen, or a group —Y—Z, in which Y is optionally substituted alkylene and Z is alkenyl, cycloalkenyl, or alkynyl.

The term "amino protecting group" as used herein, refers to a labile chemical moiety which is known in the art to protect an amino group against undesired reactions during synthetic procedures. After said synthetic procedure(s) the amino protecting group as described herein may be selectively removed. Amino protecting groups as known in the art are described generally in T. H. Greene and P. G. M. Wuts, *Protective Groups in Organic Synthesis*, 3rd edition, John Wiley & Sons, New York (1999). Examples of amino protecting groups include, but are not limited to, t-butoxycarbonyl, 9-fluorenylmethoxycarbonyl, benzyloxycarbonyl, and the like.

The term "leaving group" means a functional group or atom which can be displaced by another functional group or atom in a substitution reaction, such as a nucleophilic substitution reaction. By way of example, representative leaving groups include chloro, bromo and iodo groups; sulfonic ester groups, such as mesylate, tosylate, brosylate, nosylate and the like; and acyloxy groups, such as acetoxy, trifluoroacetoxy and the like.

As used herein, the term "pharmaceutically acceptable ester" refers to esters of the compounds formed by the process of the present invention which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs" as used herein refers to those prodrugs of the compounds formed by the process of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention. "Prodrug", as used herein means a compound, which is convertible in vivo by metabolic means (e.g. by hydrolysis) to afford any compound delineated by the Formulae of the instant invention. Various forms of prodrugs are known in the art, for example, as discussed in Bundgaard, (ed.), *Design of Prodrugs*, Elsevier (1985); Widder, et al. (ed.), *Methods in Enzymology*, Vol. 4, Academic Press (1985); Krogsgaard-Larsen, et al., (ed). "Design and Application of Prodrugs, *Textbook of Drug Design and Development*, Chapter 5, 113-191 (1991); Bundgaard, et al., *Journal of Drug Deliver Reviews*, 8:1-38 (1992); Bundgaard, J. of *Pharmaceutical Sciences*, 77:285 et seq. (1988); Higuchi and Stella (eds.) Prodrugs as Novel Drug Delivery Systems, *American Chemical Society* (1975); and Bernard Testa & Joachim Mayer, "Hydrolysis In Drug And Prodrug Metabolism: Chemistry, Biochemistry and Enzymology," John Wiley and Sons, Ltd. (2002).

The term "treating", as used herein, means relieving, lessening, reducing, eliminating, modulating, or ameliorating, i.e. causing regression of the disease state or condition. Treating can also include inhibiting, i.e. arresting the development, of an existing disease state or condition, and relieving or ameliorating, i.e. causing regression of an existing disease state or condition, for example when the disease state or condition may already be present.

The term "preventing", as used herein means, to completely or almost completely stop a disease state or condition, from occurring in a patient or subject, especially when the patient or subject is predisposed to such or at risk of contracting a disease state or condition.

Additionally, the compounds of the present invention, for example, the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

"Solvates" means solvent addition forms that contain either stoichiometric or non-stoichiometric amounts of solvent. Some compounds have a tendency to trap a fixed molar ratio of solvent molecules in the crystalline solid state, thus forming a solvate. If the solvent is water, the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

As used herein, the term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar to or comparable in function and appearance to the reference compound.

The term "aprotic solvent," as used herein, refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidinone, and ethers such as diethyl ether, bis-methoxymethyl ether. Such solvents are well known to those skilled in the art, and individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series,* John Wiley & Sons, NY, 1986.

The terms "protogenic organic solvent" or "protic solvent" as used herein, refer to a solvent that tends to provide protons, such as an alcohol, for example, methanol, ethanol, propanol, isopropanol, butanol, t-butanol, and the like. Such solvents are well known to those skilled in the art, and individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series,* John Wiley & Sons, NY, 1986.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

The synthesized compounds can be separated from a reaction mixture and further purified by a method such as column chromatography, high pressure liquid chromatography, or recrystallization. Additionally, the various synthetic steps may be performed in an alternate sequence or order to give the desired compounds. In addition, the solvents, temperatures, reaction durations, etc. delineated herein are for purposes of illustration only and variation of the reaction conditions can produce the desired isoxazole products of the present invention. Synthetic chemistry transformations and protecting group methodologies (protection and deprotection) useful in synthesizing the compounds described herein include, for example, those described in R. Larock, *Comprehensive Organic Transformations,* VCH Publishers (1989); T. W. Greene and P. G. M. Wuts, *Protective Groups in Organic Synthesis,* 2d. Ed., John Wiley and Sons (1991); L. Fieser and M. Fieser, *Fieser and Fieser's Reagents for Organic Synthesis,* John Wiley and Sons (1994); and L. Paquette, ed., *Encyclopedia of Reagents for Organic Synthesis,* John Wiley and Sons (1995).

The compounds of this invention may be modified by appending various functionalities via synthetic means delineated herein to enhance selective biological properties. Such modifications include those which increase biological penetration into a given biological system (e.g., blood, lymphatic system, central nervous system), increase oral availability, increase solubility to allow administration by injection, alter metabolism and alter rate of excretion.

Pharmaceutical Compositions

The pharmaceutical compositions of the present invention comprise a therapeutically effective amount of a compound of the present invention Formulated together with one or more pharmaceutically acceptable carriers. As used herein, the term "pharmaceutically acceptable carrier" means a non-toxic, inert solid, semi-solid or liquid filler, diluent, encapsulating material or Formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the Formulator. The pharmaceutical compositions of this invention can be administered to humans and other animals orally, rectally, parenterally, intracisternally, intravaginally, intraperitoneally, topically (as by powders, ointments, or drops), buccally, or as an oral or nasal spray.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional nontoxic pharmaceutically-acceptable carriers, adjuvants or vehicles. In some cases, the pH of the Formulation may be adjusted with pharmaceutically acceptable acids, bases or buffers to enhance the stability of the Formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1, 3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid are used in the preparation of injectables.

The injectable Formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable Formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragées, capsules, pills, and granules can be prepared with coatings and shells such as enteric coatings, release controlling coatings and other coatings well known in the pharmaceutical Formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic Formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Unless otherwise defined, all technical and scientific terms used herein are accorded the meaning commonly known to one with ordinary skill in the art. All publications, patents, published patent applications, and other references mentioned herein are hereby incorporated by reference in their entirety.

Abbreviations

Abbreviations which have been used in the descriptions of the schemes and the examples that follow are:
BOP—Cl for bis(2-oxo-3-oxazolidinyl)phosphinic chloride;
CDI for carbonyldiimidazole;
DBU for 1,8-diazabicycloundec-7-ene;
DCC for N,N'-dicyclohexylcarbodiimide;
DCM for dichloromethane;
DIPEA for N,N-diisopropylethylamine;
DMAP for N,N-dimethylaminopyridine;
DME for 1,2-dimethoxyethane;
DMF for N,N-dimethyl formamide;
DMPU for 1,3-Dimethyl-3,4,5,6-tetrahydro-2(1H)-pyrimidinone;
EDC for 1-(3-diethylaminopropyl)-3-ethylcarbodiimide hydrochloride;
$Et_3N$ for triethylamine;
EtOAc for ethyl acetate;
HATU for 1-[bis(dimethylamino)methylene]-1H-1,2,3-triazolo[4,5-b]pyridinium 3-oxide hexafluorophosphate;
HCl for hydrochloric acid;
mCPBA for meta-chloroperoxybenzoic acid;
NMO for N-methylmorpholine-N-oxide;
PhMe for toluene;
PyAOP for 7-azabenzotriazol-1-yloxy)tripyrrolidinophosphonium hexafluorophosphate;
PyBOP for benzotriazol-1-yl-oxytripyrrolidinophosphonium hexafluorophosphate;
THF for tetrahydrofuran;
CuTC for Copper(I)-thiophene-2-carboxylate;
Xantphos for 4,5-Bis(diphenylphosphino)-9,9-dimethylxanthene;
Me4tButylXphos for 2-Di-tert-butylphosphino-3,4,5,6-tetramethyl-2',4',6'-triisopropyl-1,1'-biphenyl;
Pd2(dba)3 for Tris(dibenzylideneacetone)dipalladium(0);
PMBCl for p-methoxybenzyl chloride.

Synthetic Methods

The compounds and processes of the present invention will be better understood in connection with the following synthetic schemes that illustrate the methods by which the compounds of the invention may be prepared, which are intended as an illustration only and not to limit the scope of the invention. Various changes and modifications to the disclosed embodiments will be apparent to those skilled in the art and such changes and modifications including, without limitation, those relating to the chemical structures, substituents, derivatives, and/or methods of the invention may be made without departing from the spirit of the invention and the scope of the appended claims.

As shown in Scheme 1, the compound of Formula (I) can be prepared by C—N coupling, wherein $R_1$, $R_2$, $R_3$, $R_4$, $X_1$, $X_2$, $X_3$ and $X_4$ are as previously defined. The lactam compound (1) and aromatic bromide compound (2) are subjected to suitable C—N coupling conditions, such as but not limited to, mixed with $Pd_2(dba)_3$, $Cs_2CO_3$ and Xantphos in dioxane at elevated temperature. Alternative reagents and reaction conditions may be used, including but not limited to, a suspension of compound (1) and compound (2) with CuTC, $K_2CO_3$ in DMSO under microwave irradiation.

Scheme 1

Alternatively, the compound of Formula (I) may also be prepared from nucleophilic aromatic substitution of lactam compound (1) and aromatic chloride compound (3) under suitable conditions. Thus, suitable base is slowly added to a solution of lactam compound (1) in an aprotic solvent at low temperature. The base can be, such as but not limited to, nBuLi, KHMDS, NaH and KOtBu. The aprotic solvent can be, such as, but not limited to, THF and DMF. Then the aromatic chloride compound (2) is slowly added to the resulting reaction mixture. The reaction temperature is from 0° C. to 80° C.

Scheme 2

EXAMPLES

The compounds and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, Formulations and/or methods of the invention may be made without departing from the spirit of the invention and the scope of the appended claims.

Synthesis of 6-(4-cyclopropyl-1H-imidazol-1-yl)isoindolin-1-one (Compound 5)

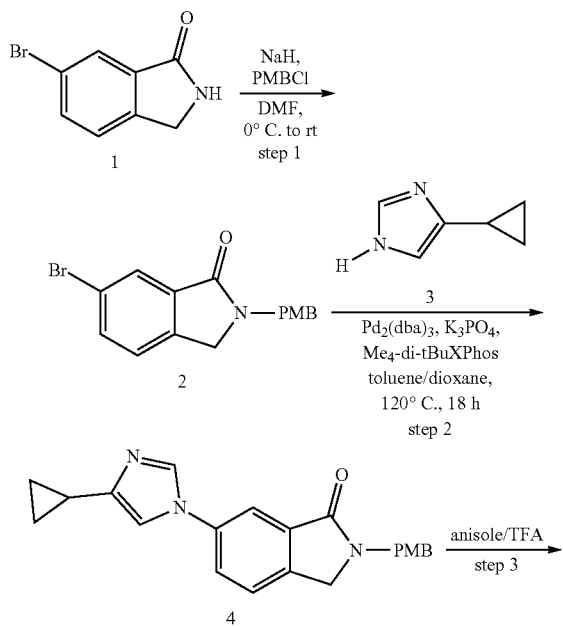

Step 1: Synthesis of 6-bromo-2-(4-methoxybenzyl)isoindolin-1-one (Compound 2)

To a solution of 6-bromoisoindolin-1-one (2.418 g, 11.4 mmol) in DMF (57 mL) at 0° C. was added NaH (0.547 g, 13.68 mmol). The resulting dark suspension was allowed to stir for 60 min before addition of PMBCl (1.86 mL, 13.68 mmol). The reaction was then allowed to stir at room temperature for 3 hours. The crude was diluted by EtOAc, washed with water and brine. The organic layers were dried over $Na_2SO_4$ and concentrated. The residue was purified by chromatography on silica gel using 0->50% EtOAc in hexanes to afford 3.18 g yellow solid as compound 2 (84% yield). $^1$H NMR (400 MHz, Chloroform-d) δ8.04 (d, J=1.9 Hz, 1H), 7.65 (dd, J=8.0, 1.9 Hz, 1H), 7.25 (d, J=8.6 Hz, 2H), 6.89 (d, J=8.6 Hz, 2H), 4.75 (s, 2H), 4.22 (s, 2H), 3.82 (s, 3H).

Step 2: Synthesis of 6-(4-cyclopropyl-1H-imidazol-1-yl)-2-(4-methoxybenzyl)isoindolin-1-one (Compound 4)

To a solution of 6-bromo-2-(4-methoxybenzyl)isoindolin-1-one (1 g, 3.01 mmol) in toluene (12 mL) and dioxane (3 mL) was added 4-cyclopropyl-1H-imidazole (0.651 g, 6.02 mmol), $K_3PO_4$ (1.278 g, 6.02 mmol), $Pd_2(dba)_3$ (110 mg, 0.12 mmol) and $Me_4$-di-tBuXPhos (145 mg, 0.301 mmol). The reaction was degassed and allowed to stir at 120° C. for overnight. The crude was filtered and concentrated. The residue was purified by chromatography on silica gel using 0->10% MeOH in DCM to afford 490 mg white solid as compound 4 (45% yield). $^1$H NMR (500 MHz, DMSO-d6) δ8.22 (d, J=1.5 Hz, 1H), 7.92 (d, J=2.1 Hz, 1H), 7.83 (dd, J=8.2, 2.2 Hz, 1H), 7.66 (d, J=8.2 Hz, 1H), 7.62 (d, J=1.5 Hz, 1H), 7.24 (d, J=8.7 Hz, 2H), 6.92 (d, J=8.7 Hz, 2H), 4.69 (s, 2H), 4.36 (s, 2H), 3.74 (s, 3H), 1.84 (td, J=8.4, 4.2 Hz, 1H), 0.81 (dt, J=8.3, 2.9 Hz, 2H), 0.73-0.69 (m, 2H).

Step 3: Synthesis of 6-(4-cyclopropyl-1H-imidazol-1-yl)isoindolin-1-one (Compound 5)

The solution of 6-(4-cyclopropyl-1H-imidazol-1-yl)-2-(4-methoxybenzyl)isoindolin-1-one (490 mg, 1.36 mmol) in 10% anisole in TFA (6 mL) was allowed to stir at 85° C. for 3 days. The reaction was cooled to room temperature and concentrated. The residue was purified by chromatography on silica gel using 0->20% MeOH in DCM to afford 340 mg white solid as compound 5 (quant. yield). $^1$H NMR (400 MHz, DMSO-d6) δ9.36-9.17 (m, 1H), 8.82 (s, 1H), 8.04 (dd, J=9.0, 1.8 Hz, 2H), 7.95 (dd, J=8.2, 2.2 Hz, 1H), 7.81 (d, J=8.2 Hz, 1H), 4.47 (s, 2H), 1.97 (m, 1H), 1.06-0.96 (m, 2H), 0.87-0.81 (m, 2H).

Synthesis of 5-(3-bromophenyl)-1-isopropyl-1H-tetrazole (Compound 8)

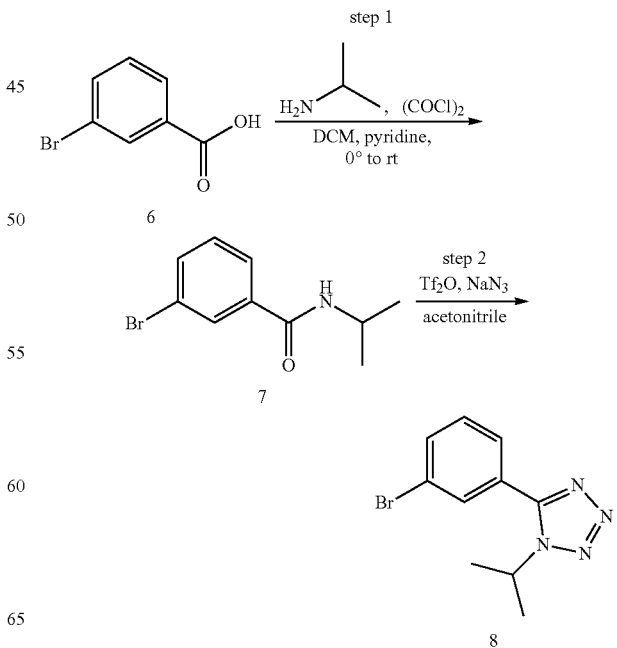

Step 1: Synthesis of 3-bromo-N-isopropylbenzamide (Compound 7)

To a suspension of 3-bromobenzoic acid (1.04 g, 5.18 mmol) in DCM (6.6 mL) was added oxalyl chloride (0.5 mL, 5.7 mmol) and DMF (0.02 mL, 0.259 mmol) at 0° C. The reaction was allowed to stir 4 hours before turning to clear solution. The crude was concentrated and redissolved in pyridine (6.6 mL). A solution of propan-2-amine (0.49 mL, 5.7 mmol) in DCM (6.6 mL) was slowly added at 0° C. The reaction was allowed to stir for overnight. The crude was concentrated and purified by chromatography on silica gel using 0->50% EtOAc in hexanes to afford 1.17 g pale yellow oil as compound 7 (93% yield). $^1$H NMR (400 MHz, Chloroform-d) δ8.18 (dd, J=7.5, 1.0 Hz, 1H), 7.73 (t, J=7.7 Hz, 1H), 7.62 (dd, J=7.9, 1.0 Hz, 1H), 4.29 (dp, J=8.1, 6.6 Hz, 1H), 1.32 (d, J=6.6 Hz, 6H).

Step 2: Synthesis of 5-(3-bromophenyl)-1-isopropyl-1H-tetrazole (Compound 8)

To suspension of 6-bromo-N-isopropylpicolinamide (413.5 mg, 1.701 mmol) and NaN$_3$ (166 mg, 2.55 mmol) in acetonitrile (5.7 mL) at 0° C. was added Tf$_2$O (1M in DCM, 2.55 mL, 2.55 mmol) dropwise. The resulting mixture was stirred for 30 min then warmed up to room temperature for additional 1 hour. The crude was diluted with EA, and quenched with NaHCO$_3$ aq. Solution. The organic layer was separated and washed with brine, dried, filtered and concentrated. The residue was purified by chromatography on silica gel using 0->40% EtOAc in hexanes to afford 56 mg oil as compound 8 (12% yield). $^1$H NMR (400 MHz, Chloroform-d) δ8.34 (dd, J=7.7, 0.9 Hz, 1H), 7.80 (t, J=7.8 Hz, 1H), 7.7 (d, J=7.7 Hz, 1H), 5.82 (p, J=6.7 Hz, 1H), 1.72 (d, J=6.7 Hz, 6H).

Synthesis of 2-bromo-6-(5-isopropyl-1H-tetrazol-1-yl) pyridine (Compound 12)

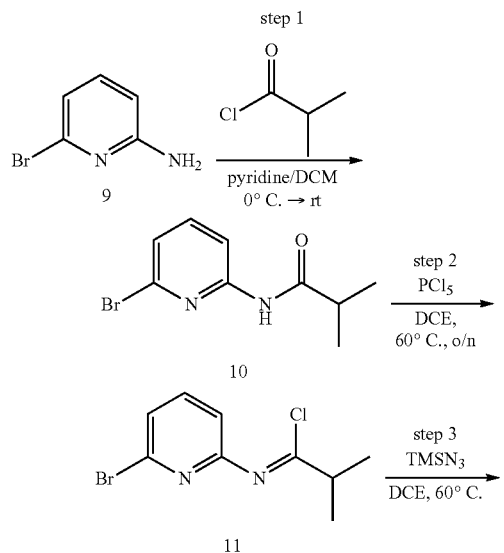

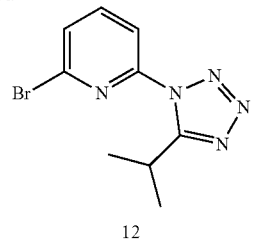

Step 1: Synthesis of N-(6-bromopyridin-2-yl)isobutyramide (Compound 10)

To a solution of 6-bromopyridin-2-amine (883.6 mg, 5.11 mmol) in DCM (6.4 mL) and pyridine (6.4 mL) was slowly added isobutyryl chloride (0.59 mL, 5.62 mmol) at 0° C. The reaction was allowed to stir at room temperature for 2 hours and concentrated. The residue was purified by chromatography on silica gel using 0->40% EtOAc in hexanes to afford 1.1612 g white solid as compound 10 (94% yield). $^1$H NMR (400 MHz, Chloroform-d) δ8.22 (d, J=8.2 Hz, 1H), 7.87 (br, 1H), 7.58 (t, J=7.9 Hz, 1H), 7.23 (d, J=7.7 Hz, 1H), 2.55 (m, 1H), 1.28 (d, J=6.9 Hz, 6H).

Step 2: Synthesis of (Z)—N-(6-bromopyridin-2-yl)isobutyrimidoyl chloride (Compound 11)

To a solution of N-(6-bromopyridin-2-yl)isobutyramide (179.5 mg, 0.738 mmol) in DCE (2.23 mL) was added PCl$_5$ (184 mg, 0.886 mmol). The resulting suspension became clear solution upon heating. The reaction was allowed to stir at 60° C. for overnight. Concentrate to afford light yellow solid. The crude was directly used in the next step without any purification.

Step 3: Synthesis of 2-bromo-6-(5-isopropyl-1H-tetrazol-1-yl)pyridine (Compound 12)

To a solution of (Z)—N-(6-bromopyridin-2-yl)isobutyrimidoyl chloride (193 mg, 0.738 mmol) in DCE (3.7 mL) was added TMSN$_3$ (94 mg, 0.812 mmol). The reaction was allowed to stir at 60° C. for 1 day. The reaction was quenched by aq. NaHCO$_3$, extracted with EtOAc (X3). The combined organic layers were washed by brine, dried over Na$_2$SO$_4$, filtered and concentrate. The residue was purified by chromatography on silica gel using 0->20% EtOAc in hexanes to afford 66 mg white solid as compound 12 (33% yield). $^1$H NMR (500 MHz, Chloroform-d) δ8.01 (d, J=8.0 Hz, 1H), 7.88-7.83 (m, 1H), 7.65 (d, J=7.9 Hz, 1H), 4.05-3.94 (m, 1H), 1.51 (d, J=6.9 Hz, 6H).

Example 1: 6-(4-cyclopropyl-1H-imidazol-1-yl)-2-(6-(5-isopropyl-1H-tetrazol-1-yl)pyridine-2-yl)isoindolin-1-one

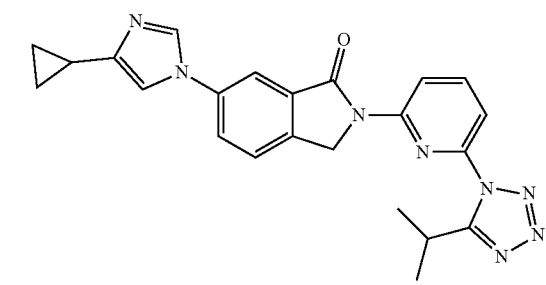

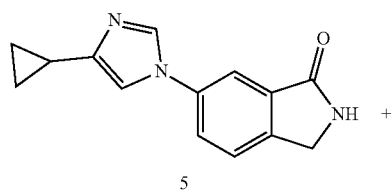

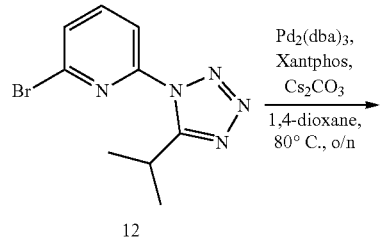

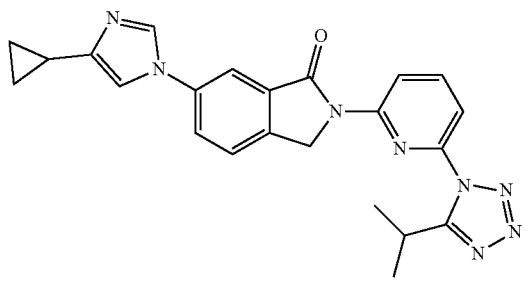

example 1

To a solution of 6-(4-cyclopropyl-1H-imidazol-1-yl)isoindolin-1-one (70.7 mg, 0.295 mmol) in 1,4-dioxane (0.8 mL) was added 2-bromo-6-(5-isopropyl-1H-tetrazol-1-yl)pyridine (66.0 mg, 0.246 mmol), Pd$_2$(dba)$_3$ (11.3 mg, 0.012 mmol), Xantphos (14.2 mg, 0.025 mmol) and Cs$_2$CO$_3$ (160 mg, 0.492 mmol). The reaction was purged with N$_2$ and allowed to stir at 80° C. for overnight. The reaction was concentrated, and the residue was purified by chromatography on silica gel using 0->70% acetone in hexanes to afford 32.1 mg white solid as Example 1 (31% yield). LC-MS [M+H]=427.19, Calcd. 427.19. $^1$H NMR (400 MHz, DMSO-d6) δ8.76 (d, J=8.4 Hz, 1H), 8.33-8.26 (m, 2H), 8.08 (d, J=2.1 Hz, 1H), 8.01 (dd, J=8.2, 2.2 Hz, 1H), 7.88 (d, J=8.3 Hz, 1H), 7.77 (dd, J=7.8, 0.7 Hz, 1H), 7.69 (d, J=1.5 Hz, 1H), 5.17 (s, 2H), 3.94 (p, J=6.8 Hz, 1H), 1.90-1.81 (m, 1H), 0.85-0.80 (m, 2H), 0.75-0.70 (m, 2H).

Example 2: 6-(4-cyclopropyl-1H-imidazol-1-yl)-2-(6-(1-isopropyl-1H-tetrazol-5-yl)pyridine-2-yl)isoindolin-1-one

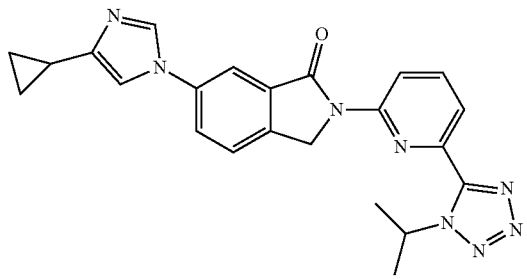 [SMILES: CC(C)n1nnnc1-c1cccc(N2Cc3ccc(-n4cnc(C5CC5)c4)cc3C2=O)n1]

Example 2 was prepared by using similar procedure as described for compound of example 1. LC-MS observed [M+H], 427.19, Calcd. 427.19. $^1$H NMR (400 MHz, DMSO-d6) δ8.78 (d, J=8.5 Hz, 1H), 8.30 (d, J=1.5 Hz, 1H), 8.22 (dd, J=8.5, 7.6 Hz, 1H), 8.09 (d, J=2.2 Hz, 1H), 8.05-8.00 (m, 2H), 7.90 (d, J=8.5 Hz, 1H), 7.69 (d, J=1.5 Hz, 1H), 5.90-5.79 (m, 1H), 5.25 (s, 2H), 1.93-1.82 (m, 1H), 1.70 (d, J=6.9 Hz, 6H), 0.88-0.80 (m, 2H), 0.76-0.72 (m, 2H).

Example 3: 1-2-(5-(6-(6-(4-cyclopropyl-1H-imidazol-1-yl)-1-oxoisoindolin-2-yl)pyridine-2-yl)-1H-tetrazol-1-yl)propyl acetate

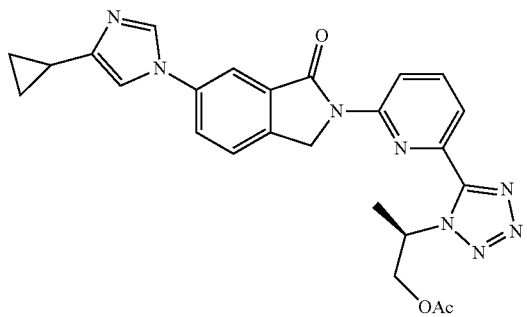 [SMILES: CC(=O)OC[C@@H](C)n1nnnc1-c1cccc(N2Cc3ccc(-n4cnc(C5CC5)c4)cc3C2=O)n1]

Example 3 was prepared by using similar procedure as described for Example 1. LC-MS observed [M+H], 485.20, Calcd. 485.20. $^1$H NMR (400 MHz, DMSO-d6) δ8.78 (dd, J=8.5, 0.9 Hz, 1H), 8.29 (d, J=1.5 Hz, 1H), 8.23 (dd, J=8.5, 7.6 Hz, 1H), 8.09 (d, J=2.1 Hz, 1H), 8.07 (dd, J=7.6, 0.9 Hz, 1H), 8.03 (dd, J=8.2, 2.2 Hz, 1H), 7.87 (d, J=8.2 Hz, 1H), 7.69 (d, J=1.5 Hz, 1H), 6.13 (td, J=7.5, 4.0 Hz, 1H), 5.22 (s, 2H), 4.64 (dd, J=11.6, 4.0 Hz, 1H), 4.50 (dd, J=11.6, 8.1 Hz, 1H), 1.87 (td, J=8.4, 4.2 Hz, 1H), 1.81 (s, 3H), 1.75 (d, J=6.9 Hz, 3H), 0.88-0.80 (m, 2H), 0.75-0.68 (m, 2H).

Example 4: 1-6-(4-cyclopropyl-1H-imidazol-1-yl)-2-(6-(1-(1-hydroxypropan-2-yl)-1H-tetrazol-5-yl)pyridine-2-yl)isoindolin-1-one

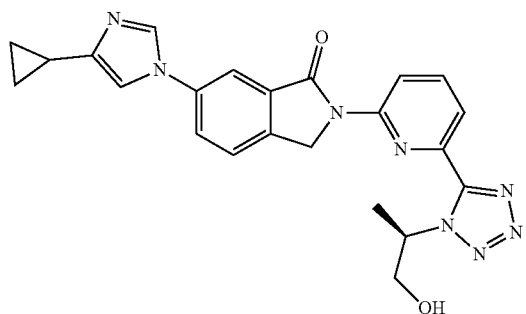

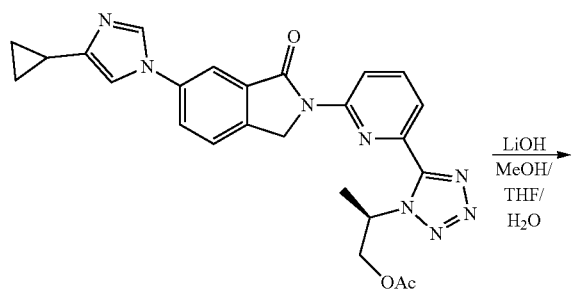

example 3

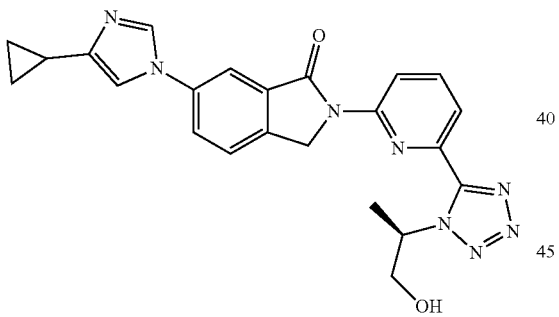

example 4

To a solution of Example 3 (49.7 mg, 0.103 mmol) in MeOH/H$_2$O/THF (1:1:1, 0.6 mL) was added LiOH (4.9 mg, 0.205 mmol). The reaction was allowed to stir at room temperature for 2 hours. The reaction was concentrated, and the residue was purified by chromatography on silica gel using 0->10% MeOH in DCM to afford 33.8 mg white solid as Example 4 (75% yield). LC-MS observed [M+H], 443.18, Calcd. 443.19. $^1$H NMR (400 MHz, DMSO-d6) δ8.76 (d, J=8.5 Hz, 1H), 8.29 (s, 1H), 8.21 (t, J=8.0 Hz, 1H), 8.08 (s, 1H), 8.02 (d, J=7.3 Hz, 2H), 7.87 (d, J=8.2 Hz, 1H), 7.69 (s, 1H), 5.85-5.74 (m, 1H), 5.24 (d, J=3.5 Hz, 2H), 5.04 (t, J=5.6 Hz, 1H), 3.98-3.88 (m, 1H), 3.88-3.74 (m, 1H), 1.91-1.82 (m, 1H), 1.68 (d, J=6.8 Hz, 3H), 0.88-0.81 (m, 2H), 0.76-0.69 (m, 2H).

Example 5: 1-2-(5-(6-(6-isopropoxy-1-oxoisoindolin-2-yl)pyridine-2-yl)-1H-tetrazol-1-yl)propyl acetate

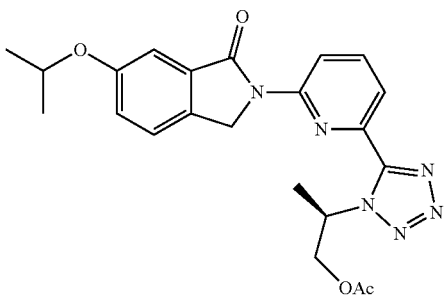 [SMILES: CC(=O)OC[C@@H](C)n1nnnc1-c1cccc(N2Cc3ccc(OC(C)C)cc3C2=O)n1]

Example 5 was prepared by using similar procedure as described for Example 1. LC-MS observed [M+H], 437.18, Calcd. 437.19. $^1$H NMR (400 MHz, DMSO-d6) δ8.75 (dd, J=8.5, 1.0 Hz, 1H), 8.20 (dd, J=8.6, 7.5 Hz, 1H), 8.04 (dd, J=7.6, 0.9 Hz, 1H), 7.64 (d, J=8.1 Hz, 1H), 7.35-7.23 (m, 2H), 5.10 (s, 2H), 4.77 (p, J=6.0 Hz, 1H), 4.63 (dd, J=11.6, 4.1 Hz, 1H), 4.48 (dd, J=11.6, 8.2 Hz, 1H), 1.80 (s, 3H), 1.73 (d, J=6.8 Hz, 3H), 1.32 (d, J=6.0 Hz, 6H).

Example 6: 1-2-(6-(1-(1-hydroxypropan-2-yl)-1H-tetrazol-5-yl)pyridine-2-yl)-6-isopropoxyisoindolin-1-one

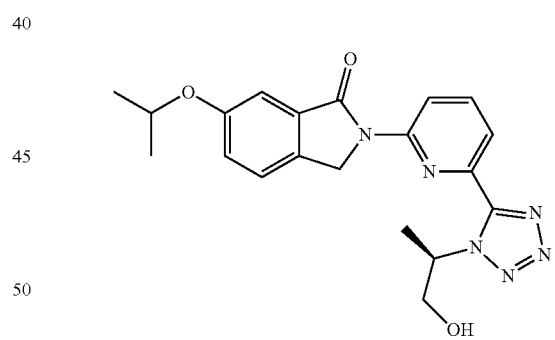

Example 6 was prepared by using similar procedure as described for Example 4. LC-MS observed [M+H], 395.17, Calcd. 395.18. $^1$H NMR (500 MHz, DMSO-d6) δ8.74 (dd, J=8.5, 0.8 Hz, 1H), 8.18 (dd, J=8.6, 7.5 Hz, 1H), 7.99 (dd, J=7.6, 0.9 Hz, 1H), 7.64 (d, J=8.3 Hz, 1H), 7.33-7.25 (m, 2H), 5.83-5.75 (m, 1H), 5.18-5.06 (m, 2H), 5.03 (t, J=5.6 Hz, 1H), 4.77 (p, J=6.0 Hz, 1H), 3.91 (ddd, J=11.1, 8.0, 5.9 Hz, 1H), 3.82 (dt, J=10.8, 5.0 Hz, 1H), 1.66 (d, J=6.7 Hz, 3H), 1.32 (d, J=6.0 Hz, 6H).

The following examples were prepared using procedures similar to those described above:

| Example | Structure | HNMR | ESIMS (M − H)⁻ or (M + H)⁺ |
|---|---|---|---|
| 7 | 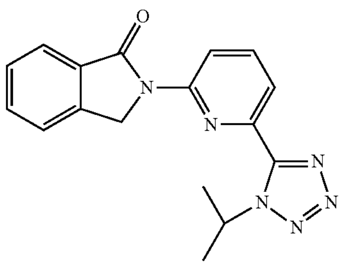 [SMILES: CC(C)n1nnnc1-c1cccc(N2Cc3ccccc3C2=O)n1] | ¹H NMR (400 MHz, Chloroform-d) δ 8.89 (dd, J = 8.4, 0.9 Hz, 1H), 8.12 (dd, J = 7.6, 0.9 Hz, 1H), 8.05-7.95 (m, 2H), 7.71 (td, J = 7.4, 1.2 Hz, 1H), 7.64-7.52 (m, 2H), 5.85 (p, J = 6.8 Hz, 1H), 5.11 (s, 2H), 1.80 (d, J = 6.7 Hz, 6H). | 321.13 |
| 8 | 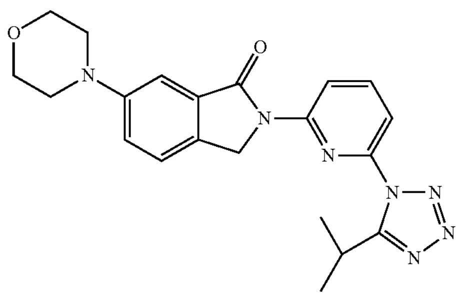 [SMILES: CC(C)c1nnnn1-c1cccc(N2Cc3ccc(N4CCOCC4)cc3C2=O)n1] | ¹H NMR (400 MHz, DMSO-d₆) δ 8.74 (d, J = 8.4 Hz, 1H), 8.25 (t, J = 8.1 Hz, 1H), 7.73 (d, J = 7.7 Hz, 1H), 7.61 (d, J = 8.4 Hz, 1H), 7.41 (dd, J = 8.6, 2.5 Hz, 1H), 7.28 (d, J = 2.4 Hz, 1H), 5.03 (s, 2H), 3.93 (p, J = 6.7 Hz, 1H), 3.78 (t, J = 4.8 Hz, 4H), 3.21 (t, J = 4.9 Hz, 4H), 1.43 (d, J = 6.8 Hz, 6H). | 406.18 |
| 9 | 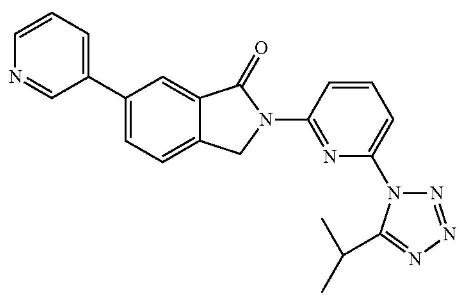 [SMILES: CC(C)c1nnnn1-c1cccc(N2Cc3ccc(-c4cccnc4)cc3C2=O)n1] | ¹H NMR (400 MHz, DMSO-d₆) δ 9.02 (s, 1H), 8.78 (d, J = 8.4 Hz, 1H), 8.64 (d, J = 5.0 Hz, 1H), 8.29 (t, J = 8.1 Hz, 1H), 8.24 (d, J = 7.7 Hz, 1H), 8.18 (s, 1H), 8.13 (d, J = 8.4 Hz, 1H), 7.91 (d, J = 8.0 Hz, 1H), 1.11 (d, J = 1.1 Hz, 1H), 7.55 (dd, J = 8.1, 4.7 Hz, 1H), 5.21 (s, 2H), 4.01-3.80 (m, 1H), 1.45 (d, J = 6.8 Hz, 6H). | 398.15 |
| 10 | 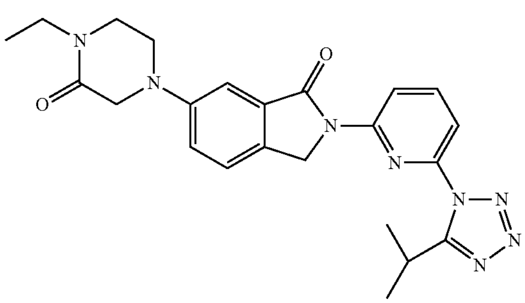 [SMILES: CCN1CCN(c2ccc3c(c2)C(=O)N(c2cccc(-n4nnnc4C(C)C)n2)C3)CC1=O] | ¹H NMR (500 MHz, DMSO-d₆) δ 8.74 (d, J = 8.4 Hz, 1H), 8.25 (t, J = 8.1 Hz, 1H), 7.73 (d, J = 7.7 Hz, 1H), 7.61 (d, J = 8.4 Hz, 1H), 7.39 (dd, J = 8.5, 2.5 Hz, 1H), 7.27 (d, J = 2.4 Hz, 1H), 5.03 (s, 2H), 3.99-3.90 (m, 1H), 3.87 (s, 2H), 3.62-3.57 (m, 2H), 3.48 (t, J = 5.4 Hz, 2H), 3.40 (t, J = 7.2 Hz, 2H), 1.43 (d, J = 6.9 Hz, 6H), 1.08 (t, J = 7.1 Hz, 3H). | 447.21 |
| 11 | 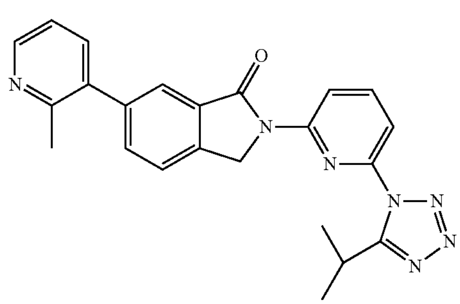 [SMILES: Cc1ncccc1-c1ccc2c(c1)C(=O)N(c1cccc(-n3nnnc3C(C)C)n1)C2] | | 412.17 |

-continued

| Example | Structure | HNMR | ESIMS (M − H)⁻ or (M + H)⁺ |
|---|---|---|---|
| 12 | 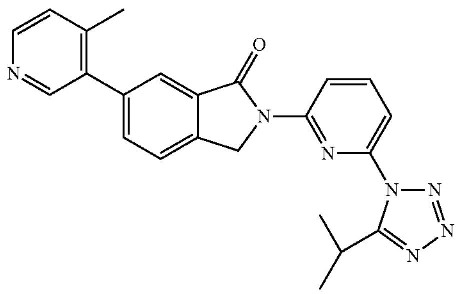 [SMILES: Cc1ccncc1-c1ccc2c(c1)C(=O)N(c1cccc(-n3nnnc3C(C)C)n1)C2] | ¹H NMR (500 MHz, DMSO-d₆) δ 8.76 (d, J = 8.3 Hz, 1H), 8.49 (d, J = 5.0 Hz, 1H), 8.45 (s, 1H), 8.28 (d, J = 8.2 Hz, 1H), 7.88 (d, J = 7.9 Hz, 1H), 7.85 (s, 1H), 7.79 (dd, J = 7.8, 1.7 Hz, 1H), 7.76 (d, J = 7.7 Hz, 1H), 7.40 (d, J = 5.2 Hz, 1H), 5.22 (s, 2H), 3.95 (p, J = 6.9 Hz, 1H), 2.31 (s, 3H), 1.45 (d, J = 6.9 Hz, 6H). | 412.17 |
| 13 | 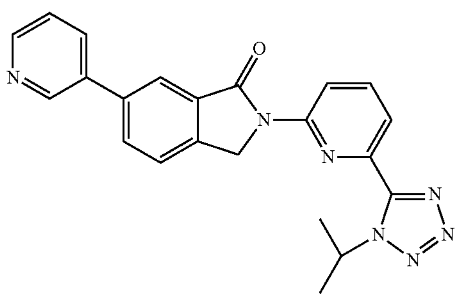 [SMILES: CC(C)n1nnnc1-c1cccc(N2Cc3ccc(-c4cccnc4)cc3C2=O)n1] | ¹H NMR (400 MHz, DMSO-d₆) δ 9.03 (d, J = 2.4 Hz, 1H), 8.80 (dd, J = 8.5, 0.9 Hz, 1H), 8.64 (dd, J = 4.7, 1.6 Hz, 1H), 8.27-8.17 (m, 3H), 8.14 (dd, J = 7.9, 1.8 Hz, 1H), 8.04 (dd, J = 7.5, 0.9 Hz, 1H), 7.92 (d, J = 7.9 Hz, 1H), 7.59-7.51 (m, 1H), 5.85 (p, J = 6.6 Hz, 1H), 5.29 (s, 2H), 1.71 (d, J = 6.6 Hz, 6H). | 398.15 |
| 14 | 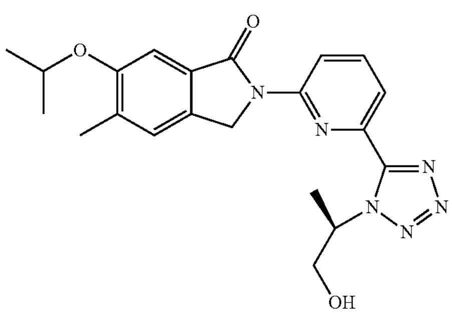 [SMILES: Cc1cc2c(cc1OC(C)C)C(=O)N(c1cccc(-c3nnnn3[C@H](C)CO)n1)C2] | | 409.20 |
| 15 | 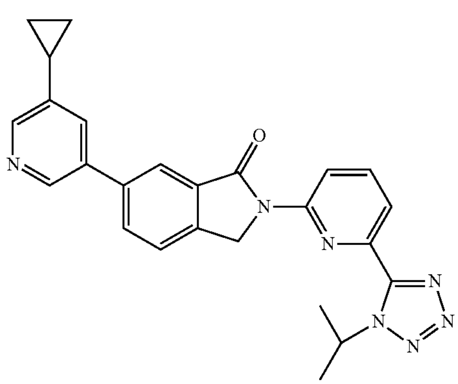 [SMILES: CC(C)n1nnnc1-c1cccc(N2Cc3ccc(-c4cncc(C5CC5)c4)cc3C2=O)n1] | ¹H NMR (400 MHz, DMSO-d₆) δ 8.80 (d, J = 8.5 Hz, 1H), 8.77 (d, J = 2.2 Hz, 1H), 8.46 (d, J = 2.2 Hz, 1H), 8.24-8.18 (m, 2H), 8.13 (dd, J = 7.9, 1.8 Hz, 1H), 8.03 (d, J = 7.5 Hz, 1H), 7.90 (d, J = 8.0 Hz, 1H), 7.80 (t, J = 2.2 Hz, 1H), 5.85 (p, J = 6.6 Hz, 1H), 5.28 (s, 2H), 2.14-2.02 (m, 1H), 1.71 (d, J = 6.6 Hz, 6H), 1.10-1.04 (m, 2H), 0.93 (dd, J = 5.1, 2.2 Hz, 2H). | 438.19 |

| Example | Structure | HNMR | ESIMS (M − H)⁻ or (M + H)⁺ |
|---|---|---|---|
| 16 | 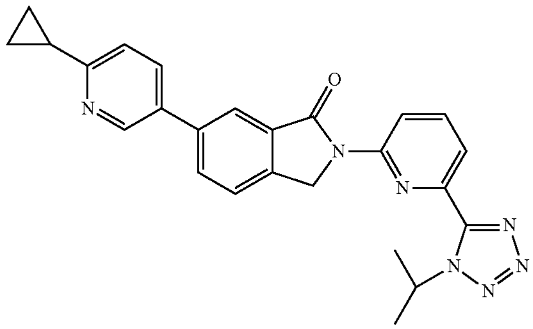 [SMILES: CC(C)n1nnnc1-c1cccc(N2Cc3ccc(-c4ccc(C5CC5)nc4)cc3C2=O)n1] | $^{1}$H NMR (500 MHz, DMSO-$d_6$) δ 8.83 (d, J = 2.4 Hz, 1H), 8.81-8.77 (m, 1H), 8.21 (dd, J = 8.7, 7.6 Hz, 1H), 8.12 (d, J = 1.8 Hz, 1H), 8.08 (dt, J = 8.3, 2.5 Hz, 2H), 8.03 (d, J = 7.6 Hz, 1H), 7.89 (d, J = 7.9 Hz, 1H), 7.43 (d, J = 8.2 Hz, 1H), 5.84 (p, J = 6.6 Hz, 1H), 5.27 (s, 2H), 2.22-2.16 (m, 1H), 1.71 (d, J = 6.6 Hz, 6H), 1.01-0.98 (m, 4H). | 438.19 |

Assays

The ability (IC$_{50}$) of compounds to inhibit ASK1 kinase activity was determined by HTRF® KinEASE™ Assay System ASK1 kinase was from Thermofisher (Catalogue # PV4011), ATP was from Sigma (Catalogue # A7699), HTRF® KinEASE™ Assay System was obtained from Cisbio (Bedford, Mass.). ½ Area plate was from Perkin Elmer (Catalogue #6005560). HTRF® KinEASE™-STK is a generic method for measuring serine/threonine kinase activities using time-resolved fluorescence resonance energy transfer (TR-FRET) immunoassay. The IC$_{50}$ value for each compound was determined in the presence of compound (various concentration from 0 to 10 uM) and a fixed amount of ATP, peptide substrates. Test compound, 1 uM STK3 peptide substrate, 5 nM of ASK1 kinase are incubated with kinase reaction buffer, containing 50 mM HEPES pH 7.5, 0.01% BRIJ-35, 10 mM MgCl2, and 1 mM EGTA for 30 minutes, then 100 uM ATP is added to start kinase reaction and incubated for 3 hours. The STK3-antibody labeled with Eu$^{3+}$-Cryptate and 125 nM streptavidin-XL665 are mixed in a single addition with stop reagents provided by the Cisbio kit used to stop the kinase reaction. Fluorescence is detected using Envision Multilabeled 2014 reader from PerkinElmer. The Fluorescence is measured at 615 nm (Cryptate) and 665 nm (XL665) and a ratio of 665 nm/615 nm is calculated for each well. The resulting TR-FRET is proportional to the phosphorylation level. Staurosporine was used as the positive control. IC$_{50}$ was determined by Xlfit 5.3.

By using above method, the inhibition of ASK1 was tested for the compound of formula (I). IC$_{50}$ ranges are as follows: A<1 nM; 1 nM<10 nM<B<10 nM; 10 nM<C<100 nM; 100 nM<D<1 μM; E>1 μM.

| Example No. | IC$_{50}$ |
|---|---|
| 1 | B |
| 2 | C |
| 3 | D |
| 4 | C |
| 5 | E |
| 6 | B |
| 7 | C |
| 8 | D |
| 9 | C |
| 10 | C |
| 11 | D |
| 12 | D |
| 13 | B |
| 14 | B |
| 15 | C |
| 16 | C |

While this invention has been particularly shown and described with references to preferred embodiments thereof, it will be understood by those skilled in the art that various changes in form and details may be made therein without departing from the scope of the invention encompassed by the appended claims.

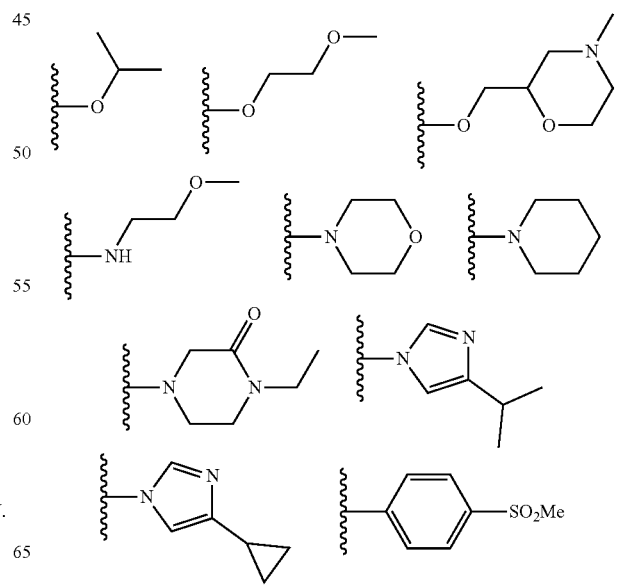

16. The compound of claim 1 wherein $R_5$ is selected from the groups below
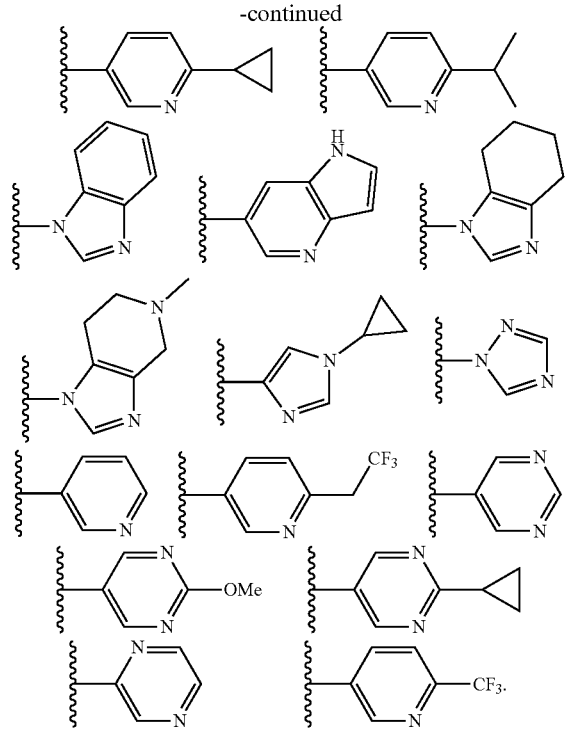
17. The compound of claim 15 wherein $R_5$ is selected from the groups below
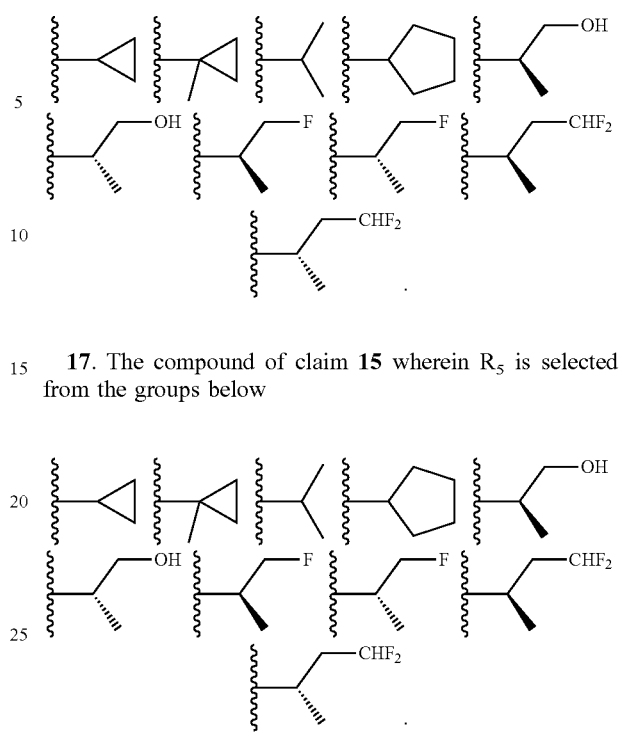

What is claimed:

1. A compound represented by Formula I or a pharmaceutically acceptable salt, ester, or combination thereof:

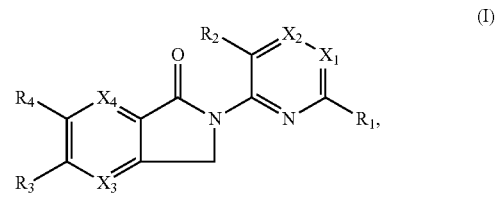

(I)

wherein
R$_1$ is selected from

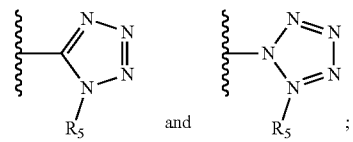

and wherein R$_5$ is selected from the group consisting of:
1) Hydrogen;
2) Optionally substituted —C$_1$-C$_8$ alkyl;
3) Optionally substituted —C$_2$-C$_8$ alkenyl;
4) Optionally substituted —C$_2$-C$_8$ alkynyl;

5) Optionally substituted —$C_3$-$C_8$ cycloalkyl;
6) Optionally substituted aryl;
7) Optionally substituted arylalkyl;
8) Optionally substituted 3- to 8-membered heterocycloalkyl;
9) Optionally substituted heteroaryl; and
10) Optionally substituted heteroarylalkyl;

$X_1$, $X_2$, $X_3$ and $X_4$ are each independently selected from N and $C(R_6)$;

$R_2$ and $R_6$ are each independently selected from the group consisting of:
1) Hydrogen;
2) Halogen;
3) —$NO_2$;
4) Cyano;
5) Optionally substituted —$C_1$-$C_8$ alkyl;
6) Optionally substituted —$C_1$-$C_8$ cycloalkyl; and
7) Optionally substituted 3- to 8-membered heterocycloalkyl;

$R_3$ and $R_4$ are each independently selected from the group consisting of:
1) Hydrogen;
2) Halogen;
3) —$NO_2$;
4) Cyano;
5) Optionally substituted —$C_1$-$C_8$ alkyl;
6) Optionally substituted —$C_2$-$C_8$ alkenyl;
7) Optionally substituted —$C_2$-$C_8$ alkynyl;
8) Optionally substituted —$C_3$-$C_8$ cycloalkyl;
9) Optionally substituted aryl;
10) Optionally substituted arylalkyl;
11) Optionally substituted 3- to 8-membered heterocycloalkyl;
12) Optionally substituted heteroaryl;
13) Optionally substituted heteroarylalkyl;
14) —$OR_7$;
15) —$N(R_7)(R_8)$;
16) —$S(O)_2N(R_7)(R_8)$;
17) —$N(R_7)C(O)R_8$; and
18) —$N(R_7)S(O)_2R_8$;

wherein $R_7$ and $R_8$ are independently selected from the group consisting of hydrogen, —$C_1$-$C_{15}$ alkyl, cycloalkyl, heterocycloalkyl, aryl, and heteroaryl, each of which is optionally substituted with 0 to 3 substituents selected from halo, alkyl, mono- or dialkylamino, alkylamido, arylamido, heteroarylamido, —CN, lower alkoxy, —$CF_3$, aryl, and heteroaryl, or $R_7$ and $R_8$ are taken together with the nitrogen atom to which they are attached to form a heterocyclics;

provided that each optionally substituted group is independently optionally substituted with one or more substituents selected from deuterium, —F, —Cl, —Br, —I, —OH, protected hydroxy, —$NO_2$, —CN, —$NH_2$, $N_3$, protected amino, alkoxy, thioalkoxy, oxo, —$C_1$-$C_{12}$-alkyl, —$C_2$-$C_{12}$-alkenyl, —$C_2$-$C_{12}$-alkynyl, —$C_3$-$C_{12}$-cycloalkyl, -heterocycloalkyl, -halo-$C_1$-$C_{12}$-alkyl, -halo-$C_2$-$C_{12}$-alkenyl, -halo-$C_2$-$C_{12}$-alkynyl, -halo-$C_3$-$C_{12}$-cycloalkyl, —NH—$C_1$-$C_{12}$-alkyl, —NH—$C_2$-$C_{12}$-alkenyl, —NH—$C_2$-$C_{12}$-alkynyl, —NH—$C_3$-$C_{12}$-cycloalkyl, —NH-aryl, —NH-heteroaryl, —NH-heterocycloalkyl, -dialkylamino, -diarylamino, -diheteroarylamino, —O—$C_1$-$C_{12}$-alkyl, —O—$C_2$-$C_{12}$-alkenyl, —O—$C_2$-$C_{12}$-alkynyl, —O—$C_3$-$C_{12}$-cycloalkyl, —O-aryl, —O-heteroaryl, —O-heterocycloalkyl, —C(O)—$C_1$-$C_{12}$-alkyl, —C(O)—$C_2$-$C_{12}$-alkenyl, —C(O)—$C_2$-$C_{12}$-alkynyl, —C(O)—$C_3$-$C_{12}$-cycloalkyl, —C(O)-aryl, —C(O)-heteroaryl, —C(O)-heterocycloalkyl, —$CONH_2$, —CONH—$C_1$-$C_{12}$-alkyl, —CONH—$C_2$-$C_{12}$-alkenyl, —CONH—$C_2$-$C_{12}$-alkynyl, —CONH—$C_3$-$C_{12}$-cycloalkyl, —CONH-aryl, —CONH-heteroaryl, —CONH-heterocycloalkyl, —$OCO_2$—$C_1$-$C_{12}$-alkyl, —$OCO_2$—$C_2$-$C_{12}$-alkenyl, —$OCO_2$—$C_2$-$C_{12}$-alkynyl, —$OCO_2$—$C_3$-$C_{12}$-cycloalkyl, —$OCO_2$-aryl, —$OCO_2$-heteroaryl, —$OCO_2$-heterocycloalkyl, —$OCONH_2$—, —OCONH—$C_1$-$C_{12}$alkyl, —OCONH—$C_2$-$C_{12}$-alkenyl, —OCONH—$C_2$-$C_{12}$-alkynyl, —OCONH—$C_3$-$C_{12}$-cycloalkyl, —OCONH-aryl, —OCONH-heteroaryl, —OCONH-heterocycloalkyl, —NHC(O)—$C_1$-$C_{12}$-alkyl, —NHC(O)—$C_2$-$C_{12}$-alkenyl, —NHC(O)—$C_2$-$C_{12}$-alkynyl, —NHC(O)—$C_3$-$C_{12}$-cycloalkyl, —NHC(O)-aryl, —NHC(O)-heteroaryl, —NHC(O)-heterocycloalkyl, —$NHCO_2$—$C_1$-$C_{12}$-alkyl, —$NHCO_2$—$C_2$-$C_{12}$-alkenyl, —$NHCO_2$—$C_2$-$C_{12}$-alkynyl, —$NHCO_2$—$C_3$-$C_{12}$-cycloalkyl, —$NHCO_2$-aryl, —$NHCO_2$-heteroaryl, —$NHCO_2$-heterocycloalkyl, —$NHC(O)NH_2$, —NHC(O)NH—$C_1$-$C_{12}$alkyl, —NHC(O)NH—$C_2$-$C_{12}$-alkenyl, —NHC(O)NH—$C_2$-$C_{12}$-alkynyl, —NHC(O)NH—$C_3$-$C_{12}$-cycloalkyl, —NHC(O)NH-aryl, —NHC(O)NH-heteroaryl, —NHC(O)NH-heterocycloalkyl, $NHC(S)NH_2$, —NHC(S)NH—$C_1$-$C_{12}$—NHC(S)NH—$C_2$-$C_{12}$-alkenyl, —NHC(S)NH—$C_2$-$C_{12}$-alkynyl, —NHC(S)NH—$C_3$-$C_{12}$-cycloalkyl, —NHC(S)NH-aryl, —NHC(S)NH-heteroaryl, —NHC(S)NH-heterocycloalkyl, —$NHC(NH)NH_2$, —NHC(NH)NH—$C_1$-$C_{12}$-alkyl, —NHC(NH)NH—$C_2$-$C_{12}$-alkenyl, —NHC(NH)NH—$C_2$-$C_{12}$-alkynyl, —NHC(NH)NH—$C_3$-$C_{12}$-cycloalkyl, —NHC(NH)NH-aryl, —NHC(NH)NH-heteroaryl, —NHC(NH)NH-heterocycloalkyl, —NHC(NH)—$C_1$-$C_{12}$-alkyl, —NHC(NH)—$C_2$-$C_{12}$-alkenyl, —NHC(NH)—$C_2$-$C_{12}$-alkynyl, —NHC(NH)—$C_3$-$C_{12}$-cycloalkyl, —NHC(NH)-aryl, —NHC(NH)-heteroaryl, —NHC(NH)-heterocycloalkyl, —C(NH)NH—$C_1$-$C_{12}$-alkyl, —C(NH)NH—$C_2$-$C_{12}$-alkenyl, —C(NH)NH—$C_2$-$C_{12}$-alkynyl, —C(NH)NH—$C_3$-$C_{12}$-cycloalkyl, —C(NH)NH-aryl, —C(NH)NH-heteroaryl, —C(NH)NH-heterocycloalkyl, —S(O)—$C_1$-$C_{12}$-alkyl, —S(O)—$C_2$-$C_{12}$-alkenyl, —S(O)—$C_2$-$C_{12}$-alkenyl, —S(O)—$C_3$-$C_{12}$-cycloalkyl, —S(O)-aryl, —S(O)-heteroaryl, —S(O)-heterocycloalkyl-$SO_2NH_2$, —$SO_2NH$—$C_1$-$C_{12}$-alkyl, —$SO_2NH$—$C_2$-$C_{12}$-alkenyl, —$SO_2NH$—$C_2$-$C_{12}$-alkynyl, —$SO_2NH$—$C_3$-$C_{12}$-cycloalkyl, —$SO_2NH$-aryl, —$SO_2NH$-heteroaryl, —$SO_2NH$-heterocycloalkyl, —$NHSO_2$—$C_1$-$C_{12}$-alkyl, —$NHSO_2$—$C_2$-$C_{12}$-alkenyl, —$NHSO_2$—$C_2$-$C_{12}$-alkynyl, —$NHSO_2$—$C_3$-$C_{12}$-cycloalkyl, —$NHSO_2$-aryl, —$NHSO_2$-heteroaryl, —$NHSO_2$-heterocycloalkyl, —$CH_2NH_2$, —$CH_2SO_2CH_3$, -aryl, -arylalkyl, -heteroaryl, -heteroarylalkyl, -heterocycloalkyl, —$C_3$-$C_{12}$-cycloalkyl, polyalkoxyalkyl, polyalkoxy, -methoxymethoxy, -methoxyethoxy, —SH, —S—$C_1$-$C_{12}$-alkyl, —S—$C_2$-$C_{12}$-alkenyl, —S—$C_2$-$C_{12}$-alkynyl, —S—$C_3$-$C_{12}$-cycloalkyl, —S-aryl, —S-heteroaryl, —S-heterocycloalkyl, methylthiomethyl, and -L'-R', wherein L' is $C_1$-$C_6$alkylene, $C_2$-$C_6$alkenylene or $C_2$-$C_6$alkynylene, and R' is aryl, heteroaryl, heterocyclic, $C_3$-$C_{12}$cycloalkyl or $C_3$-$C_{12}$cycloalkenyl.

2. The compound of claim 1, represented by Formula (II) or a pharmaceutically acceptable salt, ester or combination thereof:

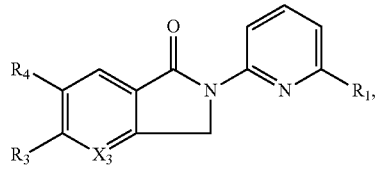

(II)

wherein $R_1$, $R_3$, $R_4$ and $X_3$ are as defined in claim 1.

3. The compound of claim 1, represented by Formula (IIIa) or Formula (IIIb), or a pharmaceutically acceptable salt, ester or combination thereof:

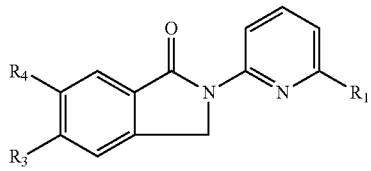

(IIIa)

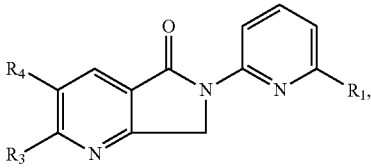

(IIIb)

wherein $R_1$, $R_3$, and $R_4$ are as defined in claim 1.

4. The compound of claim 1, represented by Formula (IVa), (IVb), (Va), or (Vb), or a pharmaceutically acceptable salt, ester or combination thereof:

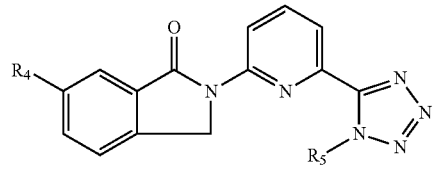

(IVa)

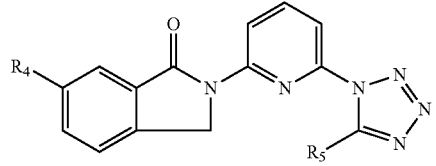

(IVb)

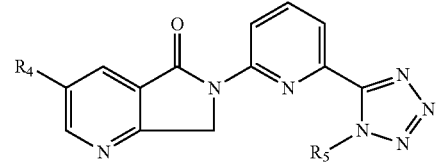

(Va)

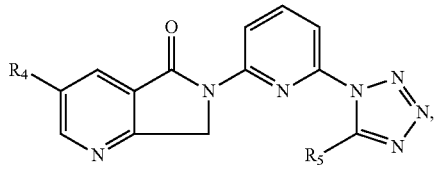

(Vb)

wherein $R_4$ and $R_5$ are as defined in claim 1.

5. The compound according to claim 1, which is selected from compounds of Formula (IVa) or a pharmaceutically acceptable salt, ester or combination thereof:

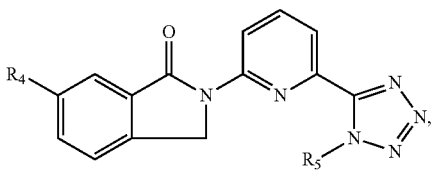

(IVa)

wherein $R^1$ and $R^2$ are delineated for each compound in Table 1,

TABLE 1

| compound | $R_5$ | $R_4$ |
|---|---|---|
| 1 | cyclopropyl | O-isopropyl |
| 2 | 1-methylcyclopropyl | O-isopropyl |
| 3 | isopropyl | O-isopropyl |
| 4 | cyclopentyl | O-isopropyl |
| 5 | (S)-CH(CH3)CH2OH | O-isopropyl |
| 6 | (R)-CH(CH3)CH2OH | O-isopropyl |
| 7 | (S)-CH(CH3)CH2F | O-isopropyl |
| 8 | (R)-CH(CH3)CH2F | O-isopropyl |

TABLE 1-continued

| compound | R₅ | R₄ |
|---|---|---|
| 9 | CHF₂, (R) | O-iPr |
| 10 | CHF₂, (S) | O-iPr |
| 11 | cyclopropyl | -O-CH₂CH₂-O-CH₃ |
| 12 | 1-methylcyclopropyl | -O-CH₂CH₂-O-CH₃ |
| 13 | isopropyl | -O-CH₂CH₂-O-CH₃ |
| 14 | cyclopentyl | -O-CH₂CH₂-O-CH₃ |
| 15 | CH₂OH, CH₃ (R) | -O-CH₂CH₂-O-CH₃ |
| 16 | CH₂OH, CH₃ (S) | -O-CH₂CH₂-O-CH₃ |
| 17 | CH₂F, CH₃ (R) | -O-CH₂CH₂-O-CH₃ |
| 18 | CH₂F, CH₃ (S) | -O-CH₂CH₂-O-CH₃ |
| 19 | CHF₂, CH₃ (R) | -O-CH₂CH₂-O-CH₃ |
| 20 | CHF₂, CH₃ (S) | -O-CH₂CH₂-O-CH₃ |
| 21 | cyclopropyl | 4-methylmorpholin-2-ylmethoxy |
| 22 | 1-methylcyclopropyl | 4-methylmorpholin-2-ylmethoxy |
| 23 | isopropyl | 4-methylmorpholin-2-ylmethoxy |
| 24 | cyclopentyl | 4-methylmorpholin-2-ylmethoxy |
| 25 | CH₂OH, CH₃ (R) | 4-methylmorpholin-2-ylmethoxy |
| 26 | CH₂OH, CH₃ (S) | 4-methylmorpholin-2-ylmethoxy |
| 27 | CH₂F, CH₃ (R) | 4-methylmorpholin-2-ylmethoxy |
| 28 | CH₂F, CH₃ (S) | 4-methylmorpholin-2-ylmethoxy |
| 29 | CHF₂, CH₃ (R) | 4-methylmorpholin-2-ylmethoxy |
| 30 | CHF₂, CH₃ (S) | 4-methylmorpholin-2-ylmethoxy |

TABLE 1-continued

| compound | R₅ | R₄ |
|---|---|---|
| 31 | cyclopropyl | 4-cyclopropyl-imidazol-1-yl |
| 32 | 1-methylcyclopropyl | 4-cyclopropyl-imidazol-1-yl |
| 33 | isopropyl | 4-cyclopropyl-imidazol-1-yl |
| 34 | cyclopentyl | 4-cyclopropyl-imidazol-1-yl |
| 35 | (S)-2-methyl-3-hydroxypropyl | 4-cyclopropyl-imidazol-1-yl |
| 36 | (R)-2-methyl-3-hydroxypropyl | 4-cyclopropyl-imidazol-1-yl |
| 37 | (S)-2-methyl-3-fluoropropyl | 4-cyclopropyl-imidazol-1-yl |
| 38 | (R)-2-methyl-3-fluoropropyl | 4-cyclopropyl-imidazol-1-yl |
| 39 | (S)-1-methyl-2,2-difluoroethyl | 4-cyclopropyl-imidazol-1-yl |
| 40 | (R)-1-methyl-2,2-difluoroethyl | 4-cyclopropyl-imidazol-1-yl |
| 41 | cyclopropyl | morpholin-4-yl |

TABLE 1-continued

| compound | R₅ | R₄ |
|---|---|---|
| 42 | 1-methylcyclopropyl | morpholin-4-yl |
| 43 | isopropyl | morpholin-4-yl |
| 44 | cyclopentyl | morpholin-4-yl |
| 45 | (S)-2-methyl-3-hydroxypropyl | morpholin-4-yl |
| 46 | (R)-2-methyl-3-hydroxypropyl | morpholin-4-yl |
| 47 | (S)-2-methyl-3-fluoropropyl | morpholin-4-yl |
| 48 | (R)-2-methyl-3-fluoropropyl | morpholin-4-yl |
| 49 | (S)-1-methyl-2,2-difluoroethyl | morpholin-4-yl |
| 50 | (R)-1-methyl-2,2-difluoroethyl | morpholin-4-yl |
| 51 | cyclopropyl | piperidin-1-yl |
| 52 | 1-methylcyclopropyl | piperidin-1-yl |
| 53 | isopropyl | piperidin-1-yl |
| 54 | cyclopentyl | piperidin-1-yl |
| 55 | (S)-2-methyl-3-hydroxypropyl | piperidin-1-yl |

TABLE 1-continued

| compound | R₅ | R₄ |
|---|---|---|
| 56 | CH(CH₃)CH₂OH | piperidin-1-yl |
| 57 | CH(CH₃)CH₂F (wedge) | piperidin-1-yl |
| 58 | CH(CH₃)CH₂F (dash) | piperidin-1-yl |
| 59 | CH(CH₃)CHF₂ (wedge) | piperidin-1-yl |
| 60 | CH(CH₃)CHF₂ (dash) | piperidin-1-yl |
| 61 | cyclopropyl | 4-ethyl-3-oxopiperazin-1-yl |
| 62 | 1-methylcyclopropyl | 4-ethyl-3-oxopiperazin-1-yl |
| 63 | isopropyl | 4-ethyl-3-oxopiperazin-1-yl |
| 64 | cyclopentyl | 4-ethyl-3-oxopiperazin-1-yl |
| 65 | CH(CH₃)CH₂OH (wedge) | 4-ethyl-3-oxopiperazin-1-yl |
| 66 | CH(CH₃)CH₂OH (dash) | 4-ethyl-3-oxopiperazin-1-yl |
| 67 | CH(CH₃)CH₂F (wedge) | 4-ethyl-3-oxopiperazin-1-yl |
| 68 | CH(CH₃)CH₂F (dash) | 4-ethyl-3-oxopiperazin-1-yl |
| 69 | CH(CH₃)CHF₂ (wedge) | 4-ethyl-3-oxopiperazin-1-yl |
| 70 | CH(CH₃)CHF₂ (dash) | 4-ethyl-3-oxopiperazin-1-yl |
| 71 | cyclopropyl | 1-cyclopropyl-1H-imidazol-4-yl |
| 72 | 1-methylcyclopropyl | 1-cyclopropyl-1H-imidazol-4-yl |
| 73 | isopropyl | 1-cyclopropyl-1H-imidazol-4-yl |
| 74 | cyclopentyl | 1-cyclopropyl-1H-imidazol-4-yl |
| 75 | CH(CH₃)CH₂OH (wedge) | 1-cyclopropyl-1H-imidazol-4-yl |
| 76 | CH(CH₃)CH₂OH (dash) | 1-cyclopropyl-1H-imidazol-4-yl |
| 77 | CH(CH₃)CH₂F (wedge) | 1-cyclopropyl-1H-imidazol-4-yl |
| 78 | CH(CH₃)CH₂F (dash) | 1-cyclopropyl-1H-imidazol-4-yl |

TABLE 1-continued

| compound | R₅ | R₄ |
|---|---|---|
| 79 | (S)-CHF₂-CH(CH₃)- | 1-cyclopropyl-imidazol-4-yl |
| 80 | (R)-CHF₂-CH(CH₃)- | 1-cyclopropyl-imidazol-4-yl |
| 81 | cyclopropyl | 6-cyclopropyl-pyridin-3-yl |
| 82 | 1-methyl-cyclopropyl | 4-cyclopropyl-pyridin-2-yl |
| 83 | isobutyl | 6-cyclopropyl-pyridin-3-yl |
| 84 | cyclopentyl | 6-cyclopropyl-pyridin-3-yl |
| 85 | (S)-HOCH₂-CH(CH₃)- | 6-cyclopropyl-pyridin-3-yl |
| 86 | (R)-HOCH₂-CH(CH₃)- | 6-cyclopropyl-pyridin-3-yl |
| 87 | (S)-FCH₂-CH(CH₃)- | 6-cyclopropyl-pyridin-3-yl |
| 88 | (R)-FCH₂-CH(CH₃)- | 6-cyclopropyl-pyridin-3-yl |
| 89 | (S)-CHF₂-CH(CH₃)- | 6-cyclopropyl-pyridin-3-yl |
| 90 | (R)-CHF₂-CH(CH₃)- | 5-cyclopropyl-pyridin-2-yl |
| 91 | cyclopropyl | 5-methyl-4,5,6,7-tetrahydroimidazo[4,5-c]pyridine |

TABLE 1-continued

| compound | R₅ | R₄ |
|---|---|---|
| 92 | 1-methyl-cyclopropyl | 5-methyl-4,5,6,7-tetrahydroimidazo[4,5-c]pyridine |
| 93 | isobutyl | 5-methyl-4,5,6,7-tetrahydroimidazo[4,5-c]pyridine |
| 94 | cyclopentyl | 5-methyl-4,5,6,7-tetrahydroimidazo[4,5-c]pyridine |
| 95 | (S)-HOCH₂-CH(CH₃)- | 5-methyl-4,5,6,7-tetrahydroimidazo[4,5-c]pyridine |
| 96 | (R)-HOCH₂-CH(CH₃)- | 5-methyl-4,5,6,7-tetrahydroimidazo[4,5-c]pyridine |
| 97 | (S)-FCH₂-CH(CH₃)- | 5-methyl-4,5,6,7-tetrahydroimidazo[4,5-c]pyridine |
| 98 | (R)-FCH₂-CH(CH₃)- | 5-methyl-4,5,6,7-tetrahydroimidazo[4,5-c]pyridine |
| 99 | (R)-CHF₂-CH(CH₃)- | 5-methyl-4,5,6,7-tetrahydroimidazo[4,5-c]pyridine |

TABLE 1-continued

| compound | R5 | R4 |
|---|---|---|
| 100 | (S)-CHF2-CH(CH3)- | 5-methyl-4,5,6,7-tetrahydroimidazo[4,5-c]pyridin-1-yl |

6. The compound according to claim 1, which is selected from compounds of Formula (IVb) or a pharmaceutically acceptable salt, ester or combination thereof:

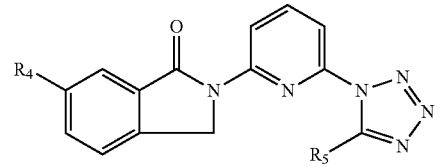

(IVb)

wherein $R^1$ and $R^2$ are delineated for each compound in Table 2,

TABLE 2

| compound | R5 | R4 |
|---|---|---|
| 101 | cyclopropyl | O-iPr |
| 102 | 1-methylcyclopropyl | O-iPr |
| 103 | isopropyl | O-iPr |
| 104 | cyclopentyl | O-iPr |
| 105 | (S)-HOCH2-CH(CH3)- | O-iPr |
| 106 | (R)-HOCH2-CH(CH3)- | O-iPr |
| 107 | (S)-FCH2-CH(CH3)- | O-iPr |
| 108 | (R)-FCH2-CH(CH3)- | O-iPr |

TABLE 2-continued

| compound | R5 | R4 |
|---|---|---|
| 109 | (S)-CHF2-CH(CH3)- | O-iPr |
| 110 | (R)-CHF2-CH(CH3)- | O-iPr |
| 111 | cyclopropyl | OCH2CH2OCH3 |
| 112 | 1-methylcyclopropyl | OCH2CH2OCH3 |
| 113 | isopropyl | OCH2CH2OCH3 |
| 114 | cyclopentyl | OCH2CH2OCH3 |
| 115 | (S)-HOCH2-CH(CH3)- | OCH2CH2OCH3 |
| 116 | (R)-HOCH2-CH(CH3)- | OCH2CH2OCH3 |
| 117 | (S)-FCH2-CH(CH3)- | OCH2CH2OCH3 |
| 118 | (R)-FCH2-CH(CH3)- | OCH2CH2OCH3 |
| 119 | (S)-CHF2-CH(CH3)- | OCH2CH2OCH3 |
| 120 | (R)-CHF2-CH(CH3)- | OCH2CH2OCH3 |
| 121 | cyclopropyl | (4-methylmorpholin-2-yl)methoxy |

TABLE 2-continued

| compound | R₅ | R₄ |
|---|---|---|
| 122 | 1-methylcyclopropyl | (N-methylmorpholin-2-yl)methoxy |
| 123 | isopropyl | (N-methylmorpholin-2-yl)methoxy |
| 124 | cyclopentyl | (N-methylmorpholin-2-yl)methoxy |
| 125 | (S)-2-methyl-3-hydroxypropyl | (N-methylmorpholin-2-yl)methoxy |
| 126 | (R)-2-methyl-3-hydroxypropyl | (N-methylmorpholin-2-yl)methoxy |
| 127 | (S)-2-methyl-3-fluoropropyl | (N-methylmorpholin-2-yl)methoxy |
| 128 | (R)-2-methyl-3-fluoropropyl | (N-methylmorpholin-2-yl)methoxy |
| 129 | (S)-1-difluoromethyl-ethyl | (N-methylmorpholin-2-yl)methoxy |
| 130 | (R)-1-difluoromethyl-ethyl | (N-methylmorpholin-2-yl)methoxy |
| 131 | cyclopropyl | 4-cyclopropyl-imidazol-1-yl |
| 132 | 1-methylcyclopropyl | 4-cyclopropyl-imidazol-1-yl |
| 133 | isopropyl | 4-cyclopropyl-imidazol-1-yl |
| 134 | cyclopentyl | 4-cyclopropyl-imidazol-1-yl |
| 135 | (S)-2-methyl-3-hydroxypropyl | 4-cyclopropyl-imidazol-1-yl |
| 136 | (R)-2-methyl-3-hydroxypropyl | 4-cyclopropyl-imidazol-1-yl |
| 137 | (S)-2-methyl-3-fluoropropyl | 4-cyclopropyl-imidazol-1-yl |
| 138 | (R)-2-methyl-3-fluoropropyl | 4-cyclopropyl-imidazol-1-yl |
| 139 | (S)-1-difluoromethyl-ethyl | 4-cyclopropyl-imidazol-1-yl |
| 140 | (R)-1-difluoromethyl-ethyl | 4-cyclopropyl-imidazol-1-yl |
| 141 | cyclopropyl | morpholin-4-yl |

TABLE 2-continued

| compound | R₅ | R₄ |
|---|---|---|
| 142 | 1-methylcyclopropyl | morpholino |
| 143 | isopropyl | morpholino |
| 144 | cyclopentyl | morpholino |
| 145 | (S)-1-hydroxymethyl-ethyl (CH₂OH with CH₃ wedge) | morpholino |
| 146 | (R)-1-hydroxymethyl-ethyl (CH₂OH with CH₃ dash) | morpholino |
| 147 | (S)-1-fluoromethyl-ethyl (CH₂F with CH₃ wedge) | morpholino |
| 148 | (R)-1-fluoromethyl-ethyl (CH₂F with CH₃ dash) | morpholino |
| 149 | (S)-1-(difluoromethyl)ethyl (CHF₂ with CH₃ wedge) | morpholino |
| 150 | (R)-1-(difluoromethyl)ethyl (CHF₂ with CH₃ dash) | morpholino |
| 151 | cyclopropyl | piperidino |
| 152 | 1-methylcyclopropyl | piperidino |
| 153 | isopropyl | piperidino |
| 154 | cyclopentyl | piperidino |
| 155 | (S)-1-hydroxymethyl-ethyl | piperidino |
| 156 | (R)-1-hydroxymethyl-ethyl | piperidino |
| 157 | (S)-1-fluoromethyl-ethyl | piperidino |
| 158 | (R)-1-fluoromethyl-ethyl | piperidino |
| 159 | (S)-1-(difluoromethyl)ethyl | piperidino |
| 160 | (R)-1-(difluoromethyl)ethyl | piperidino |
| 161 | cyclopropyl | 4-ethyl-3-oxopiperazin-1-yl |
| 162 | 1-methylcyclopropyl | 4-ethyl-3-oxopiperazin-1-yl |
| 163 | isopropyl | 4-ethyl-3-oxopiperazin-1-yl |
| 164 | cyclopentyl | 4-ethyl-3-oxopiperazin-1-yl |
| 165 | (S)-1-hydroxymethyl-ethyl | 4-ethyl-3-oxopiperazin-1-yl |
| 166 | (R)-1-hydroxymethyl-ethyl | 4-ethyl-3-oxopiperazin-1-yl |
| 167 | (S)-1-fluoromethyl-ethyl | 4-ethyl-3-oxopiperazin-1-yl |

TABLE 2-continued

| compound | R₅ | R₄ |
|---|---|---|
| 168 | CH₂F (methyl, wedge) | piperazinone N-ethyl |
| 169 | CHF₂ (methyl, wedge) | piperazinone N-ethyl |
| 170 | CHF₂ (methyl, dashed) | piperazinone N-ethyl |
| 171 | cyclopropyl | N-cyclopropyl imidazole |
| 172 | 1-methylcyclopropyl | N-cyclopropyl imidazole |
| 173 | isopropyl | N-cyclopropyl imidazole |
| 174 | cyclopentyl | N-cyclopropyl imidazole |
| 175 | CH₂OH (methyl, wedge) | N-cyclopropyl imidazole |
| 176 | CH₂OH (methyl, dashed) | N-cyclopropyl imidazole |
| 177 | CH₂F (methyl, wedge) | N-cyclopropyl imidazole |

TABLE 2-continued

| compound | R₅ | R₄ |
|---|---|---|
| 178 | CH₂F (methyl, dashed) | N-cyclopropyl imidazole |
| 179 | CHF₂ (methyl, wedge) | N-cyclopropyl imidazole |
| 180 | CHF₂ (methyl, dashed) | N-cyclopropyl imidazole |
| 181 | cyclopropyl | 2-cyclopropylpyridin-5-yl |
| 182 | 1-methylcyclopropyl | 2-cyclopropylpyridin-5-yl |
| 183 | isopropyl | 2-cyclopropylpyridin-5-yl |
| 184 | cyclopentyl | 2-cyclopropylpyridin-5-yl |
| 185 | CH₂OH (methyl, wedge) | 2-cyclopropylpyridin-5-yl |
| 186 | CH₂OH (methyl, dashed) | 2-cyclopropylpyridin-5-yl |
| 187 | CH₂F (methyl, wedge) | 2-cyclopropylpyridin-5-yl |
| 188 | CH₂F (methyl, dashed) | 2-cyclopropylpyridin-5-yl |
| 189 | CHF₂ (methyl, wedge) | 2-cyclopropylpyridin-5-yl |
| 190 | CHF₂ (methyl, dashed) | 2-cyclopropylpyridin-5-yl |

TABLE 2-continued

| compound | R₅ | R₄ |
|---|---|---|
| 191 | cyclopropyl | N-methyl-tetrahydroimidazo[4,5-c]pyridine |
| 192 | 1-methylcyclopropyl | N-methyl-tetrahydroimidazo[4,5-c]pyridine |
| 193 | isopropyl | N-methyl-tetrahydroimidazo[4,5-c]pyridine |
| 194 | cyclopentyl | N-methyl-tetrahydroimidazo[4,5-c]pyridine |
| 195 | (S)-2-methyl-3-hydroxypropyl | N-methyl-tetrahydroimidazo[4,5-c]pyridine |
| 196 | (R)-2-methyl-3-hydroxypropyl | N-methyl-tetrahydroimidazo[4,5-c]pyridine |
| 197 | (S)-1-fluoro-2-methylpropyl | N-methyl-tetrahydroimidazo[4,5-c]pyridine |
| 198 | (R)-1-fluoro-2-methylpropyl | N-methyl-tetrahydroimidazo[4,5-c]pyridine |
| 199 | (S)-1-(difluoromethyl)ethyl | N-methyl-tetrahydroimidazo[4,5-c]pyridine |
| 200 | (R)-1-(difluoromethyl)ethyl | N-methyl-tetrahydroimidazo[4,5-c]pyridine |

7. The compound according to claim 1, which is selected from compounds of Formula (Va) or a pharmaceutically acceptable salt, ester or combination thereof:

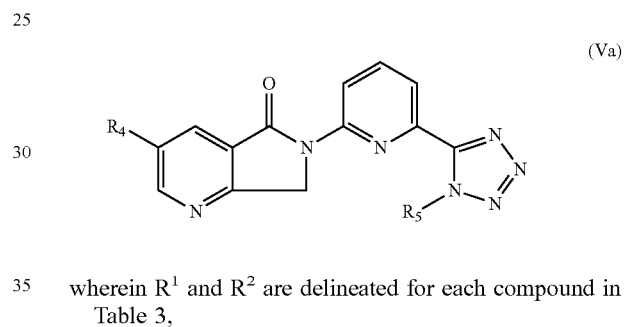

(Va)

wherein R¹ and R² are delineated for each compound in Table 3,

TABLE 3

| compound | R₅ | R₄ |
|---|---|---|
| 201 | cyclopropyl | O-isopropyl |
| 202 | 1-methylcyclopropyl | O-isopropyl |
| 203 | isopropyl | O-isopropyl |
| 204 | cyclopentyl | O-isopropyl |
| 205 | (S)-2-methyl-3-hydroxypropyl | O-isopropyl |
| 206 | (R)-2-methyl-3-hydroxypropyl | O-isopropyl |

TABLE 3-continued

| compound | R₅ | R₄ |
|---|---|---|
| 207 | (S)-CH₂F isopropyl | O-iPr |
| 208 | (R)-CH₂F isopropyl | O-iPr |
| 209 | (S)-CHF₂ isopropyl | O-iPr |
| 210 | (R)-CHF₂ isopropyl | O-iPr |
| 211 | cyclopropyl | OCH₂CH₂OCH₃ |
| 212 | 1-methylcyclopropyl | OCH₂CH₂OCH₃ |
| 213 | isopropyl | OCH₂CH₂OCH₃ |
| 214 | cyclopentyl | OCH₂CH₂OCH₃ |
| 215 | (S)-CH₂OH isopropyl | OCH₂CH₂OCH₃ |
| 216 | (R)-CH₂OH isopropyl | OCH₂CH₂OCH₃ |
| 217 | (S)-CH₂F isopropyl | OCH₂CH₂OCH₃ |
| 218 | (R)-CH₂F isopropyl | OCH₂CH₂OCH₃ |
| 219 | (S)-CHF₂ isopropyl | OCH₂CH₂OCH₃ |
| 220 | (R)-CHF₂ isopropyl | OCH₂CH₂OCH₃ |

TABLE 3-continued

| compound | R₅ | R₄ |
|---|---|---|
| 221 | cyclopropyl | (N-methylmorpholin-2-yl)methoxy |
| 222 | 1-methylcyclopropyl | (N-methylmorpholin-2-yl)methoxy |
| 223 | isopropyl | (N-methylmorpholin-2-yl)methoxy |
| 224 | cyclopentyl | (N-methylmorpholin-2-yl)methoxy |
| 225 | (S)-CH₂OH isopropyl | (N-methylmorpholin-2-yl)methoxy |
| 226 | (R)-CH₂OH isopropyl | (N-methylmorpholin-2-yl)methoxy |
| 227 | (S)-CH₂F isopropyl | (N-methylmorpholin-2-yl)methoxy |
| 228 | (R)-CH₂F isopropyl | (N-methylmorpholin-2-yl)methoxy |
| 229 | (S)-CHF₂ isopropyl | (N-methylmorpholin-2-yl)methoxy |

TABLE 3-continued

| compound | R5 | R4 |
|---|---|---|
| 230 | CHF2, methyl (stereo) | N-methylmorpholine-CH2O- |
| 231 | cyclopropyl | 4-cyclopropyl-1H-imidazol-1-yl |
| 232 | 1-methylcyclopropyl | 4-cyclopropyl-1H-imidazol-1-yl |
| 233 | isopropyl | 4-cyclopropyl-1H-imidazol-1-yl |
| 234 | cyclopentyl | 4-cyclopropyl-1H-imidazol-1-yl |
| 235 | CH2OH, methyl (stereo) | 4-cyclopropyl-1H-imidazol-1-yl |
| 236 | CH2OH, methyl (stereo) | 4-cyclopropyl-1H-imidazol-1-yl |
| 237 | CH2F, methyl (stereo) | 4-cyclopropyl-1H-imidazol-1-yl |
| 238 | CH2F, methyl (stereo) | 4-cyclopropyl-1H-imidazol-1-yl |
| 239 | CHF2, methyl (stereo) | 4-cyclopropyl-1H-imidazol-1-yl |

TABLE 3-continued

| compound | R5 | R4 |
|---|---|---|
| 240 | CHF2, methyl (stereo) | 4-cyclopropyl-1H-imidazol-1-yl |
| 241 | cyclopropyl | morpholin-4-yl |
| 242 | 1-methylcyclopropyl | morpholin-4-yl |
| 243 | isopropyl | morpholin-4-yl |
| 244 | cyclopentyl | morpholin-4-yl |
| 245 | CH2OH, methyl (stereo) | morpholin-4-yl |
| 246 | CH2OH, methyl (stereo) | morpholin-4-yl |
| 247 | CH2F, methyl (stereo) | morpholin-4-yl |
| 248 | CH2F, methyl (stereo) | morpholin-4-yl |
| 249 | CHF2, methyl (stereo) | morpholin-4-yl |
| 250 | CHF2, methyl (stereo) | morpholin-4-yl |
| 251 | cyclopropyl | piperidin-1-yl |
| 252 | 1-methylcyclopropyl | piperidin-1-yl |
| 253 | isopropyl | piperidin-1-yl |

TABLE 3-continued

| compound | R₅ | R₄ |
|---|---|---|
| 254 | cyclopentyl | piperidin-1-yl |
| 255 | -CH(CH₃)CH₂OH | piperidin-1-yl |
| 256 | -CH(CH₃)CH₂OH (other stereo) | piperidin-1-yl |
| 257 | -CH(CH₃)CH₂F | piperidin-1-yl |
| 258 | -CH(CH₃)CH₂F (other stereo) | piperidin-1-yl |
| 259 | -CH(CH₃)CHF₂ | piperidin-1-yl |
| 260 | -CH(CH₃)CHF₂ (other stereo) | piperidin-1-yl |
| 261 | cyclopropyl | 4-ethyl-3-oxopiperazin-1-yl |
| 262 | 1-methylcyclopropyl | 4-ethyl-3-oxopiperazin-1-yl |
| 263 | isopropyl | 4-ethyl-3-oxopiperazin-1-yl |
| 264 | cyclopentyl | 4-ethyl-3-oxopiperazin-1-yl |
| 265 | -CH(CH₃)CH₂OH | 4-ethyl-3-oxopiperazin-1-yl |
| 266 | -CH(CH₃)CH₂OH (other stereo) | 4-ethyl-3-oxopiperazin-1-yl |
| 267 | -CH(CH₃)CH₂F | 4-ethyl-3-oxopiperazin-1-yl |
| 268 | -CH(CH₃)CH₂F (other stereo) | 4-ethyl-3-oxopiperazin-1-yl |
| 269 | -CH(CH₃)CHF₂ | 4-ethyl-3-oxopiperazin-1-yl |
| 270 | -CH(CH₃)CHF₂ (other stereo) | 4-ethyl-3-oxopiperazin-1-yl |
| 271 | cyclopropyl | 1-cyclopropyl-1H-imidazol-4-yl |
| 272 | 1-methylcyclopropyl | 1-cyclopropyl-1H-imidazol-4-yl |
| 273 | isopropyl | 1-cyclopropyl-1H-imidazol-4-yl |
| 274 | cyclopentyl | 1-cyclopropyl-1H-imidazol-4-yl |
| 275 | -CH(CH₃)CH₂OH | 1-cyclopropyl-1H-imidazol-4-yl |

TABLE 3-continued

| compound | R₅ | R₄ |
| --- | --- | --- |
| 276 | CH(CH₃)CH₂OH (S) | N-cyclopropyl imidazol-5-yl |
| 277 | CH(CH₃)CH₂F | N-cyclopropyl imidazol-5-yl |
| 278 | CH(CH₃)CH₂F | N-cyclopropyl imidazol-5-yl |
| 279 | CH(CH₃)CHF₂ | N-cyclopropyl imidazol-5-yl |
| 280 | CH(CH₃)CHF₂ | N-cyclopropyl imidazol-5-yl |
| 281 | cyclopropyl | 6-cyclopropylpyridin-3-yl |
| 282 | 1-methylcyclopropyl | 6-cyclopropylpyridin-3-yl |
| 283 | isopropyl | 6-cyclopropylpyridin-3-yl |
| 284 | cyclopentyl | 6-cyclopropylpyridin-3-yl |
| 285 | CH(CH₃)CH₂OH | 6-cyclopropylpyridin-3-yl |
| 286 | CH(CH₃)CH₂OH | 6-cyclopropylpyridin-3-yl |
| 287 | CH(CH₃)CH₂F | 6-cyclopropylpyridin-3-yl |

TABLE 3-continued

| compound | R₅ | R₄ |
| --- | --- | --- |
| 288 | CH(CH₃)CH₂F | 6-cyclopropylpyridin-3-yl |
| 289 | CH(CH₃)CHF₂ | 6-cyclopropylpyridin-3-yl |
| 290 | CH(CH₃)CHF₂ | 6-cyclopropylpyridin-3-yl |
| 291 | cyclopropyl | 5-methyl-4,5,6,7-tetrahydroimidazo[4,5-c]pyridin-1-yl |
| 292 | 1-methylcyclopropyl | 5-methyl-4,5,6,7-tetrahydroimidazo[4,5-c]pyridin-1-yl |
| 293 | isopropyl | 5-methyl-4,5,6,7-tetrahydroimidazo[4,5-c]pyridin-1-yl |
| 294 | cyclopentyl | 5-methyl-4,5,6,7-tetrahydroimidazo[4,5-c]pyridin-1-yl |
| 295 | CH(CH₃)CH₂OH | 5-methyl-4,5,6,7-tetrahydroimidazo[4,5-c]pyridin-1-yl |
| 296 | CH(CH₃)CH₂OH | 5-methyl-4,5,6,7-tetrahydroimidazo[4,5-c]pyridin-1-yl |

TABLE 3-continued

| compound | R₅ | R₄ |
|---|---|---|
| 297 | CH₂F (R) | methyl-tetrahydroimidazopyridine |
| 298 | CH₂F (S) | methyl-tetrahydroimidazopyridine |
| 299 | CHF₂ (R) | methyl-tetrahydroimidazopyridine |
| 300 | CHF₂ (S) | methyl-tetrahydroimidazopyridine |

8. The compound according to claim 1, which is selected from compounds of Formula (Vb) or a pharmaceutically acceptable salt, ester or combination thereof:

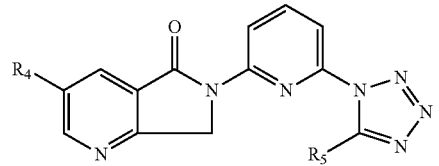

(Vb)

wherein R¹ and R² are delineated for each compound in Table 4,

TABLE 4

| compound | R₅ | R₄ |
|---|---|---|
| 301 | cyclopropyl | O-isopropyl |
| 302 | 1-methylcyclopropyl | O-isopropyl |
| 303 | isopropyl | O-isopropyl |
| 304 | cyclopentyl | O-isopropyl |
| 305 | CH₂OH (R) | O-isopropyl |
| 306 | CH₂OH (S) | O-isopropyl |
| 307 | CH₂F (R) | O-isopropyl |
| 308 | CH₂F (S) | O-isopropyl |
| 309 | CHF₂ (R) | O-isopropyl |
| 310 | CHF₂ (S) | O-isopropyl |
| 311 | cyclopropyl | OCH₂CH₂OCH₃ |
| 312 | 1-methylcyclopropyl | OCH₂CH₂OCH₃ |
| 313 | isopropyl | OCH₂CH₂OCH₃ |
| 314 | cyclopentyl | OCH₂CH₂OCH₃ |
| 315 | CH₂OH (R) | OCH₂CH₂OCH₃ |
| 316 | CH₂OH (S) | OCH₂CH₂OCH₃ |
| 317 | CH₂F (R) | OCH₂CH₂OCH₃ |

TABLE 4-continued

| compound | R₅ | R₄ |
|---|---|---|
| 318 | CH₂F (S-methyl) | -O-CH₂CH₂-O-CH₃ |
| 319 | CHF₂ (R-methyl) | -O-CH₂CH₂-O-CH₃ |
| 320 | CHF₂ (S-methyl) | -O-CH₂CH₂-O-CH₃ |
| 321 | cyclopropyl | (N-methyl morpholine)-CH₂-O- |
| 322 | 1-methylcyclopropyl | (N-methyl morpholine)-CH₂-O- |
| 323 | isopropyl | (N-methyl morpholine)-CH₂-O- |
| 324 | cyclopentyl | (N-methyl morpholine)-CH₂-O- |
| 325 | CH₂OH (R-methyl) | (N-methyl morpholine)-CH₂-O- |
| 326 | CH₂OH (S-methyl) | (N-methyl morpholine)-CH₂-O- |
| 327 | CH₂F (R-methyl) | (N-methyl morpholine)-CH₂-O- |
| 328 | CH₂F (S-methyl) | (N-methyl morpholine)-CH₂-O- |
| 329 | CHF₂ (R-methyl) | (N-methyl morpholine)-CH₂-O- |
| 330 | CHF₂ (S-methyl) | (N-methyl morpholine)-CH₂-O- |
| 331 | cyclopropyl | 4-cyclopropyl-imidazol-1-yl |
| 332 | 1-methylcyclopropyl | 4-cyclopropyl-imidazol-1-yl |
| 333 | isopropyl | 4-cyclopropyl-imidazol-1-yl |
| 334 | cyclopentyl | 4-cyclopropyl-imidazol-1-yl |
| 335 | CH₂OH (R-methyl) | 4-cyclopropyl-imidazol-1-yl |
| 336 | CH₂OH (S-methyl) | 4-cyclopropyl-imidazol-1-yl |
| 337 | CH₂F | 4-cyclopropyl-imidazol-1-yl |

TABLE 4-continued

| compound | R₅ | R₄ |
|---|---|---|
| 338 | CH₂F, CH₃ (stereo) | imidazole-cyclopropyl |
| 339 | CHF₂, CH₃ (stereo) | imidazole-cyclopropyl |
| 340 | CHF₂, CH₃ (stereo, dashed) | imidazole-cyclopropyl |
| 341 | cyclopropyl | morpholine |
| 342 | 1-methylcyclopropyl | morpholine |
| 343 | isopropyl | morpholine |
| 344 | cyclopentyl | morpholine |
| 345 | CH₂OH, CH₃ (stereo) | morpholine |
| 346 | CH₂OH, CH₃ (stereo, dashed) | morpholine |
| 347 | CH₂F, CH₃ (stereo) | morpholine |
| 348 | CH₂F, CH₃ (stereo, dashed) | morpholine |
| 349 | CHF₂, CH₃ (stereo) | morpholine |
| 350 | CHF₂, CH₃ (stereo, dashed) | morpholine |

TABLE 4-continued

| compound | R₅ | R₄ |
|---|---|---|
| 351 | cyclopropyl | piperidine |
| 352 | 1-methylcyclopropyl | piperidine |
| 353 | isopropyl | piperidine |
| 354 | cyclopentyl | piperidine |
| 355 | CH₂OH, CH₃ (stereo) | piperidine |
| 356 | CH₂OH, CH₃ (stereo, dashed) | piperidine |
| 357 | CH₂F, CH₃ (stereo) | piperidine |
| 358 | CH₂F, CH₃ (stereo, dashed) | piperidine |
| 359 | CHF₂, CH₃ (stereo) | piperidine |
| 360 | CHF₂, CH₃ (stereo, dashed) | piperidine |
| 361 | cyclopropyl | 1-ethyl-3-oxopiperazine |
| 362 | 1-methylcyclopropyl | 1-ethyl-3-oxopiperazine |
| 363 | isopropyl | 1-ethyl-3-oxopiperazine |

TABLE 4-continued

| compound | R₅ | R₄ |
|---|---|---|
| 364 | cyclopentyl | N-(piperazin-2-one)-N'-ethyl |
| 365 | CH₂OH, CH₃ (branched) | N-(piperazin-2-one)-N'-ethyl |
| 366 | CH₂OH, CH₃ (branched, stereo) | N-(piperazin-2-one)-N'-ethyl |
| 367 | CH₂F, CH₃ (branched) | N-(piperazin-2-one)-N'-ethyl |
| 368 | CH₂F, CH₃ (branched, stereo) | N-(piperazin-2-one)-N'-ethyl |
| 369 | CHF₂, CH₃ (branched) | N-(piperazin-2-one)-N'-ethyl |
| 370 | CHF₂, CH₃ (branched, stereo) | N-(piperazin-2-one)-N'-ethyl |
| 371 | cyclopropyl | 1-cyclopropyl-1H-imidazol-4-yl |
| 372 | 1-methylcyclopropyl | 1-cyclopropyl-1H-imidazol-4-yl |
| 373 | isobutyl | 1-cyclopropyl-1H-imidazol-4-yl |
| 374 | cyclopentyl | 1-cyclopropyl-1H-imidazol-4-yl |
| 375 | CH₂OH, CH₃ (branched) | 1-cyclopropyl-1H-imidazol-4-yl |
| 376 | CH₂OH, CH₃ (branched, stereo) | 1-cyclopropyl-1H-imidazol-4-yl |
| 377 | CH₂F, CH₃ (branched) | 1-cyclopropyl-1H-imidazol-4-yl |
| 378 | CH₂F, CH₃ (branched, stereo) | 1-cyclopropyl-1H-imidazol-4-yl |
| 379 | CHF₂, CH₃ (branched) | 1-cyclopropyl-1H-imidazol-4-yl |
| 380 | CHF₂, CH₃ (branched, stereo) | 1-cyclopropyl-1H-imidazol-4-yl |
| 381 | cyclopropyl | 6-cyclopropylpyridin-3-yl |
| 382 | 1-methylcyclopropyl | 6-cyclopropylpyridin-3-yl |
| 383 | isobutyl | 6-cyclopropylpyridin-3-yl |
| 384 | cyclopentyl | 6-cyclopropylpyridin-3-yl |
| 385 | CH₂OH, CH₃ (branched) | 6-cyclopropylpyridin-3-yl |

TABLE 4-continued

| compound | R₅ | R₄ |
|---|---|---|
| 386 | (S)-CH₂OH isopropyl-like | 6-cyclopropylpyridin-3-yl |
| 387 | (S)-CH₂F isopropyl | 6-cyclopropylpyridin-3-yl |
| 388 | (R)-CH₂F isopropyl | 6-cyclopropylpyridin-3-yl |
| 389 | (S)-CHF₂ ethyl | 4-cyclopropylpyridin-2-yl |
| 390 | (R)-CHF₂ ethyl | 6-cyclopropylpyridin-3-yl |
| 391 | cyclopropyl | 5-methyl-4,5,6,7-tetrahydroimidazo[4,5-c]pyridin-1-yl |
| 392 | 1-methylcyclopropyl | 5-methyl-4,5,6,7-tetrahydroimidazo[4,5-c]pyridin-1-yl |
| 393 | isopropyl | 5-methyl-4,5,6,7-tetrahydroimidazo[4,5-c]pyridin-1-yl |
| 394 | cyclopentyl | 5-methyl-4,5,6,7-tetrahydroimidazo[4,5-c]pyridin-1-yl |
| 395 | (S)-2-hydroxy-1-methylethyl | 5-methyl-4,5,6,7-tetrahydroimidazo[4,5-c]pyridin-1-yl |
| 396 | (R)-2-hydroxy-1-methylethyl | 5-methyl-4,5,6,7-tetrahydroimidazo[4,5-c]pyridin-1-yl |
| 397 | (S)-CH₂F isopropyl | 5-methyl-4,5,6,7-tetrahydroimidazo[4,5-c]pyridin-1-yl |
| 398 | (R)-CH₂F isopropyl | 5-methyl-4,5,6,7-tetrahydroimidazo[4,5-c]pyridin-1-yl |
| 399 | (S)-CHF₂ ethyl | 5-methyl-4,5,6,7-tetrahydroimidazo[4,5-c]pyridin-1-yl |
| 400 | (R)-CHF₂ ethyl | 5-methyl-4,5,6,7-tetrahydroimidazo[4,5-c]pyridin-1-yl |

9. The compound of claim 1, selected from the compounds set forth below or a pharmaceutically acceptable salt thereof:

| Compound | Structure |
|---|---|
| 1 | 6-(4-cyclopropyl-1H-imidazol-1-yl)-2-(6-(5-isopropyl-1H-tetrazol-1-yl)pyridin-2-yl)isoindolin-1-one |

-continued
| Compound | Structure |
|---|---|
| 2 | 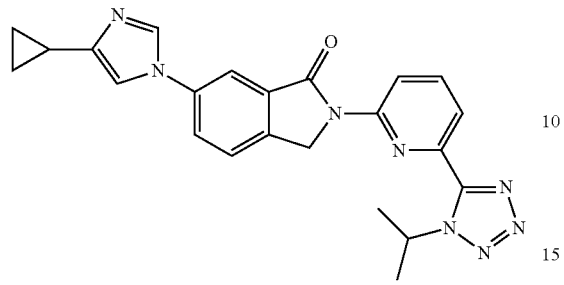 |
| 3 | 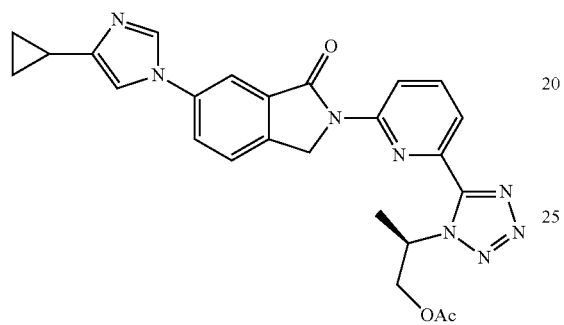 |
| 4 | 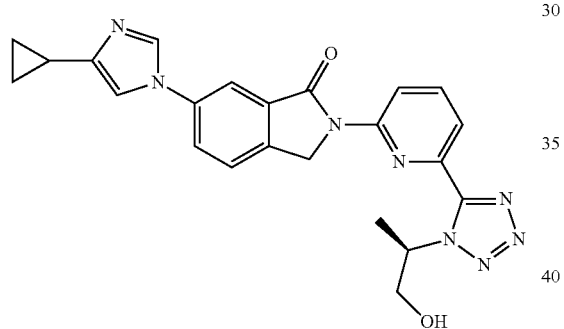 |
| 5 | 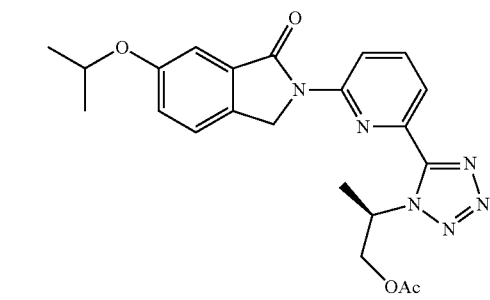 [SMILES: CC(=O)OC[C@@H](C)n1nnnc1-c1cccc(N2Cc3ccc(OC(C)C)cc3C2=O)n1] |
| 6 | 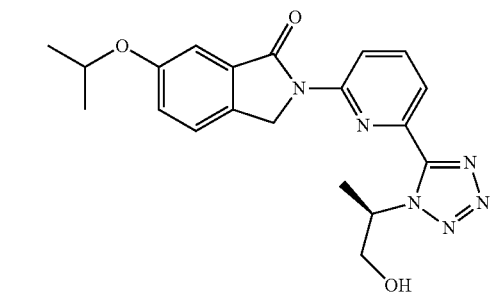 [SMILES: CC(C)Oc1ccc2c(c1)C(=O)N(c1cccc(-c3nnnn3[C@H](C)CO)n1)C2] |
-continued
| Compound | Structure |
|---|---|
| 7 | 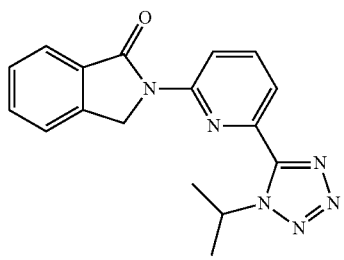 [SMILES: CC(C)n1nnnc1-c1cccc(N2Cc3ccccc3C2=O)n1] |
| 8 | 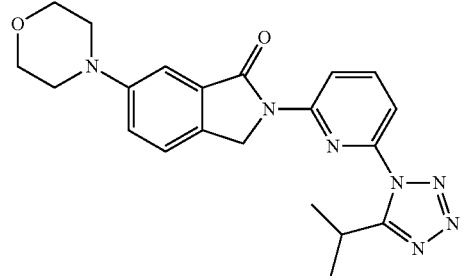 [SMILES: CC(C)c1nnnn1-c1cccc(N2Cc3ccc(N4CCOCC4)cc3C2=O)n1] |
| 9 | 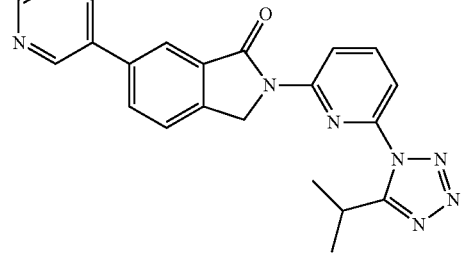 |
| 10 | 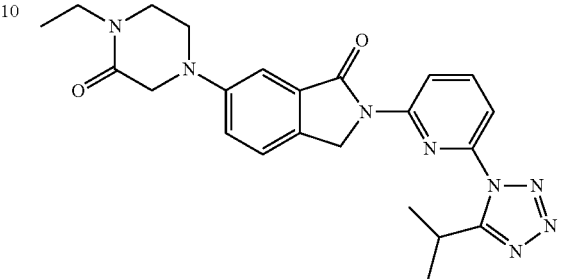 |
| 11 | 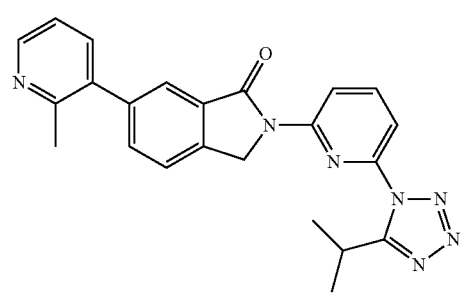 [SMILES: Cc1ncccc1-c1ccc2c(c1)C(=O)N(c1cccc(-n3nnnc3C(C)C)n1)C2] |

-continued

| Compound | Structure |
|---|---|
| 12 | 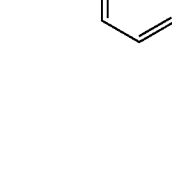 |
| 13 | 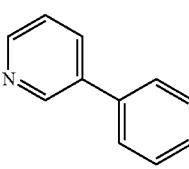 |
| 14 | 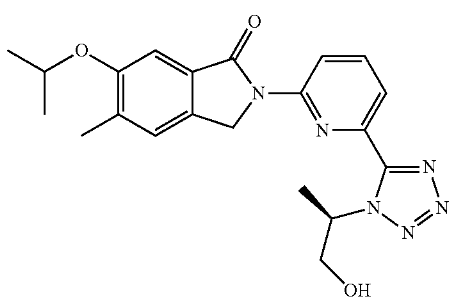 [SMILES: Cc1cc2c(cc1OC(C)C)C(=O)N(c1cccc(-c3nnnn3[C@H](C)CO)n1)C2] |
| 15 | 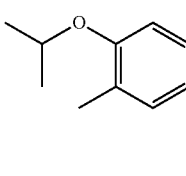 |
| 16 | 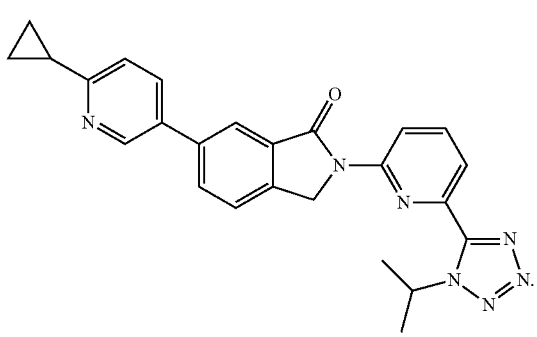 [SMILES: CC(C)n1nnnc1-c1cccc(N2Cc3ccc(-c4ccc(C5CC5)nc4)cc3C2=O)n1] |

10. A pharmaceutical composition comprising a compound according to claim 1 and a pharmaceutically acceptable carrier or excipient.

11. A method for treating a chronic liver disease selected from the group consisting of primary biliary cirrhosis (PBC), cerebrotendinous xanthomatosis (CTX), primary sclerosing cholangitis (PSC), drug induced cholestasis, intrahepatic cholestasis of pregnancy, parenteral nutrition associated cholestasis (PNAC), bacterial overgrowth or sepsis associated cholestasis, autoimmune hepatitis, chronic viral hepatitis, alcoholic liver disease, nonalcoholic fatty liver disease (NAFLD), nonalcoholic steatohepatitis (NASH), liver transplant associated graft versus host disease, living donor transplant liver regeneration, congenital hepatic fibrosis, choledocholithiasis, granulomatous liver disease, intra- or extrahepatic malignancy, Sjogren's syndrome, Sarcoidosis, Wilson's disease, Gaucher's disease, hemochromatosis, and alpha 1-antitrypsin deficiency in a subject in need thereof, comprising administering to the subject a therapeutically effective amount of a compound of claim 1.

12. A method for treating a renal disease selected from the group consisting of diabetic nephropathy, focal segmental glomerulosclerosis (FSGS), hypertensive nephrosclerosis, chronic glomerulonephritis, chronic transplant glomerulopathy, chronic interstitial nephritis, kidney fibrosis and polycystic kidney disease in a subject in need thereof, comprising administering to the subject a therapeutically effective amount of a compound of claim 1.

13. A method for treating a cardiovascular disease selected from the group consisting of atherosclerosis, arteriosclerosis, dyslipidemia, hypercholesterolemia, and hypertriglyceridemia in a subject in need thereof, comprising administering to the subject a therapeutically effective amount of a compound of claim 1.

14. A method for treating a metabolic disease selected from the group consisting of insulin resistance, Type I and Type II diabetes, and obesity in a subject in need thereof, comprising administering to the subject a therapeutically effective amount of a compound of claim 1.

15. The compound of claim 1 wherein $R_3$ is hydrogen and $R_4$ is selected from the groups below

UNITED STATES PATENT AND TRADEMARK OFFICE
CERTIFICATE OF CORRECTION

PATENT NO. : 10,597,382 B2
APPLICATION NO. : 16/113611
DATED : March 24, 2020
INVENTOR(S) : Guoqiang Wang et al.

Page 1 of 1

It is certified that error appears in the above-identified patent and that said Letters Patent is hereby corrected as shown below:

In the Claims

<u>At Column 75</u>
In Claim 3, Line 19, delete "- (Ma)" and insert -- (IIIa) --.

Signed and Sealed this
Seventh Day of July, 2020

Andrei Iancu
*Director of the United States Patent and Trademark Office*